(12) United States Patent
Centore et al.

(10) Patent No.: US 12,383,555 B2
(45) Date of Patent: Aug. 12, 2025

(54) METHODS OF TREATING CANCERS

(71) Applicant: Foghorn Therapeutics Inc., Cambridge, MA (US)

(72) Inventors: Richard C. Centore, Wakefield, MA (US); Lan Xu, Wellesley, MA (US); David L. Lahr, Watertown, MA (US); Ammar Adam, Cambridge, MA (US)

(73) Assignee: FOGHORN THERAPEUTICS INC., Cambridge, MA (US)

( * ) Notice: Subject to any disclaimer, the term of this patent is extended or adjusted under 35 U.S.C. 154(b) by 496 days.

(21) Appl. No.: 17/325,937

(22) Filed: May 20, 2021

(65) Prior Publication Data

US 2022/0079940 A1    Mar. 17, 2022

Related U.S. Application Data

(60) Provisional application No. 63/027,759, filed on May 20, 2020.

(51) Int. Cl.
| | | |
|---|---|---|
| *A61K 31/501* | (2006.01) | |
| *A61K 35/02* | (2015.01) | |
| *A61K 35/04* | (2006.01) | |
| *A61K 39/00* | (2006.01) | |
| *A61K 45/06* | (2006.01) | |
| *A61P 35/02* | (2006.01) | |
| *A61P 35/04* | (2006.01) | |

(52) U.S. Cl.
CPC .......... *A61K 31/501* (2013.01); *A61K 39/00* (2013.01); *A61K 45/06* (2013.01); *A61P 35/02* (2018.01); *A61P 35/04* (2018.01)

(58) Field of Classification Search
CPC ................................ A61P 35/02; A61P 35/04
See application file for complete search history.

(56) References Cited

U.S. PATENT DOCUMENTS

| | | | |
|---|---|---|---|
| 2,788,341 | A | 4/1957 | Schwyzer et al. |
| 3,717,642 | A | 2/1973 | Von Strandtmann |
| 4,109,496 | A | 8/1978 | Allemann et al. |
| 4,650,796 | A | 3/1987 | George et al. |
| 4,868,103 | A | 9/1989 | Stavrianopoulos et al. |
| 5,223,409 | A | 6/1993 | Ladner et al. |
| 5,225,422 | A | 7/1993 | Nagata et al. |
| 5,283,317 | A | 2/1994 | Saifer et al. |
| 5,631,169 | A | 5/1997 | Lakowicz et al. |

(Continued)

FOREIGN PATENT DOCUMENTS

| | | |
|---|---|---|
| CN | 103038231 A | 4/2013 |
| CN | 105473141 A | 4/2016 |

(Continued)

OTHER PUBLICATIONS

Advani, A Phase 1 study of imatinib mesylate in combination with cytarabine and daunorubicin for c-kit positive relapsed acute myeloid leukemia, Leukemia Research, 2010, 34, pp. 1622-1626 (Year: 2010).*

(Continued)

*Primary Examiner* — Renee Claytor
*Assistant Examiner* — Andrew P Lee
(74) *Attorney, Agent, or Firm* — Clark & Elbing LLP

(57) ABSTRACT

The present invention relates to methods and compositions for the treatment of BAF-related disorders such as acute myeloid leukemia.

13 Claims, 6 Drawing Sheets

Specification includes a Sequence Listing.

(56) References Cited

U.S. PATENT DOCUMENTS

| | | | |
|---|---|---|---|
| 5,677,158 A | 10/1997 | Zhou et al. |
| 5,801,030 A | 9/1998 | McVey et al. |
| 5,858,358 A | 1/1999 | June et al. |
| 5,883,223 A | 3/1999 | Gray |
| 6,180,612 B1 | 1/2001 | Hockensmith et al. |
| 6,309,634 B1 | 10/2001 | Bankiewicz et al. |
| 6,352,694 B1 | 3/2002 | June et al. |
| 6,551,786 B2 | 4/2003 | Manfredi |
| 6,683,058 B1 | 1/2004 | Tuszynski |
| 6,692,964 B1 | 2/2004 | June et al. |
| 6,716,662 B2 | 4/2004 | Akai |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 6,995,011 B2 | 2/2006 | Itoh et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,205,103 B2 | 4/2007 | Emerson |
| 7,232,566 B2 | 6/2007 | June et al. |
| 7,572,631 B2 | 8/2009 | Berenson et al. |
| 8,324,367 B2 | 12/2012 | Kaemmerer et al. |
| 8,642,660 B2 | 2/2014 | Goldfarb |
| 8,697,359 B1 | 4/2014 | Zhang |
| 8,703,761 B2 | 4/2014 | Forster et al. |
| 8,771,945 B1 | 7/2014 | Zhang |
| 8,795,965 B2 | 8/2014 | Zhang |
| 8,865,406 B2 | 10/2014 | Zhang et al. |
| 8,946,268 B2 | 2/2015 | Lau et al. |
| 9,072,052 B2 | 6/2015 | Griffin et al. |
| 9,126,985 B2 | 9/2015 | Kley et al. |
| 9,353,051 B2 | 5/2016 | Byrd et al. |
| 9,410,943 B2 | 8/2016 | Kadoch et al. |
| 9,546,206 B2 | 1/2017 | Ring et al. |
| 9,546,296 B2 | 1/2017 | Wang et al. |
| 9,636,323 B2 | 5/2017 | Lin et al. |
| 9,656,959 B2 | 5/2017 | Ni et al. |
| 9,694,084 B2 | 7/2017 | Bradner et al. |
| 9,708,338 B2 | 7/2017 | Yukimasa et al. |
| 9,708,348 B2 | 7/2017 | Castro et al. |
| 9,932,340 B2 | 4/2018 | Dai et al. |
| 10,105,420 B2 | 10/2018 | Kadoch et al. |
| 10,131,637 B2 | 11/2018 | Abdel-Meguid et al. |
| 10,207,998 B2 | 2/2019 | Derbyshire et al. |
| 10,239,888 B2 | 3/2019 | Bradner et al. |
| 10,266,850 B2 | 4/2019 | Doudna et al. |
| 10,464,925 B2 | 11/2019 | Bradner et al. |
| 10,472,376 B2 | 11/2019 | Yamamoto et al. |
| 10,646,575 B2 | 5/2020 | Phillips et al. |
| 10,660,968 B2 | 5/2020 | Phillips et al. |
| 10,669,253 B2 | 6/2020 | Bradner et al. |
| 10,849,982 B2 | 12/2020 | Phillips et al. |
| 10,905,768 B1 | 2/2021 | Phillips et al. |
| 10,976,320 B2 | 4/2021 | Dykhuizen et al. |
| 11,419,859 B2 | 8/2022 | Agresta |
| 11,485,732 B2 | 11/2022 | Vaswani et al. |
| 11,497,752 B2 | 11/2022 | Anthony et al. |
| 11,639,345 B2 | 5/2023 | Bloch et al. |
| 11,773,085 B2 | 10/2023 | Zhou et al. |
| 11,793,802 B2 | 10/2023 | Bearss et al. |
| 11,851,445 B2 | 12/2023 | Ruppel et al. |
| 11,865,114 B2 | 1/2024 | Ramachandra et al. |
| 2002/0022018 A1 | 2/2002 | Curiel et al. |
| 2002/0037281 A1 | 3/2002 | Davidson et al. |
| 2002/0106632 A1 | 8/2002 | Manfredi |
| 2003/0022375 A1 | 1/2003 | Itoh et al. |
| 2003/0027335 A1 | 2/2003 | Ruley et al. |
| 2004/0216178 A1 | 10/2004 | Jones et al. |
| 2005/0079512 A1 | 4/2005 | Emerson et al. |
| 2005/0130919 A1 | 6/2005 | Xu et al. |
| 2006/0058255 A1 | 3/2006 | Chen et al. |
| 2006/0121005 A1 | 6/2006 | Berenson et al. |
| 2007/0105181 A1 | 5/2007 | Pope et al. |
| 2008/0221157 A1 | 9/2008 | Chakravarty et al. |
| 2009/0163545 A1 | 6/2009 | Goldfarb |
| 2010/0048565 A1 | 2/2010 | Frenkel et al. |
| 2010/0197621 A1 | 8/2010 | Henry et al. |
| 2010/0284990 A1 | 11/2010 | Kaemmerer et al. |
| 2011/0230486 A1 | 9/2011 | Lau et al. |
| 2012/0034867 A1 | 2/2012 | Griffin et al. |
| 2012/0035244 A1 | 2/2012 | Chinnaiyan et al. |
| 2012/0308484 A1 | 12/2012 | Szalay et al. |
| 2013/0034867 A1 | 2/2013 | Bomgarden et al. |
| 2014/0068797 A1 | 3/2014 | Doudna et al. |
| 2014/0287931 A1 | 9/2014 | Bernards et al. |
| 2015/0018315 A1 | 1/2015 | Kley et al. |
| 2015/0057169 A1 | 2/2015 | Siu et al. |
| 2015/0376139 A1 | 12/2015 | Abdel-Meguid et al. |
| 2016/0032402 A1 | 2/2016 | Jagani et al. |
| 2016/0130663 A1 | 5/2016 | Kohno et al. |
| 2016/0176916 A1 | 6/2016 | Bradner et al. |
| 2016/0200721 A1 | 7/2016 | Yukimasa et al. |
| 2016/0347708 A1 | 12/2016 | Ebright et al. |
| 2017/0174688 A1 | 6/2017 | Dai et al. |
| 2018/0086720 A1 | 3/2018 | Albrecht et al. |
| 2018/0105500 A1 | 4/2018 | Derbyshire et al. |
| 2018/0140722 A1 | 5/2018 | Willis et al. |
| 2018/0258491 A1 | 9/2018 | Jagani et al. |
| 2018/0328913 A1 | 11/2018 | Kadoch et al. |
| 2020/0069669 A1 | 3/2020 | Grassian et al. |
| 2020/0206344 A1 | 7/2020 | Kadoch et al. |
| 2020/0261434 A1 | 8/2020 | Choe et al. |
| 2021/0009568 A1 | 1/2021 | Zhou et al. |
| 2021/0038611 A1 | 2/2021 | Anthony et al. |
| 2021/0171958 A1 | 6/2021 | Chan et al. |
| 2021/0230154 A1 | 7/2021 | Vaswani et al. |
| 2021/0230190 A1 | 7/2021 | Ruppel et al. |
| 2021/0251988 A1 | 8/2021 | Zhou et al. |
| 2021/0260171 A1 | 8/2021 | Zhou et al. |
| 2021/0388040 A1 | 12/2021 | Kadoch et al. |
| 2022/0016083 A1 | 1/2022 | Centore et al. |
| 2022/0079940 A1 | 3/2022 | Centore et al. |
| 2022/0098190 A1 | 3/2022 | Ruppel et al. |
| 2022/0119378 A1 | 4/2022 | Anthony et al. |
| 2022/0396604 A1 | 12/2022 | Kadoch et al. |
| 2023/0035235 A1 | 2/2023 | Kadoch et al. |
| 2023/0079819 A1 | 3/2023 | Vaswani et al. |
| 2023/0121497 A1 | 4/2023 | Vaswani et al. |
| 2023/0129003 A1 | 4/2023 | Vaswani et al. |
| 2023/0138480 A1 | 5/2023 | Anthony et al. |
| 2023/0145003 A1 | 5/2023 | Wilson et al. |
| 2023/0149414 A1 | 5/2023 | Anthony et al. |
| 2024/0101550 A1 | 3/2024 | Vaswani et al. |
| 2024/0158387 A1 | 5/2024 | Vaswani et al. |
| 2024/0189318 A1 | 6/2024 | Huang |

FOREIGN PATENT DOCUMENTS

| | | | |
|---|---|---|---|
| CN | 104530013 B | 6/2016 |
| CN | 107531668 A | 1/2018 |
| EA | 202192101 A1 | 12/2021 |
| JP | 2008-505963 A | 2/2008 |
| JP | 2011-507910 A | 3/2011 |
| JP | 2011-528016 A | 11/2011 |
| JP | 2016-520515 A | 7/2016 |
| WO | WO-94/10300 A1 | 5/1994 |
| WO | WO-95/30761 A2 | 11/1995 |
| WO | WO-2000/024392 A1 | 5/2000 |
| WO | WO-00/59888 A1 | 10/2000 |
| WO | WO-00/59905 A1 | 10/2000 |
| WO | WO-2005/039643 A2 | 5/2005 |
| WO | WO-2005/112620 A2 | 12/2005 |
| WO | WO-2006/005941 A1 | 1/2006 |
| WO | WO-2006/051063 A1 | 5/2006 |
| WO | WO-2008/022396 A1 | 2/2008 |
| WO | WO-2009/086303 A2 | 7/2009 |
| WO | WO-2010/007046 A2 | 1/2010 |
| WO | WO-2011/115998 A2 | 9/2011 |
| WO | WO-2012/085650 A1 | 6/2012 |
| WO | WO-2013/116663 A1 | 8/2013 |

(56) References Cited

FOREIGN PATENT DOCUMENTS

| | | |
|---|---|---|
| WO | WO-2013116682 A1 | 8/2013 |
| WO | WO-2014/150395 A1 | 9/2014 |
| WO | WO-2015/005473 A1 | 1/2015 |
| WO | WO-2015002230 A1 | 1/2015 |
| WO | WO-2015/103317 A1 | 7/2015 |
| WO | WO-2015/120320 A1 | 8/2015 |
| WO | WO-2015/121688 A1 | 8/2015 |
| WO | WO-2016/054491 A1 | 4/2016 |
| WO | WO-2016/138114 A1 | 9/2016 |
| WO | WO-2016/160718 A1 | 10/2016 |
| WO | WO-2016/207212 A1 | 12/2016 |
| WO | WO-2017/024318 A1 | 2/2017 |
| WO | WO-2017060470 A1 | 4/2017 |
| WO | WO-2017/087885 A1 | 5/2017 |
| WO | WO-2017/118734 A1 | 7/2017 |
| WO | WO-2017/158381 A1 | 9/2017 |
| WO | WO-2018/148443 A1 | 8/2018 |
| WO | WO-2018/160636 A1 | 9/2018 |
| WO | WO-2018/175324 A1 | 9/2018 |
| WO | WO-2019/040098 A1 | 2/2019 |
| WO | WO-2019/138017 A1 | 7/2019 |
| WO | WO-2019/142192 A1 | 7/2019 |
| WO | WO-2019/152437 A1 | 8/2019 |
| WO | WO-2019/152440 A1 | 8/2019 |
| WO | WO-2019/226915 A1 | 11/2019 |
| WO | WO-2020/035779 A1 | 2/2020 |
| WO | WO-2020/081556 A2 | 4/2020 |
| WO | WO-2020/081588 A1 | 4/2020 |
| WO | WO-2020/106915 A1 | 5/2020 |
| WO | WO-2020/127685 A1 | 6/2020 |
| WO | WO-2020/160100 A1 | 8/2020 |
| WO | WO-2020/160180 A1 | 8/2020 |
| WO | WO-2021/081032 A1 | 4/2021 |
| WO | WO-2021/155262 A1 | 8/2021 |
| WO | WO-2021/155264 A1 | 8/2021 |
| WO | WO-2021/155316 A1 | 8/2021 |
| WO | WO-2021/155320 A1 | 8/2021 |
| WO | WO-2021/155321 A2 | 8/2021 |
| WO | WO-2021/183218 A1 | 9/2021 |
| WO | WO-2021/236080 A1 | 11/2021 |
| WO | WO-2022/192621 A1 | 9/2022 |
| WO | WO-2022/198043 A1 | 9/2022 |
| WO | WO-2023/009834 A2 | 2/2023 |
| WO | WO-2023/196560 A1 | 10/2023 |
| WO | WO-2023/196565 A1 | 10/2023 |
| WO | WO-2023/196567 A2 | 10/2023 |
| WO | WO-2024/024428 A1 | 2/2024 |
| WO | WO-2024/031875 A1 | 2/2024 |
| WO | WO-2024/086577 A1 | 4/2024 |

OTHER PUBLICATIONS

Godwin, Gemtuzumab ozogamicin in acute myeloid leukemia, Leukemia, 2017, 31, pp. 1855-1868 (Year: 2017).*
Danziger, Automated site-directed drug design: a general algorithm for knowledge acquisition about hydrogen-bonding regions at protein surfaces, 1989, Proc. R. Soc. Lond., 236, pp. 101-113 (Year: 1989).*
Simone, Oncology: Introduction, Textbook of Medicine, 1997, 20(1), pp. 1004-1010 (Year: 1997).*
Adamo et al., "The oncogene ERG: a key factor in prostate cancer," Oncogene 35(4):403-14 (Jan. 28, 2016).
Anders et al., "HTSeq—a Python framework to work with high-throughput sequencing data," Bioinformatics 31(2):166-9 (Jan. 15, 2015).
Asangani et al., "Therapeutic targeting of BET bromodomain proteins in castration-resistant prostate cancer," available in PMC Dec. 12, 2014. Published in final edited form as: Nature. 510(7504):278-82 (2014) (44 pages).
Attard et al., "Duplication of the fusion of TMPRSS2 to ERG sequences identifies fatal human prostate cancer," available in PMC Feb. 24, 2009. Published in final edited form as: Oncogene. 27(3):253-63 (2008) (19 pages).
Basuyaux et al., "The Ets transcription factors interact with each other and with the c-Fos/c-Jun complex via distinct protein domains in a DNA-dependent and-independent manner," J Biol Chem. 272(42):26188-95 (1997).
Bendall et al., "Prevention of amino acid conversion in SILAC experiments with embryonic stem cells," Mol Cell Proteomics. 7(9):1587-97 (2008).
Berger et al., "Androgen-induced differentiation and tumorigenicity of human prostate epithelial cells," Cancer Res. 64(24):8867-75 (2004).
Börno et al., "Genome-wide DNA methylation events in TMPRSS2-ERG fusion-negative prostate cancers implicate an EZH2-dependent mechanism with miR-26a hypermethylation," Cancer Discov. 2(11):1024-35 (2012).
Camuzeaux et al., "Imaging Erg and Jun transcription factor interaction in living cells using fluorescence resonance energy transfer analyses," Biochem Biophys Res Commun. 332(4):1107-14 (2005).
Cancer Genome Atlas Research Network, "The Molecular Taxonomy of Primary Prostate Cancer," Cell. 163(4):1011-25 (2015) (16 pages).
Carell et al., "A novel procedure for the synthesis of libraries containing small organic molecules," Angew Chem Int Ed Engl. 33(20):2059-2061 (1994).
Carell et al., "A Solution-Phase Screening Procedure for the Isolation of Active Compounds from a Library of Molecules," Angewandte Chemie International Edition in English. 33(20): 2061-2064 (1994).
Chen et al., "ETS factors reprogram the androgen receptor cistrome and prime prostate tumorigenesis in response to PTEN loss," available in PMC Feb. 1, 2014. Published in final edited form as: Nat Med. 19(8):1023-9 (2013) (21 pages).
Chng et al., "A transcriptional repressor co-regulatory network governing androgen response in prostate cancers," EMBO J. 31(12):2810-23 (2012).
Cho et al., "An unnatural biopolymer," Science. 261(5126):1303-1305 (1993).
Cull et al., "Screening for receptor ligands using large libraries of peptides linked to the C terminus of the lac repressor," Proc Natl Acad Sci. 89(5):1865-1869. (1992).
Cwirla et al., "Peptides on phage: A vast library of peptides for identifying ligands," Proc Nati Acad Sci. 87:6378-6382 (1990).
Delattre et al., "Gene fusion with an ETS DNA-binding domain caused by chromosome translocation in human tumours," Nature. 359(6391):162-5 (1992).
Demichelis et al., "TMPRSS2:ERG gene fusion associated with lethal prostate cancer in a watchful waiting cohort," Oncogene 26:4596-4599 (2007).
Devlin et al., "Random Peptide Libraries: a Source of Specific Protein Binding Molecules," Science. 249(4967):404-406 (1990).
DeWitt et al., "Diversomers': an approach to nonpeptide, nonoligomeric chemical diversity," Proc Natl Acad Sci. 90(15):6909-6913 (1993).
Dobin et al., "STAR: ultrafast universal RNA-seq aligner," Bioinformatics. 29(1):15-21 (2013).
Donaldson et al., "Solution structure of the ETS domain from murine Ets-1: a winged helix-turn-helix DNA binding motif," EMBO J. 15(1):125-34 (1996).
Erb et al., "Recursive deconvolution of combinatorial chemical libraries," Proc Natl Acad Sci. 91(24):11422-11426 (1994).
Extended European Search Report for European Application No. 19748410.8, dated Sep. 24, 2021 (10 pages).
Extended European Search Report for European Application No. 19887386.1, dated Dec. 5, 2022 (18 pages).
Extended European Search Report for European Application No. 20749261.2, dated Oct. 18, 2022 (8 pages).
Felici et al., "Selection of antibody ligands from a large library of oligopeptides expressed on a multivalent exposition vector," J Mol Biol. 222(2):301-10 (1991).
Feng et al., "GFOLD: a generalized fold change for ranking differentially expressed genes from RNA-seq data," Bioinformatics. 28(21):2782-8 (2012).
Fodor et al., "Multiplexed biochemical assays with biological chips," Nature. 364:555-556 (1993).

(56) References Cited

OTHER PUBLICATIONS

Gallop et al., "Applications of Combinatorial Technologies to Drug Discovery. 1. Background and Peptide Combinatorial Libraries," J Med Chem 37(9):1233-51 (1994).
Gene Ontology Consortium, "Gene Ontology Consortium: going forward," Nucleic Acids Res. 43(Database issue): D1049-56 (2015).
Helgeson et al., "Characterization of TMPRSS2:ETV5 and SLC45A3:ETV5 gene fusions in prostate cancer," Cancer Res. 68(1):73-80 (2008).
Ho et al., "An embryonic stem cell chromatin remodeling complex, esBAF, is essential for embryonic stem cell self-renewal and pluripotency," Proc Natl Acad Sci U S A. 106(13):5181-6 (2009).
Houghten et al., "The use of synthetic peptide combinatorial libraries for the identification of bioactive peptides," Biotechniques. 13(3):412-21 (1992).
Ichikawa et al., "An RNA-binding protein gene, TLS/FUS, is fused to ERG in human myeloid leukemia with t(16;21) chromosomal translocation," Cancer Res. 54(11):2865-8 (1994).
International Preliminary Report on Patentability for International Application No. PCT/US2016/062911 issued May 22, 2018 (13 pages).
International Preliminary Report on Patentability for International Application No. PCT/US2019/015722, issued Aug. 4, 2020 (6 pages).
International Preliminary Report on Patentability for International Application No. PCT/US2020/033829, issued Nov. 17, 2022 (6 pages).
International Search Report and Written Opinion for International Application No. PCT/US19/15722, mailed May 31, 2019 (12 pages).
International Search Report and Written Opinion for International Application No. PCT/US2016/062911 dated Mar. 3, 2017 (16 pages).
International Search Report and Written Opinion for International Application No. PCT/US2020/015605, mailed Jun. 16, 2020 (15 pages).
International Search Report and Written Opinion for International Application No. PCT/US2020/015723, mailed Jul. 2, 2020 (15 pages).
International Search Report and Written Opinion for International Application No. PCT/US2020/033829, mailed Aug. 17, 2020 (14 pages).
International Search Report and Written Opinion for International Application No. PCT/US2022/019506, dated Jun. 7, 2022 (9 pages).
International Search Report and Written Opinion for International Application No. PCT/US21/15876, mailed on Apr. 7, 2021 (23 pages).
International Search Report and Written Opinion for International Application No. PCT/US21/15878, dated Jun. 4, 2021 (10 pages).
International Search Report and Written Opinion for International Patent Application No. PCT/US2019/062525, mailed Feb. 18, 2020 (14 pages).
Kadoch et al., "Mammalian SWI/SNF chromatin remodeling complexes and cancer: Mechanistic insights gained from human genomics," Sci Adv. 1(5):e1500447 (2015) (17 pages).
Kadoch et al., "Proteomic and bioinformatic analysis of mammalian SWI/SNF complexes identifies extensive roles in human malignancy," Nat Genet. 45(6):592-601 (2013) (11 pages).
Kadoch et al., "Reversible Disruption of mSWI/SNF (BAF) Complexes by the SS18-SSX Oncogenic Fusion in Synovial Sarcoma," available in PMC May 16, 2013, published in final edited form as: Cell. 153(1):71-85 (2013) (26 pages).
Karim et al., "The ETS-domain: a new DNA-binding motif that recognizes a purine-rich core DNA sequence," Genes Dev. 4(9):1451-3 (1990).
Klezovitch et al., "A causal role for ERG in neoplastic transformation of prostate epithelium," Proc Natl Acad Sci U S A. 105(6):2105-10 (2008).
Kumar-Sinha et al., "Recurrent gene fusions in prostate cancer," available in PMC Jul. 16, 2009. Published in final edited form as: Nat Rev Cancer. 8(7):497-511 (2008) (29 pages).

Kunderfranco et al., "ETS transcription factors control transcription of EZH2 and epigenetic silencing of the tumor suppressor gene Nkx3.1 in prostate cancer," PLoS One. 5(5):e10547 (2010) (17 pages).
Lam et al., "A new type of synthetic peptide library for identifying ligand-binding activity," Nature. 354(6348):82-84 (1991).
Lam, "Application of combinatorial library methods in cancer research and drug discovery," Anticancer Drug Des. 12(3):145-67 (1997).
Langmead et al., "Fast gapped-read alignment with Bowtie 2," available in PMC Apr. 1, 2013. Published in final edited form as: Nat Methods. 9(4):357-9 (2012) (8 pages).
Link et al., "Targeting the BAF57 SWI/SNF subunit in prostate cancer: a novel platform to control androgen receptor activity," Cancer Res. 68(12):4551-8 (2008).
Love et al., "Moderated estimation of fold change and dispersion for RNA-seq data with DESeq2," Genome Biol. 15(12):550 (2014) (21 pages).
Lupien et al., "FoxA1 translates epigenetic signatures into enhancer-driven lineage-specific transcription," Cell. 132(6):958-70 (2008).
Machanick et al., "MEME-ChIP: motif analysis of large DNA datasets," Bioinformatics. 27(12):1696-7 (2011).
Mackereth et al., "Diversity in structure and function of the Ets family PNT domains," J Mol Biol. 342(4):1249-64 (2004).
Madura et al., "N-recognin/Ubc2 interactions in the N-end rule pathway," J Biol Chem. 268(16):12046-54 (1993).
McBride et al., "Disruption of mammalian SWI/SNF and polycomb complexes in human sarcomas: mechanisms and therapeutic opportunities," J Pathol. 244(5): 638-649 (Apr. 2018).
Meléet al., "The human transcriptome across tissues and individuals," available in PMC Aug. 24, 2015. Published in final edited form as: Science. 348(6235):660-5 (2015) (12 pages).
Mounir et al., "ERG signaling in prostate cancer is driven through PRMT5-dependent methylation of the Androgen Receptor," Elife. 5:e13964 (2016) (19 pages).
Nagaich et al., "Rapid periodic binding and displacement of the glucocorticoid receptor during chromatin remodeling," Mol Cell. 14(2):163-74 (2004).
Nam et al., "Expression of the TMPRSS2:ERG fusion gene predicts cancer recurrence after surgery for localised prostate cancer," Br J Cancer. 97(12):1690-5 (2007).
Office Action for Chinese Patent Application No. 201980023925.9, dated Apr. 20, 2022 (13 pages).
Ong et al., "A practical recipe for stable isotope labeling by amino acids in cell culture (SILAC)," Nat Protoc. 1(6):2650-60 (2006).
Papillon et al., "Discovery of Orally Active Inhibitors of Brahma Homolog (BRM)/SMARCA2 ATPase Activity for the Treatment of Brahma Related Gene 1 (BRG1)/SMARCA4-Mutant Cancers," J Med Chem. 61(22):10155-72 (Nov. 2018).
Partial Supplementary European Search Report for European Patent Application No. 19887386.1, dated Jul. 20, 2022 (23 pages).
Paulo et al., "FLI1 is a novel ETS transcription factor involved in gene fusions in prostate cancer," Genes Chromosomes Cancer. 51(3):240-9 (2012).
Petrovics et al., "Frequent overexpression of ETS-related gene-1 (ERG1) in prostate cancer transcriptome," Oncogene. 24(23):3847-52 (2005).
Pomerantz et al., "The androgen receptor cistrome is extensively reprogrammed in human prostate tumorigenesis," available in PMC May 1, 2016. Published in final edited form as: Nat Genet. 47(11):1346-51 (2015) (17 pages).
Prensner et al., "The long noncoding RNA SChLAP1 promotes aggressive prostate cancer and antagonizes the SWI/SNF complex," available in PMC May 1, 2014. Published in final edited form as: Nat Genet. 45(11):1392-8 (2013) (26 pages).
PubChem CID 117640569, "N-[2-[[4-(4-Methoxyphenyl)-1,3-thiazol-2-yl]amino]-2-oxoethyl]-1,3-thiazole-5-carboxamide," https://pubchem.ncbi.nlm.nih.gov/compound/117640569, created Feb. 23, 2016 (9 pages).
PubChem CID 56442706, "1-(4-Methoxyphenyl)-N-[2-oxo-2-[4-(1,2,4-triazol-1-yl) anilino]ethyl]pyrazole-3-carboxamide," https://pubchem.ncbi.nlm.nih.gov/compound/56442706, created Jan. 25, 2012 (8 pages).

(56) References Cited

OTHER PUBLICATIONS

PubChem CID 91946137, "N-[2-[(1-Ethylpyrazol-3-yl}amino]-2-oxoethyl]-1-methylpyrazole-3-carboxamide," https://pubchem.ncbi.nlm.nih.gov/compound/91946137, created Oct. 22, 2015 (8 pages).
PubChem Compound Summary for CID 155037309, dated Dec. 19, 2020 (9 pages).
PubChem Compound Summary for CID No. 136572628, "4-Chloro-N-[2-(cyclopentylamino)-2-oxoethyl]-5-nitro-1H-pyrazole-3-carboxamide," created Jan. 24, 2019, <https://pubchem.ncbi.nlm.nih.gov/compound/136572628>, (7 pages).
PubChem Compound Summary for CID No. 49726797, "N-Methyl-N-(2-oxo-2-((4-(pyridin-3-yl)thiazol-2-yl)amino)ethyl)-1H-indole-3-carboxamide," created Nov. 27, 2010, <https://pubchem.ncbi.nlm.nih.gov/compound/49726797>, (8 pages).
PubChem Compound Summary for CID No. 91945707, "N-[2-[(4,5-Dimethyl-1,3-thiazol-2-yl)amino]-2-oxoethyl]-1-methylpyrazole-3-carboxamide," created Oct. 22, 2015 <https://pubchem.ncbi.nlm.nih.gov/compound/91945707>, (8 pages).
PubChem Compound Summary for PubChem CID 49726798, "N-(2-((4-(Furan-2-yl)thiazol-2-yl)amino)-2-oxoethyl)-N-methyl-1H-indole-3-carboxamide," created Nov. 27, 2010 <https://pubchem.ncbi.nih.gov/compound/49726798> (8 pages).
PubChem Compound Summary for SID 172131678, dated Dec. 9, 2014 (8 pages).
Pubchem, "Compound Summary for CID 108452511," <https://pubchem.ncbi.nlm.nih.gov/compound/108452511>, created Jan. 15, 2016, retrieved Jan. 4, 2021 (7 pages).
Pubchem, "Compound Summary for CID 2955118," <https://pubchem.ncbi.nlm.nih.gov/compound/2955118>, created Jul. 29, 2005, retrieved Mar. 22, 2017 (13 pages).
Pubchem, "Compound Summary for CID 7325930," <https://pubchem.ncbi.nlm.nih.gov/compound/7325930>, created Jul. 29, 2006, retrieved Mar. 22, 2017 (11 pages).
Pubchem, "Compound Summary for CID 970466," <https://pubchem.ncbi.nlm.nih.gov/compound/970466>, created Jul. 9, 2005, retrieved Mar. 22, 2017 (11 pages).
Quinlan et al., "BEDTools: a flexible suite of utilities for comparing genomic features," Bioinformatics. 26(6):841-2 (2010).
Rajput et al., "Frequency of the TMPRSS2:ERG gene fusion is increased in moderate to poorly differentiated prostate cancers," J Clin Pathol. 60(11):1238-43 (2007).
Rappsilber et al., "Protocol for micro-purification, enrichment, pre-fractionation and storage of peptides for proteomics using StageTips," Nat Protoc. 2(8):1896-906 (2007).
Scott et al., "Searching for peptide ligands with an epitope library," Science. 249(4967):386-390 (1990).
Shen et al., "The SWI/SNF ATPase Brm is a gatekeeper of proliferative control in prostate cancer," Cancer Res. 68(24):10154-62 (Dec. 2008).
Shi et al., "Role of SWI/SNF in acute leukemia maintenance and enhancer-mediated Myc regulation," Genes Dev. 27(24):2648-62 (Dec. 2013).
Siegel et al., "Cancer statistics, 2015," CA Cancer J Clin. 65(1):5-29 (2015).
Subramanian et al., "Gene set enrichment analysis: a knowledge-based approach for interpreting genome-wide expression profiles," Proc Natl Acad Sci USA. 102(43):15545-50 (2005).
Sun et al., "TMPRSS2-ERG fusion, a common genomic alteration in prostate cancer activates C-MYC and abrogates prostate epithelial differentiation," available in PMC Oct. 4, 2020. Published in final edited form as: Oncogene. 27(40)5348-53 (2008) (12 pages).
Tikdari et al., "Reaction of 2-Aminothiazoles with 5-Oxazolones," ChemInform. 18(47):Abstract 199 (1987) (1 page).
Tikdari et al., "Reaction of 2-Aminothiazoles with 5-Oxazolones," Indian Journal of Chemistry 26B:478-9 (May 1987).
Tomlins et al., "Recurrent fusion of TMPRSS2 and ETS transcription factor genes in prostate cancer," Science.310(5748):644-8 (2005).
Tomlins et al., "Role of the TMPRSS2-ERG gene fusion in prostate cancer," Neoplasia. 10(2):177-88 (2008) (21 pages).
Tomlins et al., "TMPRSS2:ETV4 gene fusions define a third molecular subtype of prostate cancer," Cancer Res. 66(7):3396-400 (2006).
Tuoc et al., "Chromatin regulation by BAF170 controls cerebral cortical size and thickness," Dev Cell. 25(3):256-69 (May 2013).
Vachtenheim et al., "SWI/SNF chromatin remodeling complex is critical for the expression of microphthalmia-associated transcription factor in melanoma cells," Biochemical and Biophysical Research Communications. 392(3):454-459 (2010).
Varambally et al., "The polycomb group protein EZH2 is involved in progression of prostate cancer," Nature. 419(6907):624-9 (2002).
Vela et al., "Discovery of Enhancers of the Secretion of Leukemia Inhibitory Factor for the Treatment of Multiple Sclerosis," J Biomol Screen. 21(5):437-45 (Jun. 2016).
Verger et al., "Identification of amino acid residues in the ETS transcription factor Erg that mediate Erg-Jun/Fos-DNA ternary complex formation," J Biol Chem. 276(20):17181-9 (2001).
Wollenick et al., "Synthetic transactivation screening reveals ETV4 as broad coactivator of hypoxia-inducible factor signaling," Nucleic Acids Res. 40(5):1928-43 (2012).
Yang et al., "EZH2, an epigenetic driver of prostate cancer," Protein Cell. 4(5):331-41 (2013).
Yildirim et al., "Mbd3/NURD complex regulates expression of 5-hydroxymethylcytosine marked genes in embryonic stem cells," Cell. 147(7):1498-510 (2011).
Yu et al., "An integrated network of androgen receptor, polycomb, and TMPRSS2-ERG gene fusions in prostate cancer progression," Cancer Cell. 17(5):443-54 (2010).
Yu et al., "Direct recruitment of polycomb repressive complex 1 to chromatin by core binding transcription factors," Mol Cell. 45(3):330-43 (2012).
Zervos et al., "Mxi1, a protein that specifically interacts with Max to bind Myc-Max recognition sites," Cell. 72(2):223-32 (1993).
Zhang et al., "Model-based analysis of ChIP-Seq (MACS)," Genome Biol. 9(9):R137 (2008) (9 pages).
Zong et al., "ETS family transcription factors collaborate with alternative signaling pathways to induce carcinoma from adult murine prostate cells," Proc Natl Acad Sci U S A. 106(30):12465-70 (Jul. 2009).
Zuckermann et al., "Discovery of Nanomolar Ligands for 7-Transmembrane G-Protein-Coupled Receptors from a Diverse N-(Substituted)glycine Peptoid Library," J Med Chem. 37(17):2678-2685 (1994).
Zvarec et al., "5-Benzylidenerhodanine and 5-benzylidene-2-4-thiazolidinedione based antibacterials," Bioorg Med Chem Lett. 22(8):2720-2 (2012).
U.S. Appl. No. 18/281,022, Vaswani et al.
U.S. Appl. No. 18/282,279, Huang, Liyue.
U.S. Appl. No. 18/373,518, Huang et al.
Alazawi, "Foghorn Therapeutics," Blackseed Bio, last updated Mar. 4, 2022, retrieved Jul. 24, 2023, from <https://blackseedbio.com/reports/fhtx#pipeline> (26 pages).
Dominguez et al. "Beyond editing: Repurposing CRISPR-Cas9 for Precision Genome Regulation and Interrogation," available in PMC Jun. 27, 2016, published in final edited form as: Nat Rev Mol Cell Biol. 17(1):5-15 (Jan. 2016) (24 pages).
Fathi et al., "Differentiation syndrome with lower-intensity treatments for acute myeloid leukemia," Am J Hematol. 96(6):735-46 (Jun. 1, 2021) (13 Pages).
Gaj et al. "ZFN, Talen and CRISPR/Cas-based Methods for Genome Engineering," available in PMC Jul. 1, 2014, published in final edited form as: Trends Biotechnol. 31(7):397-405 (Jul. 2013) (20 pages).
International Search Report and Written Opinion for International Application No. PCT/US2023/017839, mailed Sep. 6, 2023 (11 pages).
International Search Report and Written Opinion for International Application No. PCT/US23/17821, mailed Jun. 30, 2023 (9 pages).
International Search Report and Written Opinion for International Application No. PCT/US23/17829, mailed Aug. 23, 2023 (15 pages).
Kadoch et al. "Reversible Disruption of mSWI/SNF (BAF) Complexes by the SS18-SSX Oncogenic Fusion in Synovial Sarcoma,"

(56) References Cited

OTHER PUBLICATIONS available in PMC May 16, 2013, published in final edited form as: Cell. 153(1):71-85 (Mar. 2013) (26 pages).
Tsai et al. "Dimeric CRISPR RNA-guided FokI Nucleases for Highly Specific Genome Editing," available in PMC Dec. 1, 2014, published in final edited form as: Nat Biotechnol. 32(6):569-576 (Jun. 2014) (22 pages).
Database Registry, RN 878254-76-3, entered Mar. 28, 2006 (1 page).
Database Registry, RN 1004932-80-2, entered Feb. 21, 2008 (1 page).
Database Registry, RN 1175782-23-6, entered Aug. 26, 2009 (1 page).
Database Registry, RN 1315743-98-6, entered Aug. 11, 2011 (1 page).
Centore et al., "Abstract 1224: Discovery of novel BAF inhibitors for the treatment of transcription factor-driven cancers," Poster Presentations—Proffered abstracts, Cancer Research 81(13_Supplement):1224 (Jul. 1, 2021) (2 pages).
Extended European Search Report for European Application No. 21748261.1, dated Jan. 29, 2024 (17 pages).
International Preliminary Report on Patentability for International Application No. PCT/US2022/019506, issued Sep. 12, 2023 (6 pages).
International Preliminary Report on Patentability for International Application No. PCT/US2022/020943, issued Sep. 12, 2023 (5 pages).
International Search Report and Written Opinion for International Application No. PCT/US2023/077088, mailed Mar. 4, 2024 (17 pages).
International Search Report and Written Opinion for PCT/US2022/020943, dated Jun. 14, 2022 (17 pages).
Mill et al., "RUNX1-targeted therapy for AML expressing somatic or germline mutation in RUNX1," Blood 134(1):59-73 (Jul. 4, 2019).
Partial Supplementary European Search Report for European Patent Application No. 20936213.6, dated Feb. 8, 2024 (20 pages).
Ramos et al., "Current Approaches in the Treatment of Relapsed and Refractory Acute Myeloid Leukemia," J Clin Med. 4(4):665-95 (Apr. 2015).
STN Registry Database, RN 1010893-05-6, entered Mar. 30, 2008 (2 pages).
STN Registry Database, RN 1049271-26-2, entered Sep. 14, 2008 (2 pages).
STN Registry Database, RN 1081662-32-9, entered Dec. 8, 2008 (2 pages).
STN Registry Database, RN 1209112-42-4, entered Mar. 12, 2010 (2 pages).
STN Registry Database, RN 1246047-75-5, entered Oct. 12, 2010 (2 pages).
STN Registry Database, RN 1308280-67-2, entered Jun. 9, 2011 (2 pages).
STN Registry Database, RN 1351682-19-3, entered Dec. 22, 2011 (2 pages).
STN Registry Database, RN 1401558-47-1, entered Oct. 22, 2012 (2 pages).
STN Registry Database, RN 1455783-72-8, entered Oct. 6, 2013 (2 pages).
STN Registry Database, RN 1576383-94-2, entered Mar. 31, 2014 (2 pages).
STN Registry Database, RN 1586193-45-4, entered Apr. 17, 2014 (2 pages).
STN Registry Database, RN 1827759-12-5, entered Dec. 13, 2015 (2 pages).
STN Registry Database, RN 1831899-24-1, entered Dec. 17, 2015 (2 pages).
STN Registry Database, RN 1839545-15-1, entered Dec. 31, 2015 (2 pages).
STN Registry Database, RN 923768-18-7, entered Feb. 28, 2007 (2 pages).
STN Registry Database, RN 923809-79-4, entered Feb. 28, 2007 (2 pages).
STN Registry Database, RN 931893-54-8, entered Apr. 23, 2007 (2 pages).
STN Registry Database, RN 932130-00-2, entered Apr. 24, 2007 (2 pages).
STN Registry Database, RN 938283-11-5, entered Jun. 22, 2007 (2 pages).
"FLI1 gene," MedlinePlus, published May 1, 2012, <https://medlineplus.gov/genetics/> (3 pages).
Adam et al., International Application No. PCT/US2024/024407, filed Apr. 12, 2024 by applicant Foghorn Therapeutics Inc. (42 pages).
Adam et al., International Application No. PCT/US2024/024428, filed Apr. 12, 2024 by applicant Foghorn Therapeutics Inc. (40 pages).
Boulay et al., "Cancer-Specific Retargeting of BAF Complexes by a Prion-like Domain," Cell 171(1):163-78 (Sep. 21, 2017) (36 pages).
CAS RN: 1223164-86-0; STN entry date: May 14, 2010; N-[2-[[4-(3-Fluoro-4-methoxyphenyl)-2-thiazolyl]amino]-2-oxoethyl]-2-methyl-3-furancarboxamide (1page).
CAS RN: 1300403-14-8; STN entry date May 25, 2011; 5-Methyl-N-[2-oxo-2-[ (5-phenyl-2-pyridinyl)amino]ethyl]-2-thiophenecarboxamide (1 page).
CAS RN: 924410-17-3; STN entry date: Mar. 2, 2007; 5-Methyl-N-[2-oxo-2-[ (4-phenyl-2-thiazolyl)amino]ethyl]-2-thiophenecarboxamide (1 page).
CAS RN: 924420-04-2; STN entry date: Mar. 2, 2007; 5-Methyl-N-[2-oxo-2-[[4-(4-pyridinyl)-2-thiazolyl]amino]ethyl]-2-thiophenecarboxamide (1 page).
Chandler et al., "ARID1a-DNA interactions are required for promoter occupancy by SWI/SNF," Mol Cell Biol. 33(2):265-80 (Jan. 2013).
Chattopadhyay et al., "Uveal melanoma: From diagnosis to treatment and the science in between," Cancer. 122(15):2299-2312 (26 pages) (Aug. 2016).
Database Registry, RN 1323331-37-8, entered Aug. 25, 2011 (1 page).
Database Registry, RN 1323542-96-6, entered Aug. 26, 2011 (1 page).
Database Registry, RN 1324163-01-0, entered Aug. 28, 2011 (1 page).
Database Registry, RN 1327304-26-6, entered Sep. 2, 2011 (1 page).
Fadul et al., "EWS/FLI utilizes NKX2-2 to repress mesenchymal features of Ewing sarcoma," Genes Cancer 6(3-4):129-43 (Mar. 2015).
Grohar et al., "Ecteinascidin 743 interferes with the activity of EWS-FLI1 in Ewing sarcoma cells," Neoplasia 13(2):145-53 (Feb. 2011).
Herrero-Martín et al., "Stable interference of EWS-FLI1 in an Ewing sarcoma cell line impairs IGF-1/IGF-1R signalling and reveals TOPK as a new target," Br J Cancer 101(1):80-90 (Jul. 7, 2009).
Hohmann et al., "Sensitivity and engineered resistance of myeloid leukemia cells to BRD9 inhibition," Nat Chem Biol. 12(9): 672-679 (Sep. 2016) (12 pages).
International Preliminary Report on Patentability for International Application No. PCT/US2019/056312, mailed Apr. 14, 2021 (10 pages).
International Search Report and Written Opinion for International Application No. PCT/US18/000339 dated Jan. 28, 2019 (13 pages).
International Search Report and Written Opinion for International Application No. PCT/US19/56312, dated Jan. 14, 2020 (14 pages).
International Search Report and Written Opinion for International Application No. PCT/US19/56365 dated Jan. 30, 2020 (8 pages).
International Search Report and Written Opinion for International Application No. PCT/US2024/024407, mailed Jun. 24, 2024 (15 pages).
International Search Report and Written Opinion for International Application No. PCT/US2024/024428, mailed Jul. 16, 2024 (18 pages).

(56) References Cited

OTHER PUBLICATIONS

Kedage et al., "An Interaction with Ewing's Sarcoma Breakpoint Protein EWS Defines a Specific Oncogenic Mechanism of ETS Factors Rearranged in Prostate Cancer," Cell Rep. 17(5):1289-301 (Oct. 25, 2016) (14 pages).
Michel et al., "Abstract PR15: BRD9 defines a novel mammalian SWI/SNF (BAF) complex configuration which supports proliferation in AML," Clin Cancer Res. 23(24_Suppl) Abstract PR15 (2017) (4 pages).
Piel et al., International Application No. PCT/US2024/031875, filed May 31, 2024 by applicant Foghorn Therapeutics Inc. (47 pages).
Rago et al., "Exquisite Sensitivity to Dual BRG1/BRM ATPase Inhibitors Reveals Broad SWI/SNF Dependencies in Acute Myeloid Leukemia," Mol Cancer Res. 20(3):361-72 (Mar. 1, 2022).
Riggi et al., "EWS-FLI1 utilizes divergent chromatin remodeling mechanisms to directly activate or repress enhancer elements in Ewing sarcoma," Cancer Cell 26(5):668-81 (Nov. 10, 2014).
Sankar et al., "Promiscuous partnerships in Ewing's sarcoma," Cancer Genet. 204(7):351-65 (Jul. 2011).
STN Registry Database, CAS RN 858073-83-3, Albany Molecular Research, Inc., entered Aug. 3, 2005 (1 page).
Takigami et al., "Synthetic siRNA targeting the breakpoint of EWS/Fli-1 inhibits growth of Ewing sarcoma xenografts in a mouse model," Int J Cancer 128(1):216-26 (Jan. 1, 2011).
Wu et al., "Targeting the chromatin remodeling enzyme BRG1 increases the efficacy of chemotherapy drugs in breast cancer cells," Oncotarget 7(19):27158-75 (May 10, 2016).
Collins et al., "Abstract 2122: The dual BRM/BRG1 (SMARCA2/4) inhibitor FHD-286 induces differentiation in preclinical models of AML," Cancer Res. 83(7_Supplement) (Apr. 2023) (5 pages).
Fiskus et al., "Pre-Clinical Efficacy of Targeting Baf Complexes through Inhibition of the Dual Atpases BRG1 and BRM By FHD-286 in Cellular Models of AML of Diverse Genetic Background," Blood. 140(Supplement 1):8819-20 (Nov. 2022) (15 pages).
Hentemann, "Abstract ND14: Pharmacological profile and anti-tumor properties of FHD-286: A novel BAF inhibitor for the treatment of transcription factor-driven cancers," Cancer Res. 82(12_Supplement): ND14 (Jun. 2022) (4 pages).
International Search Report and Written Opinion for International Patent Application No. PCT/US2024/031875, mailed Oct. 18, 2024 (15 pages).
International Search Report and Written Opinion for PCT/US2024/050660, mailed Nov. 26, 2024 (12 pages).

\* cited by examiner

METHODS OF TREATING CANCERS

SEQUENCE LISTING

The instant application contains a Sequence Listing which has been submitted electronically in ASCII format and is hereby incorporated by reference in its entirety. Said ASCII copy, created on Nov. 5, 2021 is named 51121-049002_Sequence_Listing_9_13_21_ST25 and is 43,669 bytes in size.

BACKGROUND

The invention relates to methods for modulating BRG1- or BRM-associated factors (BAF) complexes for use in the treatment of acute myeloid leukemia (AML). In particular, the invention relates to methods for treatment of disorders associated with BAF complex function.

Chromatin regulation is essential for gene expression, and ATP-dependent chromatin remodeling is a mechanism by which such gene expression occurs. The human Switch/Sucrose Non-Fermentable (SWI/SNF) chromatin remodeling complex, also known as BAF complex, has two SWI2-like ATPases known as BRG1 (Brahma-related gene-1) and BRM (Brahma). The transcription activator BRG1, also known as ATP-dependent chromatin remodeler SMARCA4, is encoded by the SMARCA4 gene on chromosome 19. BRG1 is overexpressed in some cancer tumors and is needed for cancer cell proliferation. BRM, also known as probable global transcription activator SNF2L2 and/or ATP-dependent chromatin remodeler SMARCA2, is encoded by the SMARCA2 gene on chromosome 9 and has been shown to be essential for tumor cell growth in cells characterized by loss of BRG1 function mutations. Deactivation of BRG and/or BRM results in downstream effects in cells, including cell cycle arrest and tumor suppression.

AML is a cancer of the myeloid line of blood cells. AML is characterized by the rapid growth of abnormal cells that build up in the bone marrow and blood and interfere with normal blood cells. AML is generally considered incurable in about 65% of subjects under 60 years old and about 90% of subjects over 60 years old. Typical survival of older subjects with health too poor for intensive chemotherapy is 5- to 10-months. The five-year survival rate for AML is about 25% overall.

SUMMARY OF THE INVENTION

The present invention features methods to treat AML, e.g., in a subject in need thereof.

In one aspect, the invention features a method of treating AML in a subject in need thereof, the method including administering to the subject an effective amount of an agent that reduces the level and/or activity of BRG1 and/or BRM.

In another aspect, the invention features a method of reducing proliferation of AML in a subject in need thereof, the method including administering (e.g., oral administration) to the subject an effective amount of an agent that reduces the level and/or activity of BRG1 and/or BRM in the tumor.

In another aspect, the invention features a method of suppressing metastatic progression of AML in a subject, the method including administering (e.g., oral administration) an effective amount of an agent that reduces the level and/or activity of BRG1 and/or BRM.

In another aspect, the invention features a method of suppressing metastatic colonization of AML in a subject, the method including administering (e.g., oral administration) an effective amount of an agent that reduces the level and/or activity of BRG1 and/or BRM.

In another aspect, the invention features a method of reducing the level and/or activity of BRG1 and/or BRM in an AML cell, the method including contacting the cell with an effective amount of an agent that reduces the level and/or activity of BRG1 and/or BRM in the cell.

In some embodiments of any of the above aspects, the AML cell is in a subject.

In some embodiments of any of the above aspects, the effective amount of the agent reduces the level and/or activity of BRG1 by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference. In some embodiments, the effective amount of the agent that reduces the level and/or activity of BRG1 by at least 50% (e.g., 55%, 60%, 65%, 70%, 75%, 80%, 85%, 90%, or 95%) as compared to a reference. In some embodiments, the effective amount of the agent that reduces the level and/or activity of BRG1 by at least 90% (e.g., 91%, 92%, 93%, 94%, 95%, 96%, 97%, 98%, or 99%).

In some embodiments, the effective amount of the agent reduces the level and/or activity of BRG1 by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 12 hours (e.g., 14 hours, 16 hours, 18 hours, 20 hours, 22 hours, 24 hours, 30 hours, 36 hours, 48 hours, 72 hours, or more). In some embodiments, the effective amount of the agent that reduces the level and/or activity of BRG1 by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 4 days (e.g., 5 days, 6 days, 7 days, 14 days, 28 days, or more).

In some embodiments of any of the above aspects, the effective amount of the agent reduces the level and/or activity of BRM by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference. In some embodiments, the effective amount of the agent that reduces the level and/or activity of BRM by at least 50% (e.g., 55%, 60%, 65%, 70%, 75%, 80%, 85%, 90%, or 95%) as compared to a reference. In some embodiments, the effective amount of the agent that reduces the level and/or activity of BRM by at least 90% (e.g., 91%, 92%, 93%, 94%, 95%, 96%, 97%, 98%, or 99%).

In some embodiments, the effective amount of the agent reduces the level and/or activity of BRM by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 12 hours (e.g., 14 hours, 16 hours, 18 hours, 20 hours, 22 hours, 24 hours, 30 hours, 36 hours, 48 hours, 72 hours, or more). In some embodiments, the effective amount of the agent that reduces the level and/or activity of BRM by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 4 days (e.g., 5 days, 6 days, 7 days, 14 days, 28 days, or more).

In some embodiments, the AML expresses BRG1 and/or BRM protein and/or the cell or subject has been identified as expressing BRG1 and/or BRM. In some embodiments, the AML has an elevated expression of BRG1 and/or BRM. In some embodiments, the AML expresses BRG1 protein and/or the cell or subject has been identified as expressing BRG1. In some embodiments, the AML has an elevated expression of BRG1. In some embodiments, the AML expresses BRM protein and/or the cell or subject has been identified as expressing BRM. In some embodiments, the AML has an elevated expression of BRM.

In some embodiments, the AML is acute promyelocytic leukemia (APL). In some embodiments, the AML arises from a pre-existing myelodysplastic syndrome or myeloproliferative disease. In some embodiments, the AML is treatment-related AML, e.g., AML arising after chemotherapy for another previous malignancy. In some embodiments, the AML is AML with recurrent genetic abnormalities. In some embodiments, the AML is AML with myelodysplasia-related changes. In some embodiments, the AML is therapy-related myeloid neoplasms. In some embodiments, the AML is myeloid sarcoma. In some embodiments, the AML is myeloid proliferations related to Down syndrome. In some embodiments, the AML is blastic plasmacytoid dendritic cell neoplasm. In some embodiments, the AML is AML minimally differentiated. In some embodiments, the AML is AML without maturation. In some embodiments, the AML is AML with granulocytic maturation. In some embodiments, the AML is myelomonocytic together with bone marrow eosinophilia. In some embodiments, the AML is acute monoblastic leukemia. In some embodiments, the AML is acute erythroid leukemia, e.g., erythroleukemia or pure erythroid leukemia. In some embodiments, the AML is acute megakaryoblastic leukemia. In some embodiments, the AML is acute basophilic leukemia.

In some embodiments, the cytogenetics of the AML are t(8;21), t(15;17), or inv(16). In some embodiments the cytogenetics of the AML are normal, +8, +21, +22, del(7q), del(9q), or abnormal 11q23. In some embodiments, the cytogenetics of the AML are −5, −7, del(5q), abnormal 3q, or complex cytogenetics.

In some embodiments, the cancer is metastatic (e.g., the cancer has spread to the liver). The metastatic cancer can include cells exhibiting migration and/or invasion of migrating cells and/or include cells exhibiting endothelial recruitment and/or angiogenesis. In some embodiments, the effective amount of an agent that reduces the level and/or activity of BRG1 and/or BRM is an amount effective to inhibit metastatic colonization of the AML to the liver.

In some embodiments, the AML harbors a DNMT3A mutation. In some embodiments, the AML harbors an FLT3-ITD mutation. In some embodiments, the AML harbors a NPM1 mutation. In some embodiments, the AML harbors a CEBPA mutation (e.g., a biallelic CEBPA mutation). In some embodiments, the AML harbors a c-KIT mutation. In some embodiments, the AML harbors a RUNX1 mutation. In some embodiments, the AML harbors an ASXL1 mutation. In some embodiments, the AML harbors a TP53 mutation. In some embodiments, the AML harbors a DNMT3A mutation. In some embodiments, the AML harbors an IDH1 mutation. In some embodiments, the AML harbors an IDH2 mutation.

In some embodiments, the subject is over 60 years old. In some embodiments, the subject has elevated levels of lactate dehydrogenase.

In some embodiments, the anticancer therapy and the agent that reduces the level and/or activity of BRG1 and/or BRM in a cell are administered within 28 days of each other and each in an amount that together are effective to treat the subject.

In some embodiments, the subject or cancer has and/or has been identified as having a BRG1 loss of function mutation. In some embodiments, the subject or cancer has and/or has been identified as having a BRM loss of function mutation. In some embodiments, the cancer harbors a BRG1 T910M mutation.

In some embodiments, the method further includes administering induction chemotherapy (e.g., cytarabine, an anthracycline such as daunorubicin, arsenic trioxide, all-trans-retinoic acid, or combinations thereof). In some embodiments, the method includes administering a 7-day infusion of cytarabine and a 3-day intravenous push of an anthracycline such as daunorubicin. In some embodiments, the method further includes administering consolidation therapy (e.g., an allogenic stem cell transplantation, immunotherapy such as histamine dihydrochloride and interleukin 2, or combinations thereof. In some embodiments, the method further includes administering a hemapoietic stem cell transplant, gemtuzumab ozogamicin, or combinations thereof. In some embodiments, the method further includes administering venetoclax, gilteritinib, or combinations thereof.

In some embodiments, the cancer is resistant to one or more chemotherapeutic or cytotoxic agents (e.g., the cancer has been determined to be resistant to chemotherapeutic or cytotoxic agents such as by genetic markers, or is likely to be resistant, to chemotherapeutic or cytotoxic agents such as a cancer that has failed to respond to a chemotherapeutic or cytotoxic agent). In some embodiments, the cancer has failed to respond to one or more chemotherapeutic or cytotoxic agents. In some embodiments, the cancer is resistant or has failed to respond to cytarabine, an anthracycline such as daunorubicin, arsenic trioxide, all-trans-retionic acid, histamine dihydrochloride, interleukin 2, gemtuzumab ozogamicin, dacarbazine, temozolomide, cisplatin, treosulfan, fotemustine, IMCgp100, a CTLA-4 inhibitor (e.g., ipilimumab), a PD-1 inhibitor (e.g., Nivolumab or pembrolizumab), a PD-L1 inhibitor (e.g., atezolizumab, avelumab, or durvalumab), a mitogen-activated protein kinase (MEK) inhibitor (e.g., selumetinib, binimetinib, or tametinib), and/or a protein kinase C (PKC) inhibitor (e.g., sotrastaurin or LXS196, also known as IDE196). In some embodiments, the cancer is resistant or has failed to respond to cytarabine, an anthracycline such as daunorubicin, arsenic trioxide, all-trans-retionic acid, histamine dihydrochloride, interleukin 2, and/or gemtuzumab ozogamicin. In some embodiments, the cancer is resistant or has failed to respond to venetoclax, gilteritinib, or combinations thereof.

In some embodiments, the agent that reduces the level and/or activity of BRG1 and/or BRM in a cell is a small molecule compound, an antibody, an enzyme, and/or a polynucleotide.

In some embodiments, the agent that reduces the level and/or activity of BRG1 and/or BRM in a cell is an enzyme, e.g., a clustered regularly interspaced short palindromic repeats (CRISPR)-associated protein such as CRISPR-associated protein 9 (Cas9), CRISPR-associated protein 12a (Cas12a), a zinc finger nuclease (ZFN), a transcription activator-like effector nuclease (TALEN), or a meganuclease.

In some embodiments, the agent that reduces the level and/or activity of BRG1 and/or BRM in a cell is a polynucleotide, e.g., an antisense nucleic acid, a short interfering RNA (siRNA), a short hairpin RNA (shRNA), a microRNA (miRNA), a CRISPR/Cas 9 nucleotide, or a ribozyme.

In some embodiments, the agent that reduces the level and/or activity of BRG1 and/or BRM in a cell is a small molecule compound, e.g., a small molecule BRG1 and/or BRM inhibitor. In some embodiments, the agent that reduces the level and/or activity of BRG1 and/or BRM in a cell is a small molecule compound, e.g., a small molecule BRG1 inhibitor. In some embodiments, the agent that reduces the level and/or activity of BRG1 and/or BRM in a cell is a small molecule compound, e.g., a small molecule BRM inhibitor or a degrader.

In some embodiments, the small molecule BRG1 and/or BRM inhibitor is a compound, or pharmaceutically acceptable salt thereof, having the structure of Formula I:

Formula I

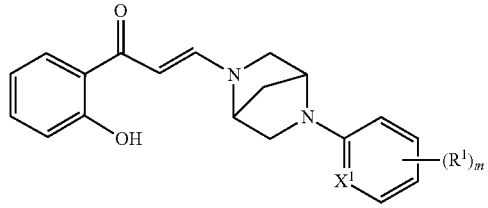

wherein m is 0, 1, 2, 3, or 4; $X^1$ is N or CH; and each $R^1$ is, independently, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino.

In some embodiments, the small molecule BRG1 and/or BRM inhibitor is a compound, or pharmaceutically acceptable salt thereof, having the structure of Formula II:

Formula II

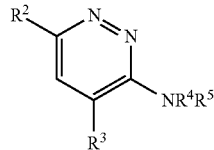

wherein $R^2$ is phenyl that is substituted with hydroxy and that is optionally substituted with one or more groups independently selected from the group consisting of halo, cyano, trifluoromethyl, trifluoromethoxy, $C_{1-3}$ alkyl, and $C_{1-3}$ alkoxy; $R^3$ is selected from the group consisting of —$R^a$, —O—$R^a$, —N($R^a$)$_2$, —S(O)$_2R^a$, and —C(O)—N($R^a$)$_2$; each $R^a$ is, independently, selected from the group consisting of hydrogen, $C_{1-6}$ alkyl, $C_{2-6}$ alkenyl, $C_{2-6}$ alkynyl, 3-15 membered carbocyclyl, and 3-15 membered heterocyclyl, wherein each $C_{1-6}$ alkyl, $C_{2-6}$ alkenyl, $C_{2-6}$ alkynyl, 3-15 membered carbocyclyl, and 3-15 membered heterocyclyl is optionally substituted with one or more groups independently selected from the group consisting of $R^b$, oxo, halo, —NO$_2$, —N($R^b$)$_2$, —CN, —C(O)—N($R^b$)$_2$, —S(O)—N($R^b$)$_2$, —S(O)$_2$—N($R^b$)$_2$, —O—$R^b$, —S—$R^b$, —O—C(O)—$R^b$, —C(O)—$R^b$, —C(O)—O$R^b$, —S(O)—$R^b$, —S(O)$_2$—$R^b$, —N($R^b$)—C(O)—$R^b$, —N($R^b$)—S(O)—$R^b$, —N($R^b$)—C(O)—N($R^b$)$_2$, and —N($R^b$)—S(O)$_2$—$R^b$; each $R^b$ is, independently, selected from the group consisting of hydrogen, $C_{1-6}$ alkyl, $C_{2-6}$ alkenyl, $C_{2-6}$ alkynyl, $C_{1-6}$ alkoxy, 3-15 membered carbocyclyl, and 3-15 membered heterocyclyl, wherein each $C_{1-6}$ alkyl, $C_{2-6}$ alkenyl, $C_{2-6}$ alkynyl, $C_{1-6}$ alkoxy, 3-15 membered carbocyclyl, and 3-15 membered heterocyclyl is optionally substituted with one or more groups independently selected from RC; or two $R^b$ are taken together with the nitrogen to which they are attached to form a heterocyclyl that is optionally substituted with one or more groups independently selected from the group consisting of oxo, halo and $C_{1-3}$ alkyl that is optionally substituted with one or more groups independently selected from the group consisting of oxo and halo; each RC is, independently, selected from the group consisting of oxo, halo, —NO$_2$, —N($R^d$)$_2$, —CN, —C(O)—N($R^d$)$_2$, —S(O)—N($R^d$)$_2$, —S(O)$_2$—N($R^d$)$_2$, —S—$R^d$, —O—C(O)—$R^d$, —C(O)—$R^d$, —C(O)—$R^d$, —C(O)—O$R^d$, —S(O)—$R^d$, —S(O)$_2$—$R^d$, —N($R^d$)—C(O)—$R^d$, —N($R^d$)—S(O)—$R^d$, —N($R^d$)—C(O)—N($R^d$)$_2$, —N($R^d$)—S(O)$_2$—$R^d$, $C_{1-6}$ alkyl, $C_{2-6}$ alkenyl, $C_{2-6}$ alkynyl, 3-15 membered carbocyclyl, and 3-15 membered heterocyclyl, wherein any $C_{1-6}$ alkyl, $C_{2-6}$ alkenyl, $C_{2-6}$ alkynyl, 3-15 membered carbocyclyl, and 3-15 membered heterocyclyl is optionally substituted with one or more groups independently selected from the group consisting of $R^d$, oxo, halo, —NO$_2$, —N($R^d$)$_2$, —CN, —C(O)—N($R^d$)$_2$, —S(O)—N($R^d$)$_2$, —S(O)$_2$—N($R^d$)$_2$, —O—$R^d$, —S—$R^d$, —O—C(O)—$R^d$, —C(O)—$R^d$, —C(O)—$R^d$, —S(O)—$R^d$, —S(O)$_2$—$R^d$, —N($R^d$)—C(O)—$R^d$, —N($R^d$)—S(O)—$R^d$, —N($R^d$)—C(O)—N($R^d$)$_2$, and —N($R^d$)—S(O)$_2$—$R^d$; each $R^d$ is, independently, selected from the group consisting of hydrogen, $C_{1-6}$ alkyl, $C_{2-6}$ alkenyl, $C_{2-6}$ alkynyl, carbocyclyl, and carbocyclyl($C_{1-3}$ alkyl)-; $R^4$ is H, $C_{1-6}$ alkyl, or —C(=O)—$C_{1-6}$ alkyl; and $R^5$ is H or $C_{1-6}$ alkyl.

Compounds of Formula II may be synthesized by methods known in the art, e.g., those described in U.S. Patent Publication No. 2018/0086720, the synthetic methods of which are incorporated by reference.

In some embodiments, the small molecule BRG1 and/or BRM inhibitor is a compound, or pharmaceutically acceptable salt thereof, having the structure of Formula III:

Formula III

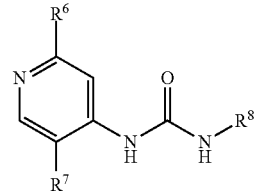

wherein $R^6$ is halo, e.g., fluoro or chloro; $R^7$ is hydrogen, optionally substituted amino, or optionally substituted $C_{1-6}$ alkyl; and $R^8$ is optionally substituted $C_{6-10}$ aryl or optionally substituted $C_{2-9}$ heteroaryl.

In some embodiments, the small molecule BRG1 and/or BRM inhibitor is a compound, or pharmaceutically acceptable salt thereof, having the structure of any one of compounds 1-16:

1

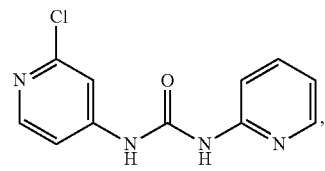

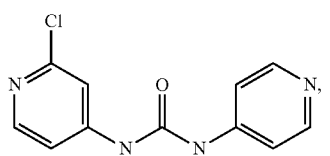
1
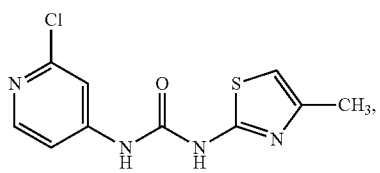
2
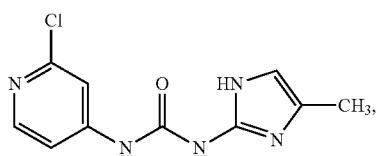
3
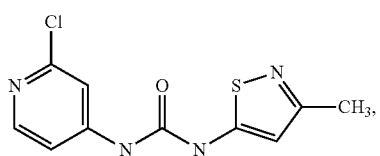
4
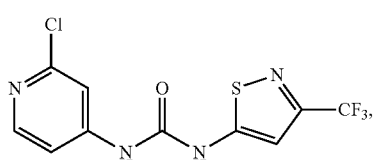
5
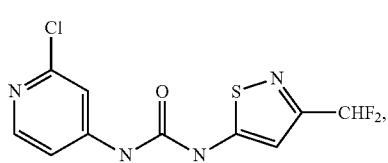
6
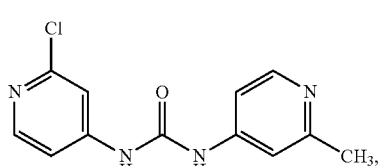
7
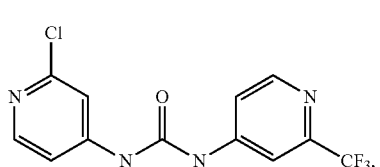
8
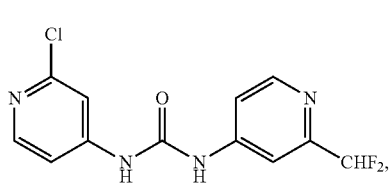
9
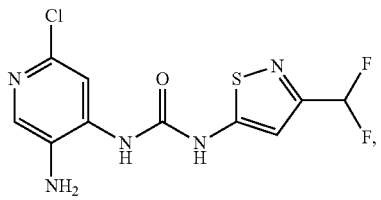
10
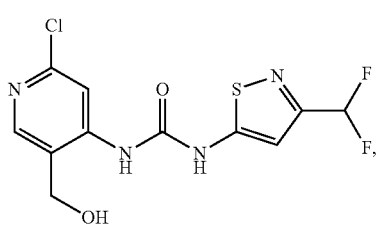
11
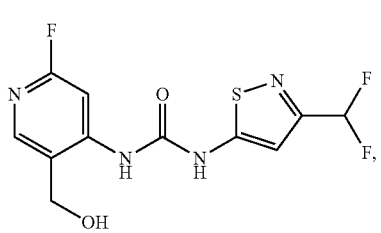
12
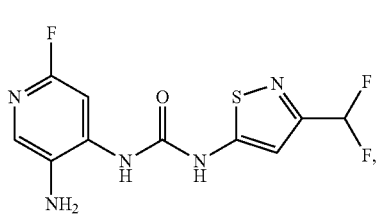
13
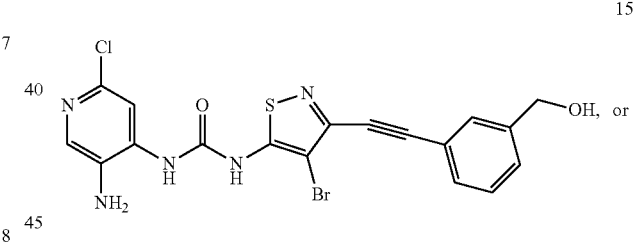
14
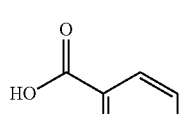
15, or
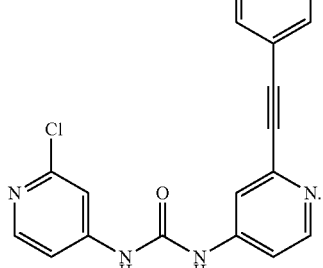
16
In some embodiments, the small molecule BRG1 and/or BRM inhibitor is a compound, or pharmaceutically acceptable salt thereof, having the structure of Formula IV:

Formula IV

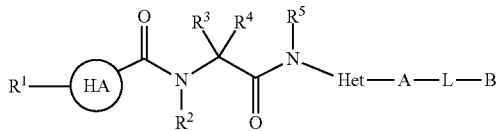

wherein $R^1$ is absent, H, optionally substituted $C_1$-$C_6$ acyl, optionally substituted $C_1$-$C_6$ alkyl, optionally substituted $C_3$-$C_8$ cycloalkyl, optionally substituted $C_1$-$C_6$ heteroalkyl, optionally substituted $C_2$-$C_9$ heterocyclyl, or —SO$_2$R$^6$;

is 5- or 6-membered heteroarylene; each of $R^2$ and $R^5$ is, independently, H or optionally substituted $C_1$-$C_6$ alkyl; $R^3$ is H or optionally substituted $C_1$-$C_6$ alkyl; and $R^4$ is H, optionally substituted $C_1$-$C_6$ alkyl, or optionally substituted $C_1$-$C_6$ heteroalkyl; or $R^3$ and $R^4$, together with the carbon atom to which each is attached, form an optionally substituted $C_3$-$C_6$ cycloalkyl; $R^6$ is optionally substituted $C_1$-$C_6$ alkyl or —NR$^7$R$^8$; $R^7$ and $R^8$ are, independently, optionally substituted $C_1$-$C_6$ alkyl; Het is optionally substituted 5-membered heteroarylene, optionally substituted 6-membered heteroarylene, or

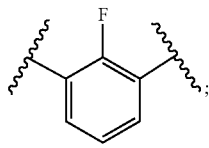 [SMILES: *c1cccc(*)c1F]

A is optionally substituted $C_6$-$C_{10}$ arylene, optionally substituted $C_2$-$C_9$ heterocyclylene, or optionally substituted $C_2$-$C_9$ heteroarylene; L is absent, —O—, optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted $C_2$-$C_9$ heterocyclylene, optionally substituted $C_2$-$C_9$ heterocyclyl $C_1$-$C_6$ alkylene, optionally substituted $C_2$-$C_9$ heteroarylene, or optionally substituted $C_2$-$C_9$ heteroaryl $C_1$-$C_6$ alkylene; and B is H, halogen, cyano, optionally substituted $C_6$-$C_{10}$ aryl, optionally substituted $C_3$-$C_{10}$ cycloalkyl, optionally substituted $C_2$-$C_9$ heterocyclyl, or optionally substituted $C_2$-$C_9$ heteroaryl, or a pharmaceutically acceptable salt thereof.

In some embodiments,

is 6-membered heteroarylene. In some embodiments,

is 5-membered heteroarylene.

In some embodiments,

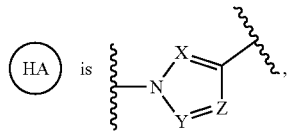

where each of X, Y, and Z is, independently, N or CH.

In some embodiments, the compound of Formula IV has the structure of Formula IVa:

Formula IVa

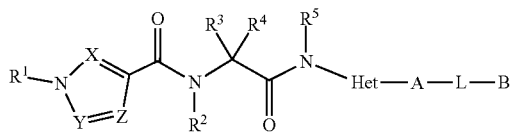

wherein each of X, Y, and Z is, independently, N or CH; $R^1$ is H, optionally substituted $C_1$-$C_6$ acyl, optionally substituted $C_1$-$C_6$ alkyl, optionally substituted $C_1$-$C_6$ heteroalkyl, optionally substituted $C_3$-$C_8$ cycloalkyl, optionally substituted $C_2$-$C_9$ heterocyclyl, or —SO$_2$R$^6$; each of $R^2$, $R^3$, and $R^5$ is, independently, H or optionally substituted $C_1$-$C_6$ alkyl; $R^4$ is H, optionally substituted $C_1$-$C_6$ alkyl, or optionally substituted $C_1$-$C_6$ heteroalkyl; $R^6$ is optionally substituted $C_1$-$C_6$ alkyl or —NR$^7$R$^8$; each of $R^7$ and $R^8$ is, independently, optionally substituted $C_1$-$C_6$ alkyl; Het is optionally substituted 5-membered heteroarylene, optionally substituted 6-membered heteroarylene, or

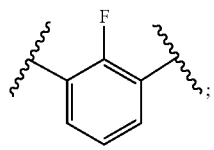

A is optionally substituted $C_6$-$C_{10}$ arylene, optionally substituted $C_2$-$C_9$ heterocyclylene, or optionally substituted $C_2$-$C_9$ heteroarylene; L is absent, —O—, optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted $C_2$-$C_9$ heterocyclylene, optionally substituted $C_2$-$C_9$ heterocyclyl $C_1$-$C_6$ alkylene, optionally substituted $C_2$-$C_9$ heteroarylene, or optionally substituted $C_2$-$C_9$ heteroaryl $C_1$-$C_6$ alkylene; and B is H, halogen, cyano, optionally substituted $C_6$-$C_{10}$ aryl, optionally substituted $C_3$-$C_{10}$ cycloalkyl, optionally substituted $C_2$-$C_9$ heterocyclyl, or optionally substituted $C_2$-$C_9$ heteroaryl, or a pharmaceutically acceptable salt thereof.

In some embodiments, X, Y, and Z are CH; X is N and Y and Z are CH; Z is N and X and Y are CH; Y is N and X and Z are CH; X is CH and Y and Z are N; Z is CH and X and y are N; Y is CH and X and Z are N; or X, Y, and Z are N.

In some embodiments, the compound of Formula IV has the structure of Formula IVb:

Formula IVb

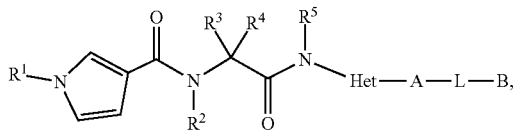

or a pharmaceutically acceptable salt thereof.

In some embodiments, the compound of Formula IV has the structure of Formula IVc:

Formula IVc

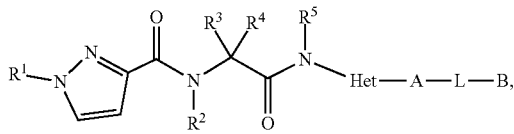

or a pharmaceutically acceptable salt thereof.

In some embodiments, the compound of Formula IV has the structure of Formula Ic:

Formula IVd

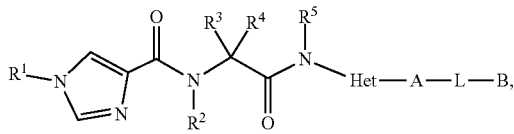

or a pharmaceutically acceptable salt thereof.

In some embodiments, the compound of Formula IV has the structure of Formula IVe:

Formula IVe

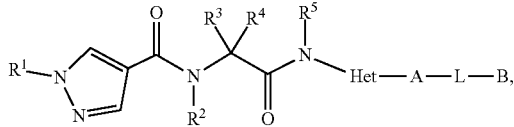

or a pharmaceutically acceptable salt thereof.

In some embodiments,

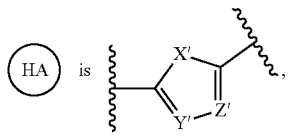

where X' is O or S; Y' is N or CH; and Z' is N or CH.

In some embodiments, the compound of Formula IVa has the structure of Formula V:

Formula V

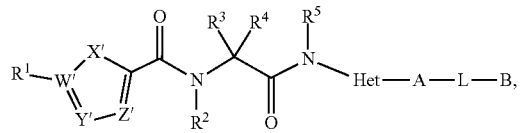

wherein W is C or N; X' is O, S, or N—CH$_3$; Y' is N or CH; Z' is N or CH; R$^1$ is absent, H, optionally substituted C$_1$-C$_6$ acyl, optionally substituted C$_1$-C$_6$ alkyl, optionally substituted C$_1$-C$_6$ heteroalkyl, optionally substituted C$_3$-C$_8$ cycloalkyl, optionally substituted C$_2$-C$_9$ heterocyclyl, or —SO$_2$R$^6$; each of R$^2$, R$^3$, and R$^5$ is, independently, H or optionally substituted C$_1$-C$_6$ alkyl; R$^4$ is H, optionally substituted C$_1$-C$_6$ alkyl, or optionally substituted C$_1$-C$_6$ heteroalkyl; R$^6$ is optionally substituted C$_1$-C$_6$ alkyl or —NR$^7$R$^8$; each of R$^7$ and R$^8$ is, independently, optionally substituted C$_1$-C$_6$ alkyl; Het is optionally substituted 5-membered heteroarylene, optionally substituted 6-membered heteroarylene, or

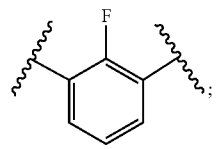 [SMILES: *c1cccc(*)c1F]

A is optionally substituted C$_6$-C$_{10}$ arylene, optionally substituted C$_2$-C$_9$ heterocyclylene, or optionally substituted C$_2$-C$_9$ heteroarylene; L is absent, —O—, optionally substituted C$_1$-C$_6$ alkylene, optionally substituted C$_1$-C$_6$ heteroalkylene, optionally substituted C$_1$-C$_6$ alkenylene, optionally substituted C$_2$-C$_6$ heteroalkenylene, optionally substituted C$_2$-C$_6$ alkynylene, optionally substituted C$_2$-C$_6$ heteroalkynylene, optionally substituted C$_2$-C$_9$ heterocyclylene, optionally substituted C$_2$-C$_9$ heterocyclyl C$_1$-C$_6$ alkylene, optionally substituted C$_2$-C$_9$ heteroarylene, or optionally substituted C$_2$-C$_9$ heteroaryl C$_1$-C$_6$ alkylene; and B is H, halogen, cyano, optionally substituted C$_6$-C$_{10}$ aryl, optionally substituted C$_3$-C$_{10}$ cycloalkyl, optionally substituted C$_2$-C$_9$ heterocyclyl, or optionally substituted C$_2$-C$_9$ heteroaryl, or a pharmaceutically acceptable salt thereof.

In some embodiments, X' is O, Y' is CH, and Z' is N; X' is S, Y' is CH, and Z' is N; X' is O, Y' is N, and Z' is CH; X' is S, Y' is N, and Z' is CH; X' is O, Y' is N, and Z' is N; or X' is S, Y' is N, and Z' is N.

In some embodiments, the compound of Formula V has the structure of Formula Va:

Formula Va

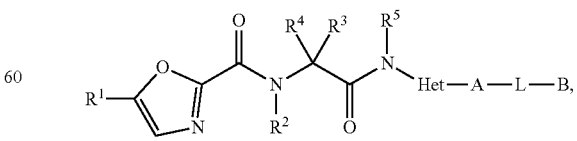

or a pharmaceutically acceptable salt thereof.

In some embodiments, the compound of Formula II has the structure of Formula Vb:

Formula Vb

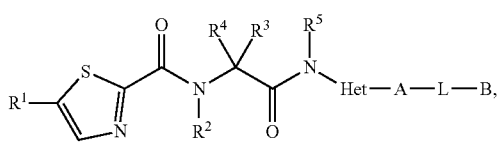

or a pharmaceutically acceptable salt thereof.

In some embodiments, the small molecule compound, or pharmaceutically acceptable salt thereof is any one of compounds 17-20 having the structure:

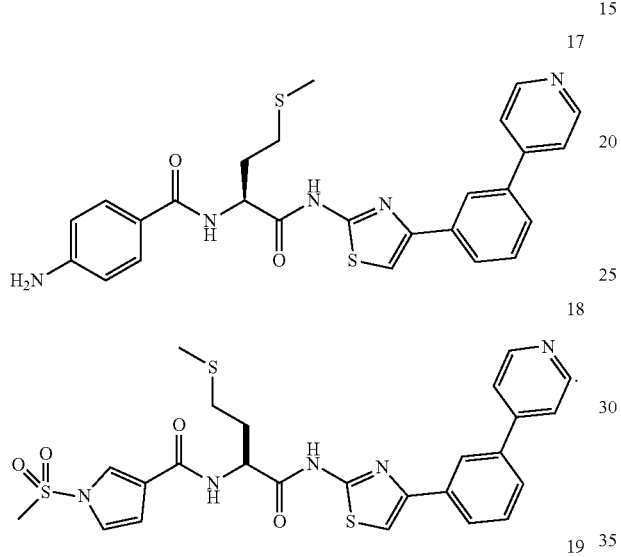

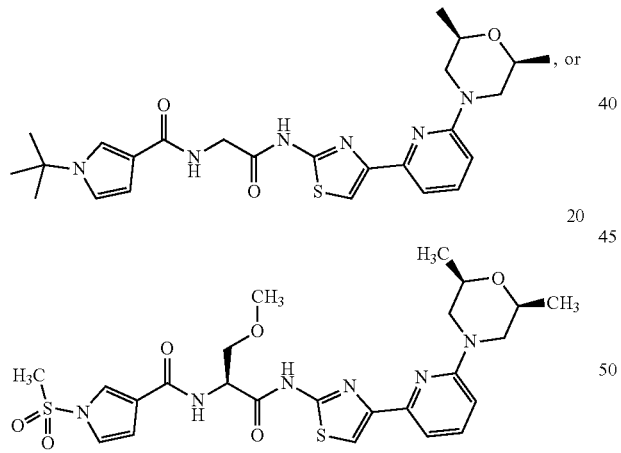

In some embodiments, the small molecule compound, or a pharmaceutically acceptable salt thereof is a degrader. In some embodiments, the degrader has the structure of Formula VI:

C-L-D    Formula VI wherein C is a BRG1 and/or BRM binding moiety; L is a linker; and D is a degradation moiety, or a pharmaceutically acceptable salt thereof. In some embodiments, the degradation moiety is a ubiquitin ligase moiety. In some embodiments, the ubiquitin ligase binding moiety includes Cereblon ligands, IAP (Inhibitors of Apoptosis) ligands, mouse double minute 2 homolog (MDM2), hydrophobic tag, or von Hippel-Lindau ligands, or derivatives or analogs thereof.

In some embodiments, A includes the structure of any one of Formula I-V, or any one of compounds 1-20.

In some embodiments, the hydrophobic tag includes a diphenylmethane, adamantine, or tri-Boc arginine, i.e., the hydrophobic tag includes the structure:

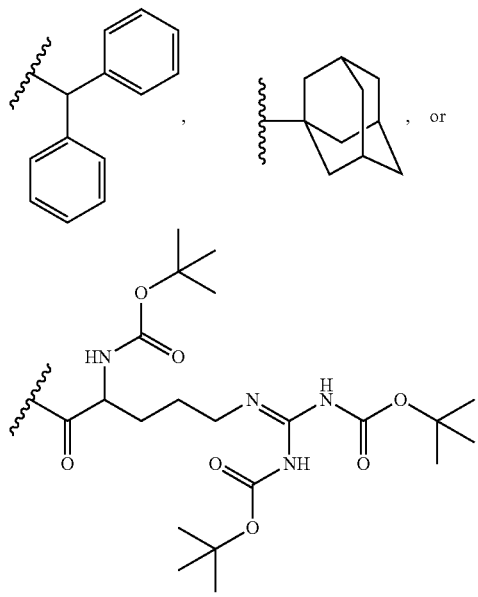

In some embodiments, the ubiquitin ligase binding moiety includes the structure of Formula A:

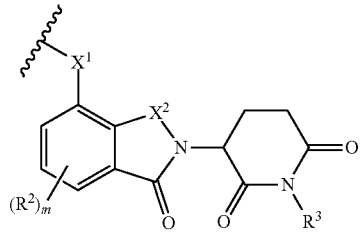

Formula A wherein $X^1$ is $CH_2$, O, S, or $NR^1$, wherein $R^1$ is H, optionally substituted $C_1$-$C_6$ alkyl, or optionally substituted $C_1$-$C_6$ heteroalkyl; $X^2$ is C=O, $CH_2$, or

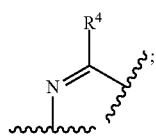

$R^3$ and $R^4$ are, independently, H, optionally substituted $C_1$-$C_6$ alkyl, or optionally substituted $C_1$-$C_6$ heteroalkyl; m is 0, 1, 2, 3, or 4; and each $R^2$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino, or a pharmaceutically acceptable salt thereof.

In some embodiments, the ubiquitin ligase binding moiety includes the structure:

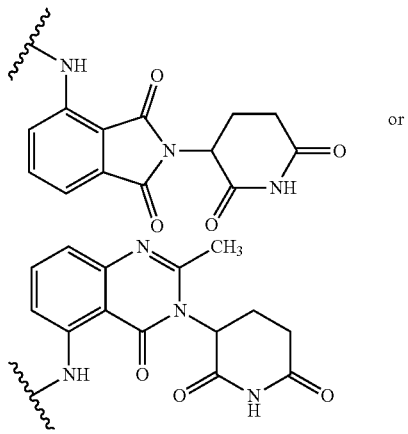

or is a derivative or an analog thereof, or a pharmaceutically acceptable salt thereof.

In some embodiments, the ubiquitin ligase binding moiety includes the structure of Formula B:

Formula B

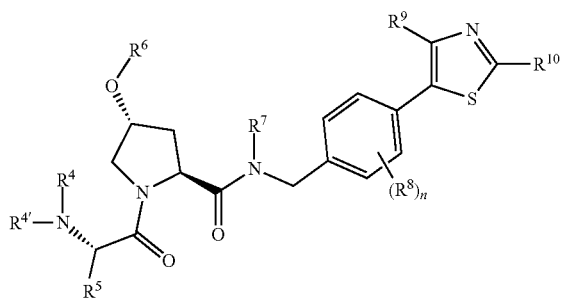

wherein each $R^4$, $R^{4'}$, and $R^7$ is, independently, H, optionally substituted $C_1$-$C_6$ alkyl, or optionally substituted $C_1$-$C_6$ heteroalkyl; $R^5$ is optionally substituted $C_1$-$C_6$ alkyl, optionally substituted $C_1$-$C_6$ heteroalkyl, optionally substituted $C_3$-$C_{10}$ carbocyclyl, optionally substituted $C_6$-$C_{10}$ aryl, optionally substituted $C_1$-$C_6$ alkyl $C_3$-$C_{10}$ carbocyclyl, or optionally substituted $C_1$-$C_6$ alkyl $C_6$-$C_{10}$ aryl; $R^6$ is H, optionally substituted $C_1$-$C_6$ alkyl, optionally substituted $C_3$-$C_{10}$ carbocyclyl, optionally substituted $C_6$-$C_{10}$ aryl, optionally substituted $C_1$-$C_6$ alkyl $C_3$-$C_{10}$ carbocyclyl, or optionally substituted $C_1$-$C_6$ alkyl $C_6$-$C_{10}$ aryl; n is 0, 1, 2, 3, or 4; each $R^8$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino; and each $R^9$ and $R^{10}$ is, independently, H, halogen, optionally substituted $C_1$-$C_6$ alkyl, or optionally substituted $C_6$-$C_{10}$ aryl, wherein $R^{4'}$ or $R^5$ includes a bond to the linker, or a pharmaceutically acceptable salt thereof.

In some embodiments, the ubiquitin ligase binding moiety includes the structure:

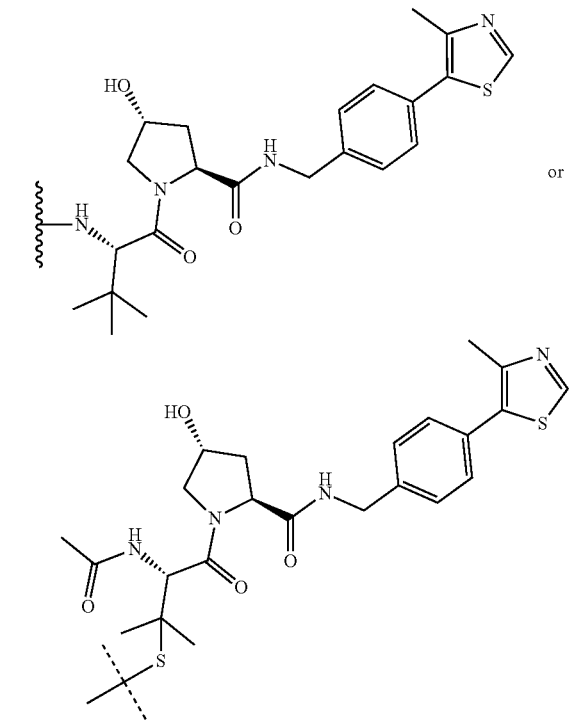

or is a derivative or analog thereof, or a pharmaceutically acceptable salt thereof.

In some embodiments, the ubiquitin ligase binding moiety includes the structure of Formula C:

Formula C

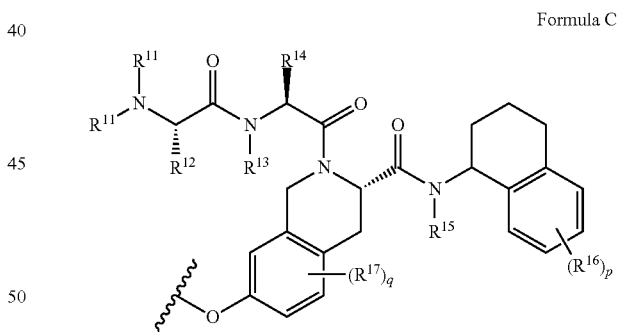

wherein each $R^{11}$, $R^{13}$, and $R^{15}$ is, independently, H, optionally substituted $C_1$-$C_6$ alkyl, or optionally substituted $C_1$-$C_6$ heteroalkyl; $R^{12}$ is optionally substituted $C_1$-$C_6$ alkyl, optionally substituted $C_3$-$C_{10}$ carbocyclyl, optionally substituted $C_6$-$C_{10}$ aryl, optionally substituted $C_1$-$C_6$ alkyl $C_3$-$C_{10}$ carbocyclyl, or optionally substituted $C_1$-$C_6$ alkyl $C_6$-$C_{10}$ aryl; $R^{14}$ is optionally substituted $C_1$-$C_6$ alkyl, optionally substituted $C_3$-$C_{10}$ carbocyclyl, optionally substituted $C_6$-$C_{10}$ aryl, optionally substituted $C_1$-$C_6$ alkyl $C_3$-$C_{10}$ carbocyclyl, or optionally substituted $C_1$-$C_6$ alkyl $C_6$-$C_{10}$ aryl; p is 0, 1, 2, 3, or 4; each $R^{16}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino; q is 0, 1, 2, 3, or 4; and each $R^{17}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino, or a pharmaceutically acceptable salt thereof.

In some embodiments, the ubiquitin ligase binding moiety includes the structure:

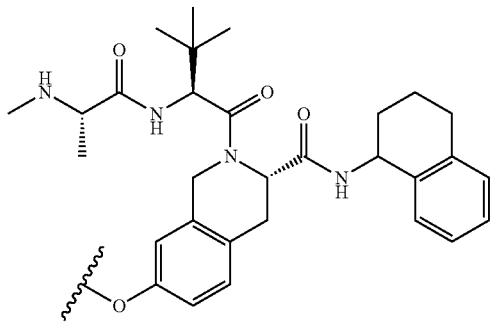 [SMILES: *Oc1ccc2c(c1)CN(C(=O)[C@@H](NC(=O)[C@H](C)NC)C(C)(C)C)[C@H](C(=O)NC1CCCc3ccccc31)C2]

or is a derivative or an analog thereof, or a pharmaceutically acceptable salt thereof.

In some embodiments, the ubiquitin ligase binding moiety includes the structure of Formula D:

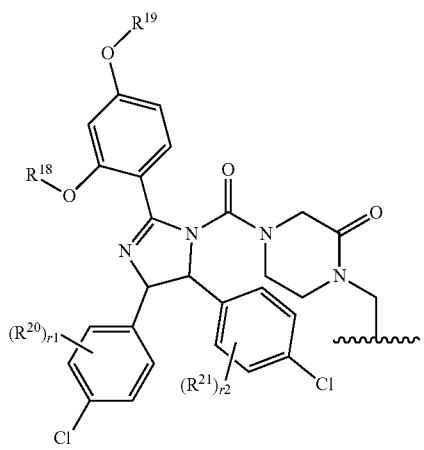

Formula D wherein each $R^{18}$ and $R^{19}$ is, independently, H, optionally substituted $C_1$-$C_6$ alkyl, optionally substituted $C_3$-$C_{10}$ carbocyclyl, optionally substituted $C_6$-$C_{10}$ aryl, optionally substituted $C_1$-$C_6$ alkyl $C_3$-$C_{10}$ carbocyclyl, or optionally substituted $C_1$-$C_6$ alkyl $C_6$-$C_{10}$ aryl; r1 is 0, 1, 2, 3, or 4; each $R^{20}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino; r2 is 0, 1, 2, 3, or 4; and each $R^{21}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino, or a pharmaceutically acceptable salt thereof.

In some embodiments, the ubiquitin ligase binding moiety includes the structure:

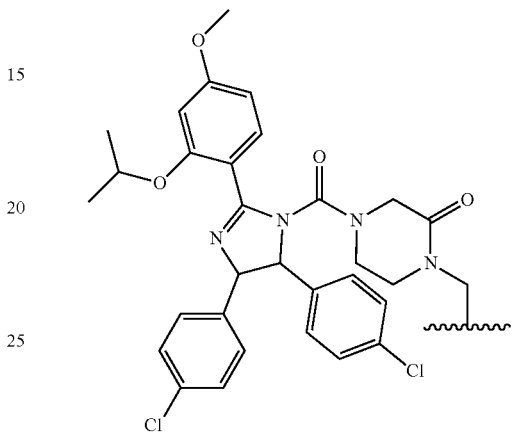

or is a derivative or an analog thereof, or a pharmaceutically acceptable salt thereof.

In some embodiments, the linker has the structure of Formula V:

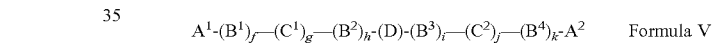

Formula V wherein $A^1$ is a bond between the linker and A; $A^2$ is a bond between B and the linker; $B^1$, $B^2$, $B^3$, and $B^4$ each, independently, is selected from optionally substituted $C_1$-$C_2$ alkyl, optionally substituted $C_1$-$C_3$ heteroalkyl, O, S, $S(O)_2$, and $NR^N$; $R^N$ is hydrogen, optionally substituted $C_{1-4}$ alkyl, optionally substituted $C_{2-4}$ alkenyl, optionally substituted $C_{2-4}$ alkynyl, optionally substituted $C_{2-6}$ heterocyclyl, optionally substituted $C_{6-12}$ aryl, or optionally substituted $C_{1-7}$ heteroalkyl; $C^1$ and $C^2$ are each, independently, selected from carbonyl, thiocarbonyl, sulphonyl, or phosphoryl; f, g, h, l, j, and k are each, independently, 0 or 1; and D is optionally substituted $C_{1-10}$ alkyl, optionally substituted $C_{2-10}$ alkenyl, optionally substituted $C_{2-10}$ alkynyl, optionally substituted $C_{2-6}$ heterocyclyl, optionally substituted $C_{6-12}$ aryl, optionally substituted $C_2$-$C_{10}$ polyethylene glycol, or optionally substituted $C_{1-10}$ heteroalkyl, or a chemical bond linking $A^1$-$(B^1)_f$—$(C^1)_g$—$(B^2)_h$— to —$(B^3)_i$—$(C^2)_j$—$(B^4)_k$-$A^2$.

In some embodiments, D is optionally substituted $C_2$-$C_{10}$ polyethylene glycol. In some embodiments, $C^1$ and $C^2$ are each, independently, a carbonyl or sulfonyl. In some embodiments, $B^1$, $B^2$, $B^3$, and $B^4$ each, independently, is selected from optionally substituted $C_1$-$C_2$ alkyl, optionally substituted $C_1$-$C_3$ heteroalkyl, O, S, $S(O)_2$, and $NR^N$; $R^N$ is hydrogen or optionally substituted $C_{1-4}$ alkyl. In some embodiments, $B^1$, $B^2$, $B^3$, and $B^4$ each, independently, is selected from optionally substituted $C_1$-$C_2$ alkyl or optionally substituted $C_1$-$C_3$ heteroalkyl. In some embodiments, j is 0. In some embodiments, k is 0. In some embodiments, j and k are each, independently, 0. In some embodiments, f, g, h, and i are each, independently, 1.

In some embodiments, the linker of Formula VII has the structure of Formula VIIa:

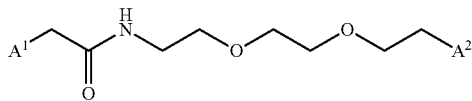

Formula VIIa wherein $A^1$ is a bond between the linker and A, and $A^2$ is a bond between B and the linker.

In some embodiments, D is optionally substituted $C_{1-10}$ alkyl. In some embodiments, $C^1$ and $C^2$ are each, independently, a carbonyl. In some embodiments, $B^1$, $B^2$, $B^3$, and $B^4$ each, independently, is selected from optionally substituted $C_1$-$C_2$ alkyl, optionally substituted $C_1$-$C_3$ heteroalkyl, O, S, $S(O)_2$, and $NR^N$, wherein $R^N$ is hydrogen or optionally substituted $C_{1-4}$ alkyl. In some embodiments, $B^1$, $B^2$, $B^3$, and $B^4$ each, independently, is selected from optionally substituted $C_1$-$C_2$ alkyl, O, S, $S(O)_2$, and $NR^N$, wherein $R^N$ is hydrogen or optionally substituted $C_{1-4}$ alkyl. In some embodiments, $B^1$ and $B^4$ each, independently, is optionally substituted $C_1$-$C_2$ alkyl. In some embodiments, $B^1$ and $B^4$ each, independently, is $C_1$ alkyl. In some embodiments, $B^2$ and $B^4$ each, independently, is $NR^N$, wherein $R^N$ is hydrogen or optionally substituted $C_{1-4}$ alkyl. In some embodiments, $B^2$ and $B^4$ each, independently, is NH. In some embodiments, f, g, h, l, j, and k are each, independently, 1.

In some embodiments, the linker of Formula VII has the structure of Formula VIIb:

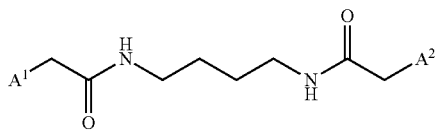

Formula VIIb wherein $A^1$ is a bond between the linker and A, and $A^2$ is a bond between B and the linker.

Chemical Terms

For any of the following chemical definitions, a number following an atomic symbol indicates that total number of atoms of that element that are present in a particular chemical moiety. As will be understood, other atoms, such as hydrogen atoms, or substituent groups, as described herein, may be present, as necessary, to satisfy the valences of the atoms. For example, an unsubstituted $C_2$ alkyl group has the formula —$CH_2CH_3$. When used with the groups defined herein, a reference to the number of carbon atoms includes the divalent carbon in acetal and ketal groups but does not include the carbonyl carbon in acyl, ester, carbonate, or carbamate groups. A reference to the number of oxygen, nitrogen, or sulfur atoms in a heteroaryl group only includes those atoms that form a part of a heterocyclic ring.

The term "acyl," as used herein, represents a hydrogen or an alkyl group that is attached to a parent molecular group through a carbonyl group, as defined herein, and is exemplified by formyl (i.e., a carboxyaldehyde group), acetyl, trifluoroacetyl, propionyl, and butanoyl. Exemplary unsubstituted acyl groups include from 1 to 6, from 1 to 11, or from 1 to 21 carbons.

The term "alkyl," as used herein, refers to a branched or straight-chain monovalent saturated aliphatic hydrocarbon radical of 1 to 20 carbon atoms (e.g., 1 to 16 carbon atoms, 1 to 10 carbon atoms, or 1 to 6 carbon atoms).

An alkylene is a divalent alkyl group. The term "alkenyl," as used herein, alone or in combination with other groups, refers to a straight chain or branched hydrocarbon residue having a carbon-carbon double bond and having 2 to 20 carbon atoms (e.g., 2 to 16 carbon atoms, 2 to 10 carbon atoms, 2 to 6, or 2 carbon atoms).

The term "alkynyl," as used herein, alone or in combination with other groups, refers to a straight chain or branched hydrocarbon residue having a carbon-carbon triple bond and having 2 to 20 carbon atoms (e.g., 2 to 16 carbon atoms, 2 to 10 carbon atoms, 2 to 6, or 2 carbon atoms).

The term "amino," as used herein, represents —$N(R^{N}1)_2$, wherein each $R^{N}1$ is, independently, H, OH, $NO_2$, $N(R^{N2})_2$, $SO_2OR^{N2}$, $SO_2R^{N2}$, $SOR^{N2}$, an N-protecting group, alkyl, alkoxy, aryl, arylalkyl, cycloalkyl, acyl (e.g., acetyl, trifluoroacetyl, or others described herein), wherein each of these recited $R^{N}1$ groups can be optionally substituted; or two $R^{N}1$ combine to form an alkylene or heteroalkylene, and wherein each $R^{N2}$ is, independently, H, alkyl, or aryl. The amino groups of the compounds described herein can be an unsubstituted amino (i.e., —$NH_2$) or a substituted amino (i.e., —$N(R^{N1})_2$).

The term "aryl," as used herein, refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthyl, 1,2-dihydronaphthyl, indanyl, and 1H-indenyl.

The term "arylalkyl," as used herein, represents an alkyl group substituted with an aryl group. Exemplary unsubstituted arylalkyl groups are from 7 to 30 carbons (e.g., from 7 to 16 or from 7 to 20 carbons, such as $C_1$-$C_6$ alkyl $C_6$-$C_{10}$ aryl, $C_1$-$C_{10}$ alkyl $C_6$-$C_{10}$ aryl, or $C_1$-$C_{20}$ alkyl $C_6$-$C_{10}$ aryl), such as, benzyl and phenethyl. In some embodiments, the alkyl and the aryl each can be further substituted with 1, 2, 3, or 4 substituent groups as defined herein for the respective groups.

The term "azido," as used herein, represents a —N3 group.

The term "bridged polycycloalkyl," as used herein, refers to a bridged polycyclic group of 5 to 20 carbons, containing from 1 to 3 bridges.

The term "cyano," as used herein, represents a —CN group.

The term "carbocyclyl," as used herein, refers to a non-aromatic $C_3$-$C_{12}$ monocyclic, bicyclic, or tricyclic structure in which the rings are formed by carbon atoms. Carbocyclyl structures include cycloalkyl groups and unsaturated carbocyclyl radicals.

The term "cycloalkyl," as used herein, refers to a saturated, non-aromatic, monovalent mono- or polycarbocyclic radical of 3 to 10, preferably 3 to 6 carbon atoms. This term is further exemplified by radicals such as cyclopropyl, cyclobutyl, cyclopentyl, cyclohexyl, cycloheptyl, norbornyl, and adamantyl.

The term "halogen," as used herein, means a fluorine (fluoro), chlorine (chloro), bromine (bromo), or iodine (iodo) radical.

The term "heteroalkyl," as used herein, refers to an alkyl group, as defined herein, in which one or more of the constituent carbon atoms have been replaced by nitrogen, oxygen, or sulfur. In some embodiments, the heteroalkyl group can be further substituted with 1, 2, 3, or 4 substituent groups as described herein for alkyl groups. An example of a heteroalkyl group is an "alkoxy", which, as used herein, refers alkyl-O— (e.g., methoxy and ethoxy). A heteroalkylene is a divalent heteroalkyl group. The term "heteroalkenyl," as used herein, refers to an alkenyl group, as defined herein, in which one or more of the constituent carbon atoms have been replaced by nitrogen, oxygen, or sulfur. In some embodiments, the heteroalkenyl group can be further substituted with 1, 2, 3, or 4 substituent groups as described herein for alkenyl groups. Examples of heteroalkenyl groups are an "alkenoxy" which, as used herein, refers alkenyl-O—. A heteroalkenylene is a divalent heteroalkenyl group. The term "heteroalkynyl," as used herein, refers to an alkynyl group, as defined herein, in which one or more of the constituent carbon atoms have been replaced by nitrogen, oxygen, or sulfur. In some embodiments, the heteroalkynyl group can be further substituted with 1, 2, 3, or 4 substituent groups as described herein for alkynyl groups. Examples of heteroalkynyl groups are an "alkynoxy" which, as used herein, refers alkynyl-O—. A heteroalkynylene is a divalent heteroalkynyl group.

The term "heteroaryl," as used herein, refers to an aromatic mono- or polycyclic radical of 5 to 12 atoms having at least one aromatic ring containing 1, 2, or 3 ring atoms selected from nitrogen, oxygen, and sulfur, with the remaining ring atoms being carbon. One or two ring carbon atoms of the heteroaryl group may be replaced with a carbonyl group. Examples of heteroaryl groups are pyridyl, pyrazoyl, benzooxazolyl, benzoimidazolyl, benzothiazolyl, imidazolyl, oxaolyl, and thiazolyl.

The term "heteroarylalkyl," as used herein, represents an alkyl group substituted with a heteroaryl group. Exemplary unsubstituted heteroarylalkyl groups are from 7 to 30 carbons (e.g., from 7 to 16 or from 7 to 20 carbons, such as $C_1$-$C_6$ alkyl $C_2$-$C_9$ heteroaryl, $C_1$-$C_{10}$ alkyl $C_2$-$C_9$ heteroaryl, or $C_1$-$C_{20}$ alkyl $C_2$-$C_9$ heteroaryl). In some embodiments, the alkyl and the heteroaryl each can be further substituted with 1, 2, 3, or 4 substituent groups as defined herein for the respective groups.

The term "heterocyclyl," as used herein, refers a mono- or polycyclic radical having 3 to 12 atoms having at least one ring containing 1, 2, 3, or 4 ring atoms selected from N, O or S, wherein no ring is aromatic. Examples of heterocyclyl groups include, but are not limited to, morpholinyl, thiomorpholinyl, furyl, piperazinyl, piperidinyl, pyranyl, pyrrolidinyl, tetrahydropyranyl, tetrahydrofuranyl, and 1,3-dioxanyl.

The term "heterocyclylalkyl," as used herein, represents an alkyl group substituted with a heterocyclyl group. Exemplary unsubstituted heterocyclylalkyl groups are from 7 to 30 carbons (e.g., from 7 to 16 or from 7 to 20 carbons, such as $C_1$-$C_6$ alkyl $C_2$-$C_9$ heterocyclyl, $C_1$-$C_{10}$ alkyl $C_2$-$C_9$ heterocyclyl, or $C_1$-$C_{20}$ alkyl $C_2$-$C_9$ heterocyclyl). In some embodiments, the alkyl and the heterocyclyl each can be further substituted with 1, 2, 3, or 4 substituent groups as defined herein for the respective groups.

The term "hydroxyalkyl," as used herein, represents alkyl group substituted with an —OH group.

The term "hydroxyl," as used herein, represents an —OH group.

The term "N-protecting group," as used herein, represents those groups intended to protect an amino group against undesirable reactions during synthetic procedures. Commonly used N-protecting groups are disclosed in Greene, "Protective Groups in Organic Synthesis," 3rd Edition (John Wiley & Sons, New York, 1999). N-protecting groups include, but are not limited to, acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L, or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-20 dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, arylalkyl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —$NO_2$ group.

The term "thiol," as used herein, represents an —SH group.

The alkyl, alkenyl, alkynyl, heteroalkyl, heteroalkenyl, heteroalkynyl, carbocyclyl (e.g., cycloalkyl), aryl, heteroaryl, and heterocyclyl groups may be substituted or unsubstituted. When substituted, there will generally be 1 to 4 substituents present, unless otherwise specified. Substituents include, for example: alkyl (e.g., unsubstituted and substituted, where the substituents include any group described herein, e.g., aryl, halo, hydroxy), aryl (e.g., substituted and unsubstituted phenyl), carbocyclyl (e.g., substituted and unsubstituted cycloalkyl), halogen (e.g., fluoro), hydroxyl, heteroalkyl (e.g., substituted and unsubstituted methoxy, ethoxy, or thioalkoxy), heteroaryl, heterocyclyl, amino (e.g., NH2 or mono- or dialkyl amino), azido, cyano, nitro, or thiol. Aryl, carbocyclyl (e.g., cycloalkyl), heteroaryl, and heterocyclyl groups may also be substituted with alkyl (unsubstituted and substituted such as arylalkyl (e.g., substituted and unsubstituted benzyl)).

Compounds described herein can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates, or mixtures of diastereoisomeric racemates. The optically active forms can be obtained for example by resolution of the racemates, by asymmetric synthesis or asymmetric chromatography (chromatography with a chiral adsorbent or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. "Racemate" or "racemic mixture" means a compound containing two enantiomers, wherein such mixtures exhibit no optical activity; i.e., they do not rotate the plane of polarized light. "Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on 25 opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds described herein may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide 35 of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99%, or 99.9% by weight relative to the other stereoisomers. When a single enantiomer is named or depicted by structure, the depicted or named enantiomer is at least 60%, 70%, 80%, 90%, 99%, or 99.9% by weight optically pure. When a single diastereomer is named or depicted by structure, the depicted or named diastereomer is at least 60%, 70%, 80%, 90%, 99%, or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99%, or 99.9% by mole fraction pure relative to the other stereoisomers. When a single enantiomer is named or depicted by structure, the depicted or named enantiomer is at least 60%, 70%, 80%, 90%, 99%, or 99.9% by mole fraction pure. When a single diastereomer is named or depicted by structure, the depicted or named diastereomer is at least 60%, 70%, 80%, 90%, 99%, or 99.9% by mole fraction pure.

Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound, or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s), or mixtures of diastereomers in which one or more diastereomer is enriched relative to the other diastereomers. The invention embraces all of these forms.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Definitions

In this application, unless otherwise clear from context, (i) the term "a" may be understood to mean "at least one"; (ii) the term "or" may be understood to mean "and/or"; and (iii) the terms "including" and "including" may be understood to encompass itemized components or steps whether presented by themselves or together with one or more additional components or steps.

As used herein, the terms "about" and "approximately" refer to a value that is within 10% above or below the value being described. For example, the term "about 5 nM" indicates a range of from 4.5 to 5.5 nM.

As used herein, the term "administration" refers to the administration of a composition (e.g., a compound or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intratumoral, intravenous, intraventricular, mucosal, nasal, oral, rectal, subcutaneous, sublingual, topical, tracheal (including by intratracheal instillation), transdermal, vaginal, and vitreal.

As used herein, the term "BAF complex" refers to the BRG1-associated or HBRM-associated factors complex in a human cell.

As used herein, the term "BRG1 loss of function mutation" refers to a mutation in BRG1 that leads to the protein having diminished activity (e.g., at least 1% reduction in BRG1 activity, for example 2%, 5%, 10%, 25%, 50%, or 100% reduction in BRG1 activity). Exemplary BRG1 loss of function mutations include, but are not limited to, a homozygous BRG1 mutation and a deletion at the C-terminus of BRG1.

As used herein, the term "BRG1 loss of function disorder" refers to a disorder (e.g., cancer) that exhibits a reduction in BRG1 activity (e.g., at least 1% reduction in BRG1 activity, for example 2%, 5%, 10%, 25%, 50%, or 100% reduction in BRG1 activity).

As used herein, the term "BRM loss of function mutation" refers to a mutation in BRM that leads to the protein having diminished activity (e.g., at least 1% reduction in BRM activity, for example 2%, 5%, 10%, 25%, 50%, or 100% reduction in BRM activity). Exemplary BRM loss of function mutations include, but are not limited to, a homozygous BRM mutation and a deletion at the C-terminus of BRM.

As used herein, the term "BRM loss of function disorder" refers to a disorder (e.g., cancer) that exhibits a reduction in BRM activity (e.g., at least 1% reduction in BRM activity, for example 2%, 5%, 10%, 25%, 50%, or 100% reduction in BRG1 activity).

As used herein, the terms "GBAF complex" and "GBAF" refer to a SWI/SNF ATPase chromatin remodeling complex in a human cell. GBAF complex subunits may include, but are not limited to, ACTB, ACTL6A, ACTL6B, BICRA, BICRAL, BRD9, SMARCA2, SMARCA4, SMARCC1, SMARCD1, SMARCD2, SMARCD3, and SS18.

The term "cancer" refers to a condition caused by the proliferation of malignant neoplastic cells, such as tumors, neoplasms, carcinomas, sarcomas, leukemias, and lymphomas.

As used herein, a "combination therapy" or "administered in combination" means that two (or more) different agents or treatments are administered to a subject as part of a defined treatment regimen for a particular disease or condition. The treatment regimen defines the doses and periodicity of administration of each agent such that the effects of the separate agents on the subject overlap. In some embodiments, the delivery of the two or more agents is simultaneous or concurrent and the agents may be co-formulated. In some embodiments, the two or more agents are not co-formulated and are administered in a sequential manner as part of a prescribed regimen. In some embodiments, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination may be administered by intravenous injection while a second therapeutic agent of the combination may be administered orally.

As used herein, the term "BRG1" refers to ATP-dependent chromatin remodeler SMARCA4. BRG1 is a component of the BAF complex, a SWI/SNF ATPase chromatin remodeling complex. Human BRG1 is encoded by the SMARCA4 gene on chromosome 19, a nucleic acid sequence of which is set forth in SEQ ID NO: 1 (GenBank Accession No.: NM_001128849.1 (mRNA); www.ncbi.nlm.nih.gov/nuccore/NM_001128849.1?report=fasta).

```
GGCGGGGGAGGCGCCGGGAAGTCGACGGCGCCGGCGGCTCCTGCAGGAGGCCACTGTCTGCAGCTCCCGT

GAAGATGTCCACTCCAGACCCACCCCTGGGCGGAACTCCTCGGCCAGGTCCTTCCCCGGGCCCTGGCCCT

TCCCCTGGAGCCATGCTGGGCCCTAGCCCGGGTCCCTCGCCGGGCTCCGCCCACAGCATGATGGGGCCCA

GCCCAGGGCCGCCCTCAGCAGGACACCCCATCCCCACCCAGGGGCCTGGAGGGTACCCTCAGGACAACAT

GCACCAGATGCACAAGCCCATGGAGTCCATGCATGAGAAGGGCATGTCGGACGACCCGCGCTACAACCAG

ATGAAAGGAATGGGGATGCGGTCAGGGGGCCATGCTGGGATGGGGCCCCCGCCCAGCCCCATGGACCAGC

ACTCCCAAGGTTACCCCTCGCCCCTGGGTGGCTCTGAGCATGCCTCTAGTCCAGTTCCAGCCAGTGGCCC

GTCTTCGGGGCCCCAGATGTCTTCCGGGCCAGGAGGTGCCCCGCTGGATGGTGCTGACCCCCAGGCCTTG

GGGCAGCAGAACCGGGGCCCAACCCCATTTAACCAGAACCAGCTGCACCAGCTCAGAGCTCAGATCATGG

CCTACAAGATGCTGGCCAGGGGGCAGCCCCTCCCCGACCACCTGCAGATGGCGGTGCAGGGCAAGCGGCC

GATGCCCGGGATGCAGCAGCAGATGCCAACGCTACCTCCACCCTCGGTGTCCGCAACAGGACCCGGCCCT

GGCCCTGGCCCTGGCCCCGGCCCGGGTCCCGGCCCGGCACCTCCAAATTACAGCAGGCCTCATGGTATGG

GAGGGCCCAACATGCCTCCCCCAGGACCCTCGGGCGTGCCCCCCGGGATGCCAGGCCAGCCTCCTGGAGG

GCCTCCCAAGCCCTGGCCTGAAGGACCCATGGCGAATGCTGCTGCCCCCACGAGCACCCCTCAGAAGCTG

ATTCCCCCGCAGCCAACGGGCCGCCCTTCCCCCGCGCCCCCTGCCGTCCCACCCGCCGCCTCGCCCGTGA

TGCCACCGCAGACCCAGTCCCCCGGGCAGCCGGCCCAGCCCGCGCCCATGGTGCCACTGCACCAGAAGCA

GAGCCGCATCACCCCCATCCAGAAGCGCGGGGCCTCGACCCTGTGGAGATCCTGCAGGAGCGCGAGTAC

AGGCTGCAGGCTCGCATCGCACACCGAATTCAGGAACTTGAAAACCTTCCCGGGTCCCTGGCCGGGGATT
```

-continued

```
TGCGAACCAAAGCGACCATTGAGCTCAAGGCCCTCAGGCTGCTGAACTTCCAGAGGCAGCTGCGCCAGGA
GGTGGTGGTGTGCATGCGGAGGGACACAGCGCTGGAGACAGCCCTCAATGCTAAGGCCTACAAGCGCAGC
AAGCGCCAGTCCCTGCGCGAGGCCCGCATCACTGAGAAGCTGGAGAAGCAGCAGAAGATCGAGCAGGAGC
GCAAGCGCCGGCAGAAGCACCAGGAATACCTCAATAGCATTCTCCAGCATGCCAAGGATTTCAAGGAATA
TCACAGATCCGTCACAGGCAAAATCCAGAAGCTGACCAAGGCAGTGGCCACGTACCATGCCAACACGGAG
CGGGAGCAGAAGAAAGAGAACGAGCGGATCGAGAAGGAGCGCATGCGGAGGCTCATGGCTGAAGATGAGG
AGGGGTACCGCAAGCTCATCGACCAGAAGAAGGACAAGCGCCTGGCCTACCTCTTGCAGCAGACAGACGA
GTACGTGGCTAACCTCACGGAGCTGGTGCGGCAGCACAAGGCTGCCCAGGTCGCCAAGGAGAAAAAGAAG
AAAAAGAAAAAGAAGAAGGCAGAAAATGCAGAAGGACAGACGCCTGCCATTGGGCCGGATGGCGAGCCTC
TGGACGAGACCAGCCAGATGAGCGACCTCCCGGTGAAGGTGATCCACGTGGAGAGTGGGAAGATCCTCAC
AGGCACAGATGCCCCCAAAGCCGGGCAGCTGGAGGCCTGGCTCGAGATGAACCCGGGGTATGAAGTAGCT
CCGAGGTCTGATAGTGAAGAAAGTGGCTCAGAAGAAGAGGAAGAGGAGGAGGAGGAAGAGCAGCCGCAGG
CAGCACAGCCTCCCACCCTGCCCGTGGAGGAGAAGAAGAAGATTCCAGATCCAGACAGCGATGACGTCTC
TGAGGTGGACGCGCGGCACATCATTGAGAATGCCAAGCAAGATGTCGATGATGAATATGGCGTGTCCCAG
GCCCTTGCACGTGGCCTGCAGTCCTACTATGCCGTGGCCCATGCTGTCACTGAGAGAGTGGACAAGCAGT
CAGCGCTTATGGTCAATGGTGTCCTCAAACAGTACCAGATCAAAGGTTTGGAGTGGCTGGTGTCCCTGTA
CAACAACAACCTGAACGGCATCCTGGCCGACGAGATGGGCCTGGGGAAGACCATCCAGACCATCGCGCTC
ATCACGTACCTCATGGAGCACAAACGCATCAATGGGCCCTTCCTCATCATCGTGCCTCTCTCAACGCTGT
CCAACTGGGCGTACGAGTTTGACAAGTGGGCCCCCTCCGTGGTGAAGGTGTCTTACAAGGGATCCCCAGC
AGCAAGACGGGCCTTTGTCCCCCAGCTCCGGAGTGGGAAGTTCAACGTCTTGCTGACGACGTACGAGTAC
ATCATCAAAGACAAGCACATCCTCGCCAAGATCCGTTGGAAGTACATGATTGTGGACGAAGGTCACCGCA
TGAAGAACCACCACTGCAAGCTGACGCAGGTGCTCAACACGCACTATGTGGCACCCCGCCGCCTGCTGCT
GACGGGCACACCGCTGCAGAACAAGCTTCCCGAGCTCTGGGCGCTGCTCAACTTCCTGCTGCCCACCATC
TTCAAGAGCTGCAGCACCTTCGAGCAGTGGTTTAACGCACCCTTTGCCATGACCGGGGAAAAGGTGGACC
TGAATGAGGAGGAAACCATTCTCATCATCCGGCGTCTCCACAAAGTGCTGCGGCCCTTCTTGCTCCGACG
ACTCAAGAAGGAAGTCGAGGCCCAGTTGCCCGAAAAGGTGGAGTACGTCATCAAGTGCGACATGTCTGCG
CTGCAGCGAGTGCTCTACCGCCACATGCAGGCCAAGGGCGTGCTGCTGACTGATGGCTCCGAGAAGGACA
AGAAGGGCAAAGGCGGCACCAAGACCCTGATGAACACCATCATGCAGCTGCGGAAGATCTGCAACCACCC
CTACATGTTCCAGCACATCGAGGAGTCCTTTTCCGAGCACTTGGGGTTCACTGGCGGCATTGTCCAAGGG
CTGGACCTGTACCGAGCCTCGGGTAAATTTGAGCTTCTTGATAGAATTCTTCCCAAACTCCGAGCAACCA
ACCACAAAGTGCTGCTGTTCTGCCAAATGACCTCCCTCATGACCATCATGGAAGATTACTTTGCGTATCG
CGGCTTTAAATACCTCAGGCTTGATGGAACCACGAAGGCGGAGGACCGGGGCATGCTGCTGAAAACCTTC
AACGAGCCCGGCTCTGAGTACTTCATCTTCCTGCTCAGCACCCGGGCTGGGGGGCTCGGCCTGAACCTCC
AGTCGGCAGACACTGTGATCATTTTTGACAGCGACTGGAATCCTCACCAGGACCTGCAAGCGCAGGACCG
AGCCCACCGCATCGGGCAGCAGAACGAGGTGCGTGTGCTCCGCCTCTGCACCGTCAACAGCGTGGAGGAG
AAGATCCTAGCTGCAGCCAAGTACAAGCTCAACGTGGACCAGAAGGTGATCCAGGCCGGCATGTTCGACC
AGAAGTCCTCCAGCCATGAGCGGCGCGCCTTCCTGCAGGCCATCCTGGAGCACGAGGAGCAGGATGAGAG
CAGACACTGCAGCACGGGCAGCGGCAGTGCCAGCTTCGCCCACACTGCCCCTCCGCCAGCGGGCGTCAAC
CCCGACTTGGAGGAGCCACCTCTAAAGGAGGAAGACGAGGTGCCCGACGACGAGACCGTCAACCAGATGA
TCGCCCGGCACGAGGAGGAGTTTGATCTGTTCATGCGCATGGACCTGGACCGCAGGCGCGAGGAGGCCCG
CAACCCCAAGCGGAAGCCGCGCCTCATGGAGGAGGACGAGCTCCCCTCGTGGATCATCAAGGACGACGCG
```

-continued

```
GAGGTGGAGCGGCTGACCTGTGAGGAGGAGGAGGAGAAGATGTTCGGCCGTGGCTCCCGCCACCGCAAGG

AGGTGGACTACAGCGACTCACTGACGGAGAAGCAGTGGCTCAAGAAAATTACAGGAAAAGATATCCATGA

CACAGCCAGCAGTGTGGCACGTGGGCTACAATTCCAGCGTGGCCTTCAGTTCTGCACACGTGCGTCAAAG

GCCATCGAGGAGGGCACGCTGGAGGAGATCGAAGAGGAGGTCCGGCAGAAGAAATCATCACGGAAGCGCA

AGCGAGACAGCGACGCCGGCTCCTCCACCCCGACCACCAGCACCCGCAGCCGCGACAAGGACGACGAGAG

CAAGAAGCAGAAGAAGCGCGGGCGGCCGCCTGCCGAGAAACTCTCCCCTAACCCACCCAACCTCACCAAG

AAGATGAAGAAGATTGTGGATGCCGTGATCAAGTACAAGGACAGCAGCAGTGGACGTCAGCTCAGCGAGG

TCTTCATCCAGCTGCCCTCGCGAAAGGAGCTGCCCGAGTACTACGAGCTCATCCGCAAGCCCGTGGACTT

CAAGAAGATAAAGGAGCGCATTCGCAACCACAAGTACCGCAGCCTCAACGACCTAGAGAAGGACGTCATG

CTCCTGTGCCAGAACGCACAGACCTTCAACCTGGAGGGCTCCCTGATCTATGAAGACTCCATCGTCTTGC

AGTCGGTCTTCACCAGCGTGCGGCAGAAAATCGAGAAGGAGGATGACAGTGAAGGCGAGGAGAGTGAGGA

GGAGGAAGAGGGCGAGGAGGAAGGCTCCGAATCCGAATCTCGGTCCGTCAAAGTGAAGATCAAGCTTGGC

CGGAAGGAGAAGGCACAGGACCGGCTGAAGGGCGGCCGGCGGCGGCCGAGCCGAGGGTCCCGAGCCAAGC

CGGTCGTGAGTGACGATGACAGTGAGGAGGAACAAGAGGAGGACCGCTCAGGAAGTGGCAGCGAAGAAGA

CTGAGCCCCGACATTCCAGTCTCGACCCCGAGCCCCTCGTTCCAGAGCTGAGATGGCATAGGCCTTAGCA

GTAACGGGTAGCAGCAGATGTAGTTTCAGACTTGGAGTAAAACTGTATAAACAAAAGAATCTTCCATATT

TATACAGCAGAGAAGCTGTAGGACTGTTTGTGACTGGCCCTGTCCTGGCATCAGTAGCATCTGTAACAGC

ATTAACTGTCTTAAAGAGAGAGAGAGAGAATTCCGAATTGGGGAACACACGATACCTGTTTTTCTTTTCC

GTTGCTGGCAGTACTGTTGCGCCGCAGTTTGGAGTCACTGTAGTTAAGTGTGGATGCATGTGCGTCACCG

TCCACTCCTCCTACTGTATTTTATTGGACAGGTCAGACTCGCCGGGGCCCGGCGAGGGTATGTCAGTGT

CACTGGATGTCAAACAGTAATAAATTAAACCAACAACAAAACGCACAGCCAAAAAAAAA
```

The term "BRG1" also refers to natural variants of the wild-type human BRG1 protein, such as proteins having at least 85% identity (e.g., 85%, 86%, 87%, 88%, 89%, 90%, 91%, 92%, 93%, 94%, 95%, 96%, 97%, 98%, 99%, 99.9% identity, or more) to an amino acid sequence of wild-type BRG1, which is set forth in SEQ ID NO: 2 (UniProt Accession No.: P51532; www.uniprot.org/uniprot/P51532.fasta).

```
                              SEQ ID NO: 2
MSTPDPPLGGTPRPGPSPGPGPSPGAMLGPSPGPSPGSAHSMMGPSPGP

PSAGHPIPTQGPGGYPQDNMHQMHKPMESMHEKGMSDDPRYNQMKGMGM

RSGGHAGMGPPPSPMDQHSQGYPSPLGGSEHASSPVPASGPSSGPQMSS

GPGGAPLDGADPQALGQQNRGPTPFNQNQLHQLRAQIMAYKMLARGQPL

PDHLQMAVQGKRPMPGMQQQMPTLPPPSVSATGPGPGPGPGPGPGPGPA

PPNYSRPHGMGGPNMPPPGPSGVPPGMPGQPPGGPPKPWPEGPMANAAA

PTSTPQKLIPPQPTGRPSPAPPAVPPAASPVMPPQTQSPGQPAQPAPMV

PLHQKQSRITPIQKPRGLDPVEILQEREYRLQARIAHRIQELENLPGSL

AGDLRTKATIELKALRLLNFQRQLRQEVVVCMRRDTALETALNAKAYKR

SKRQSLREARITEKLEKQQKIEQERKRRQKHQEYLNSILQHAKDEKEYH

RSVTGKIQKLTKAVATYHANTEREQKKENERIEKERMRRLMAEDEEGYR

KLIDQKKDKRLAYLLQQTDEYVANLTELVRQHKAAQVAKEKKKKKKKKK

-continued
AENAEGQTPAIGPDGEPLDETSQMSDLPVKVIHVESGKILTGTDAPKAG

QLEAWLEMNPGYEVAPRSDSEESGSEEEEEEEEEEQPQAAQPPTLPVEE

KKKIPDPDSDDVSEVDARHIIENAKQDVDDEYGVSQALARGLQSYYAVA

HAVTERVDKQSALMVNGVLKQYQIKGLEWLVSLYNNNLNGILADEMGLG

KTIQTIALITYLMEHKRINGPFLIIVPLSTLSNWAYEFDKWAPSVVKVS

YKGSPAARRAFVPQLRSGKENVLLTTYEYIIKDKHILAKIRWKYMIVDE

GHRMKNHHCKLTQVLNTHYVAPRRLLLTGTPLQNKLPELWALLNELLPT

IFKSCSTFEQWENAPFAMTGEKVDLNEEETILIIRRLHKVLRPFLLRRL

KKEVEAQLPEKVEYVIKCDMSALQRVLYRHMQAKGVLLTDGSEKDKKGK

GGTKILMNTIMQLRKICNHPYMFQHIEESFSEHLGFTGGIVQGLDLYRA

SGKFELLDRILPKLRATNHKVLLFCQMTSLMTIMEDYFAYRGEKYLRLD

GITKAEDRGMLLKTFNEPGSEYFIFLLSTRAGGLGLNLQSADTVIIFDS

DWNPHQDLQAQDRAHRIGQQNEVRVLRLCTVNSVEEKILAAAKYKLNVD

QKVIQAGMFDQKSSSHERRAFLQAILEHEEQDESRHCSTGSGSASFAHT

APPPAGVNPDLEEPPLKEEDEVPDDETVNQMIARHEEEFDLFMRMDLDR

RREEARNPKRKPRLMEEDELPSWIIKDDAEVERLICEEEEEKMFGRGSR

HRKEVDYSDSLTEKQWLKAIEEGTLEEIEEEVRQKKSSRKRKRDSDAGS

STPTTSTRSRDKDDESKKQKKRGRPPAEKLSPNPPNLTKKMKKIVDAVI
```

-continued

KYKDSSSGRQLSEVFIQLPSRKELPEYYELIRKPVDFKKIKERIRNHKY

RSLNDLEKDVMLLCQNAQTFNLEGSLIYEDSIVLQSVFTSVRQKIEKED

DSEGEESEEEEEGEEEGSESESRSVKVKIKLGRKEKAQDRLKGGRRRPS

RGSRAKPVVSDDDSEEEQEEDRSGSGSEED.

As used herein, the term "BRM" refers to probable global transcription activator SNF2L2. BRM is a component of the BAF complex, a SWI/SNF ATPase chromatin remodeling complex. Human BRM is encoded by the SMARCA2 gene on chromosome 9, a nucleic acid sequence of which is set forth in SEQ ID NO: 3 (GenBank Accession No.: NM_003070.4, www.ncbi.nlm.nih.gov/nuccore/NM_003070.4?report=fasta).

SEQ ID NO: 3

GCGTCTTCCGGCGCCCGCGGAGGAGGCGAGGGTGGGACGCTGGGCGGAGCCCGAGTTTAGGAAGAGGAGG

GGACGGCTGTCATCAATGAAGTCATATTCATAATCTAGTCCTCTCTCCCTCTGTTTCTGTACTCTGGGTG

ACTCAGAGAGGGAAGAGATTCAGCCAGCACACTCCTCGCGAGCAAGCATTACTCTACTGACTGGCAGAGA

CAGGAGAGGTAGATGTCCACGCCCACAGACCCTGGTGCGATGCCCCACCCAGGGCCTTCGCCGGGGCCTG

GGCCTTCCCCTGGGCCAATTCTTGGGCCTAGTCCAGGACCAGGACCATCCCCAGGTTCCGTCCACAGCAT

GATGGGGCCAAGTCCTGGACCTCCAAGTGTCTCCCATCCTATGCCGACGATGGGGTCCACAGACTTCCCA

CAGGAAGGCATGCATCAAATGCATAAGCCCATCGATGGTATACATGACAAGGGGATTGTAGAAGACATCC

ATTGTGGATCCATGAAGGGCACTGGTATGCGACCACCTCACCCAGGCATGGGCCCTCCCCAGAGTCCAAT

GGATCAACACAGCCAAGGTTATATGTCACCACACCCATCTCCATTAGGAGCCCCAGAGCACGTCTCCAGC

CCTATGTCTGGAGGAGGCCCAACTCCACCTCAGATGCCACCAAGCCAGCCGGGGCCCTCATCCCAGGTG

ATCCGCAGGCCATGAGCCAGCCCAACAGAGGTCCCTCACCTTTCAGTCCTGTCCAGCTGCATCAGCTTCG

AGCTCAGATTTTAGCTTATAAAATGCTGGCCCGAGGCCAGCCCCTCCCCGAAACGCTGCAGCTTGCAGTC

CAGGGGAAAAGGACGTTGCCTGGCTTGCAGCAACAACAGCAGCAGCAACAGCAGCAGCAGCAGCAGCAGC

AGCAGCAGCAGCAGCAACAGCAGCCGCAGCAGCAGCCGCCGCAACCACAGACGCAGCAACAACAGCA

GCCGGCCCTTGTTAACTACAACAGACCATCTGGCCCGGGGCCGGAGCTGAGCGGCCCGAGCACCCCGCAG

AAGCTGCCGGTGCCCGCGCCCGGCGGCCGGCCCTCGCCCGCGCCCCCCGCAGCCGCGCAGCCGCCCGCGG

CCGCAGTGCCCGGGCCCTCAGTGCCGCAGCCGGCCCCGGGGCAGCCCTCGCCCGTCCTCCAGCTGCAGCA

GAAGCAGAGCCGCATCAGCCCCATCCAGAAACCGCAAGGCCTGGACCCCGTGGAAATTCTGCAAGAGCGG

GAATACAGACTTCAGGCCCGCATAGCTCATAGGATACAAGAACTGGAAAATCTGCCTGGCTCTTTGCCAC

CAGATTTAAGAACCAAAGCAACCGTGGAACTAAAAGCACTTCGGTTACTCAATTTCCAGCGTCAGCTGAG

ACAGGAGGTGGTGGCCTGCATGCGCAGGGACACGACCCTGGAGACGGCTCTCAACTCCAAAGCATACAAA

CGGAGCAAGCGCCAGACTCTGAGAGAAGCTCGCATGACCGAGAAGCTGGAGAAGCAGCAGAAGATTGAGC

AGGAGAGGAAACGCCGTCAGAAACACCAGGAATACCTGAACAGTATTTTGCAACATGCAAAAGATTTTAA

GGAATATCATCGGTCTGTGGCCGGAAAGATCCAGAAGCTCTCCAAAGCAGTGGCAACTTGGCATGCCAAC

ACTGAAAGAGAGCAGAAGAAGGAGACAGAGCGGATTGAAAAGGAGAGAATGCGGCGACTGATGGCTGAAG

ATGAGGAGGGTTATAGAAAACTGATTGATCAAAAGAAAGACAGGCGTTTAGCTTACCTTTTGCAGCAGAC

CGATGAGTATGTAGCCAATCTGACCAATCTGGTTTGGGAGCACAAGCAAGCCCAGGCAGCCAAAGAGAAG

AAGAAGAGGAGGAGGAGGAAGAAGAAGGCTGAGGAGAATGCAGAGGGTGGGAGTCTGCCCTGGGACCGG

ATGGAGAGCCCATAGATGAGAGCAGCCAGATGAGTGACCTCCCTGTCAAAGTGACTCACACAGAAACCGG

CAAGGTTCTGTTCGGACCAGAAGCACCCAAAGCAAGTCAGCTGGACGCCTGGCTGGAAATGAATCCTGGT

TATGAAGTTGCCCCTAGATCTGACAGTGAAGAGAGTGATTCTGATTATGAGGAAGAGGATGAGGAAGAAG

AGTCCAGTAGGCAGGAAACCGAAGAGAAAATACTCCTGGATCCAAATAGCGAAGAAGTTTCTGAGAAGGA

TGCTAAGCAGATCATTGAGACAGCTAAGCAAGACGTGGATGATGAATACAGCATGCAGTACAGTGCCAGG

GGCTCCCAGTCCTACTACACCGTGGCTCATGCCATCTCGGAGAGGGTGGAGAAACAGTCTGCCCTCCTAA

-continued

```
TTAATGGGACCCTAAAGCATTACCAGCTCCAGGGCCTGGAATGGATGGTTTCCCTGTATAATAACAACTT
GAACGGAATCTTAGCCGATGAAATGGGGCTTGGAAAGACCATACAGACCATTGCACTCATCACTTATCTG
ATGGAGCACAAAAGACTCAATGGCCCCTATCTCATCATTGTTCCCCTTTCGACTCTATCTAACTGGACAT
ATGAATTTGACAAATGGGCTCCTTCTGTGGTGAAGATTTCTTACAAGGGTACTCCTGCCATGCGTCGCTC
CCTTGTCCCCCAGCTACGGAGTGGCAAATTCAATGTCCTCTTGACTACTTATGAGTATATTATAAAAGAC
AAGCACATTCTTGCAAAGATTCGGTGGAAATACATGATAGTGGACGAAGGCCACCGAATGAAGAATCACC
ACTGCAAGCTGACTCAGGTCTTGAACACTCACTATGTGGCCCCCAGAAGGATCCTCTTGACTGGGACCCC
GCTGCAGAATAAGCTCCCTGAACTCTGGGCCCTCCTCAACTTCCTCCTCCCAACAATTTTTAAGAGCTGC
AGCACATTTGAACAATGGTTCAATGCTCCATTTGCCATGACTGGTGAAAGGGTGGACTTAAATGAAGAAG
AAACTATATTGATCATCAGGCGTCTACATAAGGTGTTAAGACCATTTTTACTAAGGAGACTGAAGAAAGA
AGTTGAATCCCAGCTTCCCGAAAAAGTGGAATATGTGATCAAGTGTGACATGTCAGCTCTGCAGAAGATT
CTGTATCGCCATATGCAAGCCAAGGGGATCCTTCTCACAGATGGTTCTGAGAAAGATAAGAAGGGGAAAG
GAGGTGCTAAGACACTTATGAACACTATTATGCAGTTGAGAAAAATCTGCAACCACCCATATATGTTTCA
GCACATTGAGGAATCCTTTGCTGAACACCTAGGCTATTCAAATGGGGTCATCAATGGGGCTGAACTGTAT
CGGGCCTCAGGGAAGTTTGAGCTGCTTGATCGTATTCTGCCAAAATTGAGAGCGACTAATCACCGAGTGC
TGCTTTTCTGCCAGATGACATCTCTCATGACCATCATGGAGGATTATTTTGCTTTTCGGAACTTCCTTTA
CCTACGCCTTGATGGCACCACCAAGTCTGAAGATCGTGCTGCTTTGCTGAAGAAATTCAATGAACCTGGA
TCCCAGTATTTCATTTTCTTGCTGAGCACAAGAGCTGGTGGCCTGGGCTTAAATCTTCAGGCAGCTGATA
CAGTGGTCATCTTTGACAGCGACTGGAATCCTCATCAGGATCTGCAGGCCCAAGACCGAGCTCACCGCAT
CGGGCAGCAGAACGAGGTCCGGGTACTGAGGCTCTGTACCGTGAACAGCGTGGAGGAAAAGATCCTCGCG
GCCGCAAAATACAAGCTGAACGTGGATCAGAAAGTGATCCAGGCGGGCATGTTTGACCAAAAGTCTTCAA
GCCACGAGCGGAGGGCATTCCTGCAGGCCATCTTGGAGCATGAGGAGGAAAATGAGGAAGAAGATGAAGT
ACCGGACGATGAGACTCTGAACCAAATGATTGCTCGACGAGAAGAAGAATTTGACCTTTTTATGCGGATG
GACATGGACCGGCGGAGGGAAGATGCCCGGAACCCGAAACGGAAGCCCCGTTTAATGGAGGAGGATGAGC
TGCCCTCCTGGATCATTAAGGATGACGCTGAAGTAGAAAGGCTCACCTGTGAAGAAGAGGAGGAGAAAAT
ATTTGGGAGGGGGTCCCGCCAGCGCCGTGACGTGGACTACAGTGACGCCCTCACGGAGAAGCAGTGGCTA
AGGGCCATCGAAGACGGCAATTTGGAGGAAATGGAAGAGGAAGTACGGCTTAAGAAGCGAAAAAGACGAA
GAAATGTGGATAAAGATCCTGCAAAAGAAGATGTGGAAAAAGCTAAGAAGAGAAGAGGCCGCCCTCCCGC
TGAGAAACTGTCACCAAATCCCCCCAAACTGACAAAGCAGATGAACGCTATCATCGATACTGTGATAAAC
TACAAAGATAGGTGTAACGTGGAGAAGGTGCCCAGTAATTCTCAGTTGGAAATAGAAGGAAACAGTTCAG
GGCGACAGCTCAGTGAAGTCTTCATTCAGTTACCTTCAAGGAAAGAATTACCAGAATACTATGAATTAAT
TAGGAAGCCAGTGGATTTCAAAAAAATAAAGGAAAGGATTCGTAATCATAAGTACCGGAGCCTAGGCGAC
CTGGAGAAGGATGTCATGCTTCTCTGTCACAACGCTCAGACGTTCAACCTGGAGGGATCCCAGATCTATG
AAGACTCCATCGTCTTACAGTCAGTGTTTAAGAGTGCCCGGCAGAAAATTGCCAAAGAGGAAGAGAGTGA
GGATGAAAGCAATGAAGAGGAGGAAGAGGAAGATGAAGAAGAGTCAGAGTCCGAGGCAAAATCAGTCAAG
GTGAAAATTAAGCTCAATAAAAAAGATGACAAAGGCCGGGACAAAGGGAAAGGCAAGAAAAGGCCAAATC
GAGGAAAAGCCAAACCTGTAGTGAGCGATTTTGACAGCGATGAGGAGCAGGATGAACGTGAACAGTCAGA
AGGAAGTGGGACGGATGATGAGTGATCAGTATGGACCTTTTTCCTTGGTAGAACTGAATTCCTTCCTCCC
CTGTCTCATTTCTACCCAGTGAGTTCATTTGTCATATAGGCACTGGGTTGTTTCTATATCATCATCGTCT
ATAAACTAGCTTTAGGATAGTGCCAGACAAACATATGATATCATGGTGTAAAAAACACACACATACACAA
ATATTTGTAACATATTGTGACCAAATGGGCCTCAAAGATTCAGATTGAAACAAACAAAAAGCTTTTGATG
```

```
-continued
GAAAATATGTGGGTGGATAGTATATTTCTATGGGTGGGTCTAATTTGGTAACGGTTTGATTGTGCCTGGT

TTTATCACCTGTTCAGATGAGAAGATTTTTGTCTTTTGTAGCACTGATAACCAGGAGAAGCCATTAAAAG

CCACTGGTTATTTTATTTTTCATCAGGCAATTTTCGAGGTTTTTATTTGTTCGGTATTGTTTTTTTACAC

TGTGGTACATATAAGCAACTTTAATAGGTGATAAATGTACAGTAGTTAGATTTCACCTGCATATACATTT

TTCCATTTTATGCTCTATGATCTGAACAAAAGCTTTTTGAATTGTATAAGATTTATGTCTACTGTAAACA

TTGCTTAATTTTTTTGCTCTTGATTTAAAAAAAAGTTTTGTTGAAAGCGCTATTGAATATTGCAATCTAT

ATAGTGTATTGGATGGCTTCTTTTGTCACCCTGATCTCCTATGTTACCAATGTGTATCGTCTCCTTCTCC

CTAAAGTGTACTTAATCTTTGCTTTCTTTGCACAATGTCTTTGGTTGCAAGTCATAAGCCTGAGGCAAAT

AAAATTCCAGTAATTTCGAAGAATGTGGTGTTGGTGCTTTCCTAATAAAGAAATAATTTAGCTTGACAAA.
```

The term "BRM" also refers to natural variants of the wild-type human BRM protein, such as proteins having at least 85% identity (e.g., 85%, 86%, 87%, 88%, 89%, 90%, 91%, 92%, 93%, 94%, 95%, 96%, 97%, 98%, 99%, 99.9% identity, or more) to an amino acid sequence of wild-type BRM, which is set forth in SEQ ID NO: 4 (Uniprot Accession No.: P51531; www.uniprot.org/uniprot/P51531.fasta).

```
                                                 SEQ ID NO: 4
MSTPTDPGAMPHPGPSPGPGPSPGPILGPSPGPGPSPGSVHSMMGPSPGP

PSVSHPMPTMGSTDFPQEGMHQMHKPIDGIHDKGIVEDIHCGSMKGTGMR

PPHPGMGPPQSPMDQHSQGYMSPHPSPLGAPEHVSSPMSGGGPTPPQMPP

SQPGALIPGDPQAMSQPNRGPSPFSPVQLHQLRAQILAYKMLARGQPLPE

TLQLAVQGKRTLPGLQQQQQQQQQQQQQQQQQQQQQQQPQQQPPQPQTQQ

QQQPALVNYNRPSGPGPELSGPSTPQKLPVPAPGGRPSPAPPAAAQPPAA

AVPGPSVPQPAPGQPSPVLQLQQKQSRISPIQKPQGLDPVEILQEREYRL

QARIAHRIQELENLPGSLPPDLRTKATVELKALRLLNFQRQLRQEVVACM

RRDTTLETALNSKAYKRSKRQTLREARMTEKLEKQQKIEQERKRRQKHQE

YLNSILQHAKDFKEYHRSVAGKIQKLSKAVATWHANTEREQKKETERIEK

ERMRRLMAEDEEGYRKLIDQKKDRRLAYLLQQTDEYVANLTNLVWEHKQA

QAAKEKKKRRRRKKKAEENAEGGESALGPDGEPIDESSQMSDLPVKVTHT

ETGKVLFGPEAPKASQLDAWLEMNPGYEVAPRSDSEESDSDYEEEDEEEE

SSRQETEEKILLDPNSEEVSEKDAKQIIETAKQDVDDEYSMQYSARGSQS

YYTVAHAISERVEKQSALLINGTLKHYQLQGLEWMVSLYNNNLNGILADE

MGLGKTIQTIALITYLMEHKRLNGPYLIIVPLSTLSNWTYEFDKWAPSVV

KISYKGTPAMRRSLVPQLRSGKENVLLTTYEYIIKDKHILAKIRWKYMIV

DEGHRMKNHHCKLIQVLNTHYVAPRRILLIGTPLQNKLPELWALLNFLLP

TIFKSCSTFEQWFNAPFAMTGERVDLNEEETILIIRRLHKVLRPFLLRRL

KKEVESQLPEKVEYVIKCDMSALQKILYRHMQAKGILLTDGSEKDKKGKG

GAKTLMNTIMQLRKICNHPYMFQHIEESFAEHLGYSNGVINGAELYRASG

KFELLDRILPKLRATNHRVLLFCQMTSLMTIMEDYFAFRNFLYLRLDGIT

KSEDRAALLKKENEPGSQYFIFLLSTRAGGLGLNLQAADTWIFDSDWNPH

QDLQAQDRAHRIGQQNEVRVLRLCTVNSVEEKILAAAKYKLNVDQKVIQA

GMFDQKSSSHERRAFLQAILEHEEENEEEDEVPDDETLNQMIARREEEFD

LFMRMDMDRRREDARNPKRKPRLMEEDELPSWIIKDDAEVERLTCEEEEE

KIFGRGSRQRRDVDYSDALTEKQWLRAIEDGNLEEMEEEVRLKKRKRRRN

VDKDPAKEDVEKAKKRRGRPPAEKLSPNPPKLTKQMNAIIDTVINYKDRC

NVEKVPSNSQLEIEGNSSGRQLSEVFIQLPSRKELPEYYELIRKPVDFKK

IKERIRNHKYRSLGDLEKDVMLLCHNAQTFNLEGSQIYEDSIVLQSVFKS

ARQKIAKEEESEDESNEEEEEEDEEESESEAKSVKVKIKLNKKDDKGRDK

GKGKKRPNRGKAKPVVSDFDSDEEQDEREQSEGSGTDDE.
```

As used herein, the term "degrader" refers to a small molecule compound including a degradation moiety, wherein the compound interacts with a protein (e.g., BRG1 and/or BRM) in a way which results in degradation of the protein, e.g., binding of the compound results in at least 5% reduction of the level of the protein, e.g., in a cell or subject.

As used herein, the term "degradation moiety" refers to a moiety whose binding results in degradation of a protein, e.g., BRG1 and/or BRM. In one example, the moiety binds to a protease or a ubiquitin ligase that metabolizes the protein, e.g., BRG1 and/or BRM.

By "determining the level of a protein" is meant the detection of a protein, or an mRNA encoding the protein, by methods known in the art either directly or indirectly. "Directly determining" means performing a process (e.g., performing an assay or test on a sample or "analyzing a sample" as that term is defined herein) to obtain the physical entity or value. "Indirectly determining" refers to receiving the physical entity or value from another party or source (e.g., a third-party laboratory that directly acquired the physical entity or value). Methods to measure protein level generally include, but are not limited to, western blotting, immunoblotting, enzyme-linked immunosorbent assay (ELISA), radioimmunoassay (RIA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, liquid chromatography (LC)-mass spectrometry, microcytometry, microscopy, fluorescence activated cell sorting (FACS), and flow cytometry, as well as assays based on a property of a protein including, but not limited to, enzymatic activity or interaction with other protein partners. Methods to measure mRNA levels are known in the art.

By "modulating the activity of a BAF complex" is meant altering the level of an activity related to a BAF complex (e.g., GBAF), or a related downstream effect. The activity level of a BAF complex may be measured using any method known in the art, e.g., the methods described in Kadoch et al, Cell 153:71-85 (2013), the methods of which are herein incorporated by reference.

By "reducing the activity of BRG1 and/or BRM" is meant decreasing the level of an activity related to a BRG1 and/or BRM, or a related downstream effect. A non-limiting example of inhibition of an activity of BRG1 and/or BRM is decreasing the level of a BAF complex (e.g., GBAF) in a cell. The activity level of BRG1 and/or BRM may be measured using any method known in the art. In some embodiments, an agent which reduces the activity of BRG1 and/or BRM is a small molecule BRG1 and/or BRM inhibitor By "reducing the level of BRG1 and/or BRM" is meant decreasing the level of BRG1 and/or BRM in a cell or subject. The level of BRG1 and/or BRM may be measured using any method known in the art.

As used herein, the term "inhibiting BRG and/or BRM" refers to blocking or reducing the level or activity of the ATPase catalytic binding domain or the bromodomain of the protein. BRG1 and/or BRM inhibition may be determined using methods known in the art, e.g., a BRG and/or BRM ATPase assay, a Nano DSF assay, or a BRG1 and/or BRM Luciferase cell assay.

By "level" is meant a level of a protein, or mRNA encoding the protein, as compared to a reference. The reference can be any useful reference, as defined herein. By a "decreased level" or an "increased level" of a protein is meant a decrease or increase in protein level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a protein may be expressed in mass/vol (e.g., g/dL, mg/mL, µg/mL, ng/mL) or percentage relative to total protein or mRNA in a sample.

As used herein, the term "inhibitor" refers to any agent which reduces the level and/or activity of a protein (e.g., BRG1 and/or BRM). Non-limiting examples of inhibitors include small molecule inhibitors, degraders, antibodies, enzymes, or polynucleotides (e.g., siRNA).

As used herein, the term "LXS196," refers to the PKC inhibitor having the structure:

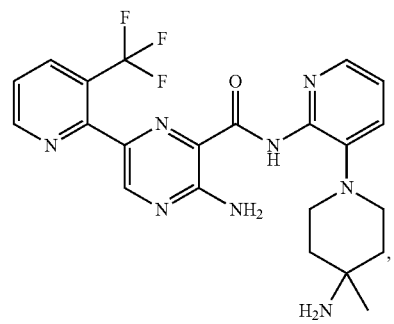 [SMILES: CC1(N)CCN(c2cccnc2NC(=O)c2nc(-c3ncccc3C(F)(F)F)cnc2N)CC1]

or a pharmaceutically acceptable salt thereof.

As used herein, the terms "effective amount," "therapeutically effective amount," and "a sufficient amount" of an agent that reduces the level and/or activity of BRG1 and/or BRM (e.g., in a cell or a subject) described herein refer to a quantity sufficient to, when administered to the subject, including a human, effect beneficial or desired results, including clinical results, and, as such, an "effective amount" or synonym thereto depends on the context in which it is being applied. For example, in the context of treating cancer, it is an amount of the agent that reduces the level and/or activity of BRG1 and/or BRM sufficient to achieve a treatment response as compared to the response obtained without administration of the agent that reduces the level and/or activity of BRG1 and/or BRM. The amount of a given agent that reduces the level and/or activity of BRG1 and/or BRM described herein that will correspond to such an amount will vary depending upon various factors, such as the given agent, the pharmaceutical formulation, the route of administration, the type of disease or disorder, the identity of the subject (e.g., age, sex, and/or weight) or host being treated, and the like, but can nevertheless be routinely determined by one of skill in the art. Also, as used herein, a "therapeutically effective amount" of an agent that reduces the level and/or activity of BRG1 and/or BRM of the present disclosure is an amount which results in a beneficial or desired result in a subject as compared to a control. As defined herein, a therapeutically effective amount of an agent that reduces the level and/or activity of BRG1 and/or BRM of the present disclosure may be readily determined by one of ordinary skill by routine methods known in the art. Dosage regimen may be adjusted to provide the optimum therapeutic response.

The term "inhibitory RNA agent" refers to an RNA, or analog thereof, having sufficient sequence complementarity to a target RNA to direct RNA interference. Examples also include a DNA that can be used to make the RNA. RNA interference (RNAi) refers to a sequence-specific or selective process by which a target molecule (e.g., a target gene, protein, or RNA) is down-regulated. Generally, an interfering RNA ("iRNA") is a double-stranded short-interfering RNA (siRNA), short hairpin RNA (shRNA), or single-stranded micro-RNA (miRNA) that results in catalytic degradation of specific mRNAs, and also can be used to lower or inhibit gene expression.

The terms "short interfering RNA" and "siRNA" (also known as "small interfering RNAs") refer to an RNA agent, preferably a double-stranded agent, of about 10-50 nucleotides in length, the strands optionally having overhanging ends comprising, for example 1, 2 or 3 overhanging nucleotides (or nucleotide analogs), which is capable of directing or mediating RNA interference. Naturally-occurring siR- NAs are generated from longer dsRNA molecules (e.g., >25 nucleotides in length) by a cell's RNAi machinery (e.g., Dicer or a homolog thereof).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region.

The terms "miRNA" and "microRNA" refer to an RNA agent, preferably a single-stranded agent, of about 10-50 nucleotides in length, preferably between about 15-25 nucleotides in length, which is capable of directing or mediating RNA interference. Naturally-occurring miRNAs are generated from stem-loop precursor RNAs (i.e., pre-miRNAs) by Dicer. The term "Dicer" as used herein, includes Dicer as well as any Dicer ortholog or homolog capable of processing dsRNA structures into siRNAs, miRNAs, siRNA-like or miRNA-like molecules. The term microRNA ("miRNA") is used interchangeably with the term "small temporal RNA" ("stRNA") based on the fact that naturally-occurring miRNAs have been found to be expressed in a temporal fashion (e.g., during development).

The term "antisense," as used herein, refers to a nucleic acid comprising a polynucleotide that is sufficiently complementary to all or a portion of a gene, primary transcript, or processed mRNA, so as to interfere with expression of the endogenous gene (e.g., BRG1 and/or BRM). "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other.

The term "antisense nucleic acid" includes single-stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 80% sequence identity (e.g., 80%, 85%, 86%, 87%, 88%, 89%, 90%, 91%, 92%, 93%, 94%, 95%, 96%, 97%, 98%, 99%, 99.9% identity, or more) with the targeted polypeptide sequence (e.g., a BRG1 and/or BRM polypeptide sequence). The antisense nucleic acid can be complementary to an entire coding strand, or to only a portion thereof. In some embodiments, an antisense nucleic acid molecule is antisense to a "coding region" of the coding strand of a nucleotide sequence. The term "coding region" refers to the region of the nucleotide sequence comprising codons that are translated into amino acid residues. In some embodiments, the antisense nucleic acid molecule is antisense to a "noncoding region" of the coding strand of a nucleotide sequence. The term "noncoding region" refers to 5' and 3' sequences that flank the coding region that are not translated into amino acids (i.e., also referred to as 5' and 3' untranslated regions). The antisense nucleic acid molecule can be complementary to the entire coding region of mRNA, or can be antisense to only a portion of the coding or noncoding region of an mRNA. For example, the antisense oligonucleotide can be complementary to the region surrounding the translation start site. An antisense oligonucleotide can be, for example, about 5, 10, 15, 20, 25, 30, 35, 40, 45, or 50 nucleotides in length.

"Percent (%) sequence identity" with respect to a reference polynucleotide or polypeptide sequence is defined as the percentage of nucleic acids or amino acids in a candidate sequence that are identical to the nucleic acids or amino acids in the reference polynucleotide or polypeptide sequence, after aligning the sequences and introducing gaps, if necessary, to achieve the maximum percent sequence identity. Alignment for purposes of determining percent nucleic acid or amino acid sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full length of the sequences being compared. For example, percent sequence identity values may be generated using the sequence comparison computer program BLAST. As an illustration, the percent sequence identity of a given nucleic acid or amino acid sequence, A, to, with, or against a given nucleic acid or amino acid sequence, B, (which can alternatively be phrased as a given nucleic acid or amino acid sequence, A that has a certain percent sequence identity to, with, or against a given nucleic acid or amino acid sequence, B) is calculated as follows:

$$100 \text{ multiplied by (the fraction } X/Y)$$

where X is the number of nucleotides or amino acids scored as identical matches by a sequence alignment program (e.g., BLAST) in that program's alignment of A and B, and where Y is the total number of nucleic acids in B. It will be appreciated that where the length of nucleic acid or amino acid sequence A is not equal to the length of nucleic acid or amino acid sequence B, the percent sequence identity of A to B will not equal the percent sequence identity of B to A.

The term "pharmaceutical composition," as used herein, represents a composition containing a compound described herein formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

A "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

As used herein, the term "pharmaceutically acceptable salt" means any pharmaceutically acceptable salt of the compound of any of the compounds described herein. For example, pharmaceutically acceptable salts of any of the compounds described herein include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting a free base group with a suitable organic acid.

The compounds described herein may have ionizable groups so as to be capable of preparation as pharmaceutically acceptable salts. These salts may be acid addition salts involving inorganic or organic acids or the salts may, in the case of acidic forms of the compounds described herein, be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

By a "reference" is meant any useful reference used to compare protein or mRNA levels. The reference can be any sample, standard, standard curve, or level that is used for comparison purposes. The reference can be a normal reference sample or a reference standard or level. A "reference sample" can be, for example, a control, e.g., a predetermined negative control value such as a "normal control" or a prior sample taken from the same subject; a sample from a normal healthy subject, such as a normal cell or normal tissue; a sample (e.g., a cell or tissue) from a subject not having a disease; a sample from a subject that is diagnosed with a disease, but not yet treated with a compound described herein; a sample from a subject that has been treated by a compound described herein; or a sample of a purified protein (e.g., any described herein) at a known normal concentration. By "reference standard or level" is meant a value or number derived from a reference sample. A "normal control value" is a pre-determined value indicative of non-disease state, e.g., a value expected in a healthy control subject. Typically, a normal control value is expressed as a range ("between X and Y"), a high threshold ("no higher than X"), or a low threshold ("no lower than X"). A subject having a measured value within the normal control value for a particular biomarker is typically referred to as "within normal limits" for that biomarker. A normal reference standard or level can be a value or number derived from a normal subject not having a disease or disorder (e.g., cancer); a subject that has been treated with a compound described herein. In preferred embodiments, the reference sample, standard, or level is matched to the sample subject sample by at least one of the following criteria: age, weight, sex, disease stage, and overall health. A standard curve of levels of a purified protein, e.g., any described herein, within the normal reference range can also be used as a reference.

As used herein, the term "subject" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the terms "treat," "treated," or "treating" mean both therapeutic treatment and prophylactic or preventative measures wherein the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment.

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein may retain or improve upon the biological activity of the original material.

The details of one or more embodiments of the invention are set forth in the description below. Other features, objects,

DETAILED DESCRIPTION

Figure 1:
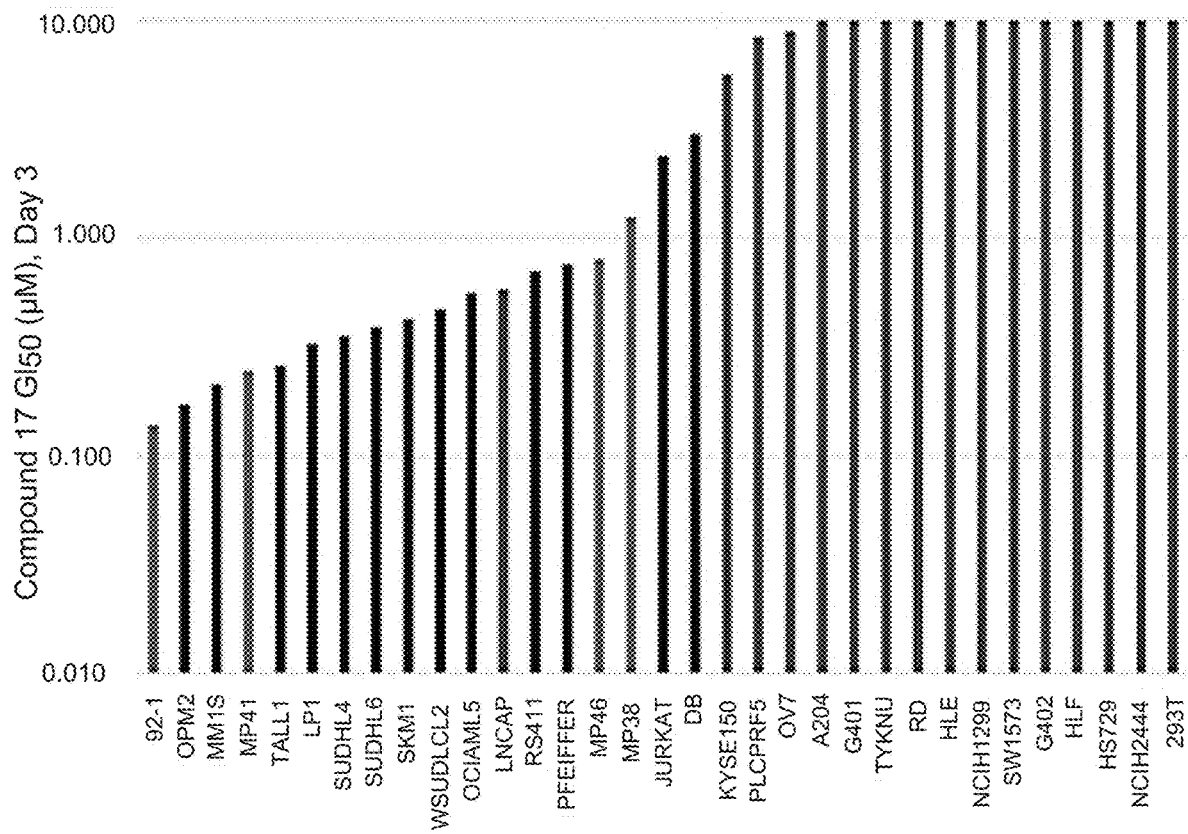
FIG. 1 is a graph illustrating inhibition of cell proliferation of several cancer cell lines by a BRG1/BRM inhibitor (compound 17).

The present inventors have found that depletion of BRG1 and/or BRM in AML results in decreased proliferation of the cancer cells.

Accordingly, the invention features methods and compositions useful for the inhibition of the activity of the BRG1 and/or BRM, e.g., for the treatment of AML. The invention further features methods and compositions useful for inhibition of the activity of the BRG1 and/or BRM protein, e.g., for the treatment of AML, e.g., in a subject in need thereof. Exemplary methods are described herein.

BRG1 and/or BRM-Reducing Agents

Agents described herein that reduce the level and/or activity of BRG1 and/or BRM in a cell may be an antibody, a protein (such as an enzyme), a polynucleotide, or a small molecule compound. The agents reduce the level of an activity related to BRG1 and/or BRM, or a related downstream effect, or reduce the level of BRG1 and/or BRM in a cell or subject.

In some embodiments, the agent that reduces the level and/or activity of BRG1 and/or BRM in a cell is an enzyme, a polynucleotide, or a small molecule compound such as a small molecule BRG1 and/or BRM inhibitor.

Antibodies

The agent that reduces the level and/or activity of BRG1 and/or BRM can be an antibody or antigen binding fragment thereof. For example, an agent that reduces the level and/or activity of BRG1 and/or BRM described herein is an antibody that reduces or blocks the activity and/or function of BRG1 and/or BRM through binding to BRG1 and/or BRM.

The making and use of therapeutic antibodies against a target antigen (e.g., BRG1 and/or BRM) is known in the art. See, for example, the references cited herein above, as well as Zhiqiang An (Editor), Therapeutic Monoclonal Antibodies: From Bench to Clinic. 1st Edition. Wiley 2009, and also Greenfield (Ed.), Antibodies: A Laboratory Manual. (Second edition) Cold Spring Harbor Laboratory Press 2013, for methods of making recombinant antibodies, including antibody engineering, use of degenerate oligonucleotides, 5'-RACE, phage display, and mutagenesis; antibody testing and characterization; antibody pharmacokinetics and pharmacodynamics; antibody purification and storage; and screening and labeling techniques.

Polynucleotides

In some embodiments, the agent that reduces the level and/or activity of BRG1 and/or BRM is a polynucleotide. In some embodiments, the polynucleotide is an inhibitory RNA molecule, e.g., that acts by way of the RNA interference (RNAi) pathway. An inhibitory RNA molecule can decrease the expression level (e.g., protein level or mRNA level) of BRG1 and/or BRM. For example, an inhibitory RNA molecule includes a short interfering RNA (siRNA), short hairpin RNA (shRNA), and/or a microRNA (miRNA) that targets full-length BRG1 and/or BRM. A siRNA is a double-stranded RNA molecule that typically has a length of about 19-25 base pairs. A shRNA is a RNA molecule including a hairpin turn that decreases expression of target genes via RNAi. A microRNA is a non-coding RNA molecule that typically has a length of about 22 nucleotides. miRNAs bind to target sites on mRNA molecules and silence the mRNA, e.g., by causing cleavage of the mRNA, destabilization of the mRNA, or inhibition of translation of the mRNA. Degradation is caused by an enzymatic, RNA-induced silencing complex (RISC).

In some embodiments, the agent that reduces the level and/or activity of BRG1 and/or BRM is an antisense nucleic acid. Antisense nucleic acids include antisense RNA (asRNA) and antisense DNA (asDNA) molecules, typically about 10 to 30 nucleotides in length, which recognize polynucleotide target sequences or sequence portions through hydrogen bonding interactions with the nucleotide bases of the target sequence (e.g., BRG1 and/or BRM). The target sequences may be single- or double-stranded RNA, or single- or double-stranded DNA.

In some embodiments, the polynucleotide decreases the level and/or activity of a negative regulator of function or a positive regulator of function. In other embodiments, the polynucleotide decreases the level and/or activity of an inhibitor of a positive regulator of function.

A polynucleotide of the invention can be modified, e.g., to contain modified nucleotides, e.g., 2'-fluoro, 2'-o-methyl, 2'-deoxy, unlocked nucleic acid, 2'-hydroxy, phosphorothioate, 2'-thiouridine, 4'-thiouridine, 2'-deoxyuridine. Without being bound by theory, it is believed that certain modification can increase nuclease resistance and/or serum stability, or decrease immunogenicity. The polynucleotides mentioned above, may also be provided in a specialized form such as liposomes, microspheres, or may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. These moieties may be attached to the nucleic acid at the 3' or 5' ends and may also be attached through a base, sugar, or intramolecular nucleoside linkage. Other moieties may be capping groups specifically placed at the 3' or 5' ends of the nucleic acid to prevent degradation by nucleases such as exonuclease, RNase, etc. Such capping groups include hydroxyl protecting groups known in the art, including glycols such as polyethylene glycol and tetraethylene glycol. The inhibitory action of the polynucleotide can be examined using a cell-line or animal based gene expression system of the present invention in vivo and in vitro. In some embodiments, the polynucleotide decreases the level and/or activity or function of BRG1 and/or BRM. In embodiments, the polynucleotide inhibits expression of BRG1 and/or BRM. In other embodiments, the polynucleotide increases degradation of BRG1 and/or BRM and/or decreases the stability (i.e., half-life) of BRG1 and/or BRM. The polynucleotide can be chemically synthesized or transcribed in vitro.

Inhibitory polynucleotides can be designed by methods well known in the art. siRNA, miRNA, shRNA, and asRNA molecules with homology sufficient to provide sequence specificity required to uniquely degrade any RNA can be designed using programs known in the art, including, but not limited to, those maintained on websites for Thermo Fisher Scientific, the German Cancer Research Center, and The Ohio State University Wexner Medical Center. Systematic testing of several designed species for optimization of the inhibitory polynucleotide sequence can be routinely performed by those skilled in the art. Considerations when designing interfering polynucleotides include, but are not limited to, biophysical, thermodynamic, and structural considerations, base preferences at specific positions in the sense strand, and homology. The making and use of inhibitory therapeutic agents based on non-coding RNA such as ribozymes, RNAse P, siRNAs, and miRNAs are also known in the art, for example, as described in Sioud, RNA Therapeutics: Function, Design, and Delivery (Methods in Molecular Biology). Humana Press 2010. Exemplary inhibitory polynucleotides, for use in the methods of the invention, are provided in Table 1, below. In some embodiments, the inhibitory polynucleotides have a nucleic acid sequence with at least 50% (e.g., at least 50%, at least 60%, at least 70%, at least 80%, at least 85%, at least 90%, at least 95%, at least 96%, at least 97%, at least 98%, at least 99%, or 100%) sequence identity to the nucleic acid sequence of an inhibitory polynucleotide in Table 1. In some embodiments, the inhibitory polynucleotides have a nucleic acid sequence with at least 70% sequence identity (e.g., 70%, 75%, 80%, 85%, 86%, 87%, 88%, 89%, 90%, 91%, 92%, 93%, 94%, 95%, 96%, 97%, 98%, 99%, 99.9% identity, or more) to the nucleic acid sequence of an inhibitory polynucleotide in Table 1.

Construction of vectors for expression of polynucleotides for use in the invention may be accomplished using conventional techniques which do not require detailed explanation to one of ordinary skill in the art. For generation of efficient expression vectors, it is necessary to have regulatory sequences that control the expression of the polynucleotide. These regulatory sequences include promoter and enhancer sequences and are influenced by specific cellular factors that interact with these sequences, and are well known in the art.

Gene Editing

In some embodiments, the agent that reduces the level and/or activity of BRG1 and/or BRM is a component of a gene editing system. For example, the agent that reduces the level and/or activity of BRG1 and/or BRM introduces an alteration (e.g., insertion, deletion (e.g., knockout), translocation, inversion, single point mutation, or other mutation) in BRG1 and/or BRM. In some embodiments, the agent that reduces the level and/or activity of BRG1 and/or BRM is a nuclease. Exemplary gene editing systems include the zinc finger nucleases (ZFNs), Transcription Activator-Like Effector-based Nucleases (TALENs), and the clustered regulatory interspaced short palindromic repeat (CRISPR) system. ZFNs, TALENs, and CRISPR-based methods are described, e.g., in Gaj et al., *Trends Biotechnol.* 31(7):397-405 (2013).

CRISPR refers to a set of (or system including a set of) clustered regularly interspaced short palindromic repeats. A CRISPR system refers to a system derived from CRISPR and Cas (a CRISPR-associated protein) or other nuclease that can be used to silence or mutate a gene described herein. The CRISPR system is a naturally occurring system found in bacterial and archeal genomes. The CRISPR locus is made up of alternating repeat and spacer sequences. In naturally-occurring CRISPR systems, the spacers are typically sequences that are foreign to the bacterium (e.g., plasmid or phage sequences). The CRISPR system has been modified for use in gene editing (e.g., changing, silencing, and/or enhancing certain genes) in eukaryotes. See, e.g., Wiedenheft et al., *Nature* 482(7385):331-338 (2012). For example, such modification of the system includes introducing into a eukaryotic cell a plasmid containing a specifically-designed CRISPR and one or more appropriate Cas proteins. The CRISPR locus is transcribed into RNA and processed by Cas proteins into small RNAs that include a repeat sequence flanked by a spacer. The RNAs serve as guides to direct Cas proteins to silence specific DNA/RNA sequences, depending on the spacer sequence. See, e.g., Horvath et al., *Science* 327(5962):167-170 (2010); Makarova et al., *Biology Direct* 1:7 (2006); Pennisi, *Science* 341(6148):833-836 (2013). In some examples, the CRISPR system includes the Cas9 protein, a nuclease that cuts on both strands of the DNA. See, e.g., Id.

In some embodiments, in a CRISPR system for use described herein, e.g., in accordance with one or more methods described herein, the spacers of the CRISPR are derived from a target gene sequence, e.g., from a BRG1 and/or BRM sequence. In some embodiments, in a CRISPR system for use described herein, e.g., in accordance with one or more methods described herein, the spacers of the CRISPR are derived from a target gene sequence, e.g., from a BRG1 sequence. In some embodiments, in a CRISPR system for use described herein, e.g., in accordance with one or more methods described herein, the spacers of the CRISPR are derived from a target gene sequence, e.g., from a BRM sequence.

In some embodiments, the agent that reduces the level and/or activity of BRG1 and/or BRM includes a guide RNA (gRNA) for use in a CRISPR system for gene editing. Exemplary gRNAs, for use in the methods of the invention, are provided in Table 1, below. In embodiments, the agent that reduces the level and/or activity of BRG1 and/or BRM includes a ZFN, or an mRNA encoding a ZFN, that targets (e.g., cleaves) a nucleic acid sequence (e.g., DNA sequence) of BRG1 and/or BRM. In embodiments, the agent that reduces the level and/or activity of BRG1 and/or BRM includes a TALEN, or an mRNA encoding a TALEN, that targets (e.g., cleaves) a nucleic acid sequence (e.g., DNA sequence) of BRG1 and/or BRM. In embodiments, the agent that reduces the level and/or activity of BRG1 and/or BRM includes a TALEN, or an mRNA encoding a TALEN, that targets (e.g., cleaves) a nucleic acid sequence (e.g., DNA sequence) of BRG1. In embodiments, the agent that reduces the level and/or activity of BRG1 and/or BRM includes a TALEN, or an mRNA encoding a TALEN, that targets (e.g., cleaves) a nucleic acid sequence (e.g., DNA sequence) of BRM.

For example, the gRNA can be used in a CRISPR system to engineer an alteration in a gene (e.g., BRG1 and/or BRM). In other examples, the ZFN and/or TALEN can be used to engineer an alteration in a gene (e.g., BRG1 and/or BRM). Exemplary alterations include insertions, deletions (e.g., knockouts), translocations, inversions, single point mutations, or other mutations. The alteration can be introduced in the gene in a cell, e.g., in vitro, ex vivo, or in vivo. In some embodiments, the alteration decreases the level and/or activity of (e.g., knocks down or knocks out) BRG1 and/or BRM, e.g., the alteration is a negative regulator of function. In yet another example, the alteration corrects a defect (e.g., a mutation causing a defect), in BRG1 and/or BRM. In yet another example, the alteration corrects a defect (e.g., a mutation causing a defect), in BRG1. In yet another example, the alteration corrects a defect (e.g., a mutation causing a defect), in BRM.

In certain embodiments, the CRISPR system is used to edit (e.g., to add or delete a base pair) a target gene, e.g., BRG1 and/or BRM. In other embodiments, the CRISPR system is used to introduce a premature stop codon, e.g., thereby decreasing the expression of a target gene. In yet other embodiments, the CRISPR system is used to turn off a target gene in a reversible manner, e.g., similarly to RNA interference. In embodiments, the CRISPR system is used to direct Cas to a promoter of a target gene, e.g., BRG1 and/or BRM, thereby blocking an RNA polymerase sterically. In embodiments, the CRISPR system is used to direct Cas to a promoter of a target gene, e.g., BRG1, thereby blocking an RNA polymerase sterically. In embodiments, the CRISPR system is used to direct Cas to a promoter of a target gene, e.g., BRM, thereby blocking an RNA polymerase sterically.

In some embodiments, a CRISPR system can be generated to edit BRG1 and/or BRM using technology described in, e.g., U.S. Publication No. 20140068797; Cong et al., *Science* 339(6121):819-823 (2013); Tsai, *Nature Biotechnol.*, 32(6):569-576 (2014); and U.S. Pat. Nos. 8,871,445; 8,865,406; 8,795,965; 8,771,945; and 8,697,359.

In some embodiments, the CRISPR interference (CRISPRi) technique can be used for transcriptional repression of specific genes, e.g., the gene encoding BRG1 and/or BRM. In CRISPRi, an engineered Cas9 protein (e.g., nuclease-null dCas9, or dCas9 fusion protein, e.g., dCas9-KRAB or dCas9-SID4x fusion) can pair with a sequence specific guide RNA (sgRNA). The Cas9-gRNA complex can block RNA polymerase, thereby interfering with transcription elongation. The complex can also block transcription initiation by interfering with transcription factor binding. The CRISPRi method is specific with minimal off-target effects and is multiplexable, e.g., can simultaneously repress more than one gene (e.g., using multiple gRNAs). Also, the CRISPRi method permits reversible gene repression. In some embodiments, CRISPR-mediated gene activation (CRISPRa) can be used for transcriptional activation, e.g., of one or more genes described herein, e.g., a gene that inhibits BRG1 and/or BRM. In the CRISPRa technique, dCas9 fusion proteins recruit transcriptional activators. For example, dCas9 can be used to recruit polypeptides (e.g., activation domains) such as VP64 or the p65 activation domain (p65D) and used with sgRNA (e.g., a single sgRNA or multiple sgRNAs), to activate a gene or genes, e.g., endogenous gene(s). Multiple activators can be recruited by using multiple sgRNAs—this can increase activation efficiency. A variety of activation domains and single or multiple activation domains can be used. In addition to engineering dCas9 to recruit activators, sgRNAs can also be engineered to recruit activators. For example, RNA aptamers can be incorporated into a sgRNA to recruit proteins (e.g., activation domains) such as VP64. In some examples, the synergistic activation mediator (SAM) system can be used for transcriptional activation. In SAM, MS2 aptamers are added to the sgRNA. MS2 recruits the MS2 coat protein (MCP) fused to p65AD and heat shock factor 1 (HSF1). The CRISPRi and CRISPRa techniques are described in greater detail, e.g., in Dominguez et al., *Nat. Rev. Mol. Cell Biol.* 17(1):5-15 (2016), incorporated herein by reference.

Small Molecule Compounds

In some embodiments of the invention, the agent that reduces the level and/or activity of BRG1 and/or BRM in a cell is a small molecule compound. In some embodiments, the small molecule compound is a structure of Formula I-III.

In some embodiments, the small molecule BRG1 and/or BRM inhibitor is a compound, or pharmaceutically acceptable salt thereof, having the structure of Formula I:

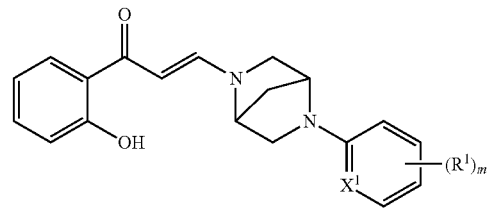

Formula I wherein m is 0, 1, 2, 3, or 4;
$X^1$ is N or CH; and
each $R^1$ is, independently, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino.

In some embodiments, the small molecule BRG1 and/or BRM inhibitor is a compound, or pharmaceutically acceptable salt thereof, having the structure of Formula II:

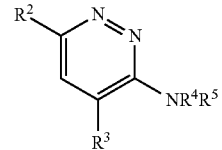

Formula II wherein $R^2$ is phenyl that is substituted with hydroxy and that is optionally substituted with one or more groups independently selected from the group consisting of halo, cyano, trifluoromethyl, trifluoromethoxy, $C_{1-3}$ alkyl, and $C_{1-3}$ alkoxy;
$R^3$ is selected from the group consisting of —$R^a$, —O—$R^a$, —N($R^a$)$_2$, —S(O)$_2$$R^a$, and —C(O)—N($R^a$)$_2$;
each $R^a$ is, independently, selected from the group consisting of hydrogen, $C_{1-6}$ alkyl, $C_{2-6}$ alkenyl, $C_{2-6}$ alkynyl, 3-15 membered carbocyclyl, and 3-15 membered heterocyclyl, wherein each $C_{1-6}$ alkyl, $C_{2-6}$ alkenyl, $C_{2-6}$ alkynyl, 3-15 membered carbocyclyl, and 3-15 membered heterocyclyl is optionally substituted with one or more groups independently selected from the group consisting of $R^b$, oxo, halo, —NO$_2$, —N($R^b$)$_2$, —CN, —C(O)—N($R^b$)$_2$, —S(O)—N($R^b$)$_2$, —S(O)$_2$—N($R^b$)$_2$, —O—$R^b$, —S—$R^b$, —O—C(O)—$R^b$, —C(O)—$R^b$, —C(O)—O$R^b$, —S(O)—$R^b$, —S(O)$_2$—$R^b$, —N($R^b$)—C(O)—$R^b$, —N($R^b$)—S(O)—$R^b$, —N($R^b$)—C(O)—N($R^b$)$_2$, and —N($R^b$)—S(O)$_2$—$R^b$;
each $R^b$ is independently selected from the group consisting of hydrogen, $C_{1-6}$ alkyl, $C_{2-6}$ alkenyl, $C_{2-6}$ alkynyl, $C_{1-6}$ alkoxy, 3-15 membered carbocyclyl, and 3-15 membered heterocyclyl, wherein each $C_{1-6}$ alkyl, $C_{2-6}$ alkenyl, $C_{2-6}$ alkynyl, $C_{1-6}$ alkoxy, 3-15 membered carbocyclyl, and 3-15 membered heterocyclyl is optionally substituted with one or more groups independently selected from RC; or two $R^b$ are taken together with the nitrogen to which they are attached to form a heterocyclyl that is optionally substituted with one or more groups independently selected from the group consisting of oxo, halo and $C_{1-3}$ alkyl that is optionally substituted with one or more groups independently selected from the group consisting of oxo and halo;

each RC is independently selected from the group consisting of oxo, halo, $-NO_2$, $-N(R^d)_2$, $-CN$, $-C(O)-N(R^d)_2$, $-S(O)-N(R^d)_2$, $-S(O)_2-N(R^d)_2$, $-S-R^d$, $-O-C(O)-R^d$, $-C(O)-R^d$, $-C(O)-OR$ d, $-S(O)-R^d$, $-S(O)_2-R^d$, $-N(R^d)-C(O)-R^d$, $-N(R^d)-S(O)-R^d$, $-N(R^d)-C(O)-N(R^d)_2$, $-N(R^d)-S(O)_2-R^d$, $C_{1-6}$ alkyl, $C_{2-6}$ alkenyl, $C_{2-6}$ alkynyl, 3-15 membered carbocyclyl, and 3-15 membered heterocyclyl, wherein any $C_{1-6}$ alkyl, $C_{2-6}$ alkenyl, $C_{2-6}$ alkynyl, 3-15 membered carbocyclyl, and 3-15 membered heterocyclyl is optionally substituted with one or more groups independently selected from the group consisting of $R^d$, oxo, halo, $-NO_2$, $-N(R^d)_2$, $-CN$, $-C(O)-N(R^d)_2$, $-S(O)-N(R^d)_2$, $-S(O)_2-N(R^d)_2$, $-O-R^d$, $-S-R^d$, $-O-C(O)-R^d$, $-C(O)-R^d$, $-C(O)-R^d$, $-S(O)-R^d$, $-S(O)_2-R^d$, $-N(R^d)-C(O)-R^d$, $-N(R^d)-S(O)-R^d$, $-N(R^d)-C(O)-N(R^d)_2$, and $-N(R^d)-S(O)_2-R^d$;

each $R^d$ is independently selected from the group consisting of hydrogen, $C_{1-6}$ alkyl, $C_{2-6}$ alkenyl, $C_{2-6}$ alkynyl, carbocyclyl, and carbocyclyl($C_{1-3}$ alkyl)-;

$R^4$ is H, $C_{1-6}$ alkyl, or $-C(=O)-C_{1-6}$ alkyl; and $R^5$ is H or $C_{1-6}$ alkyl.

Compounds of Formula II may be synthesized by methods known in the art, e.g., those described in U.S. Patent Publication No. 2018/0086720, the synthetic methods of which are incorporated by reference.

In some embodiments, the small molecule BRG1 and/or BRM inhibitor is a compound, or pharmaceutically acceptable salt thereof, having the structure of Formula III:

Formula III

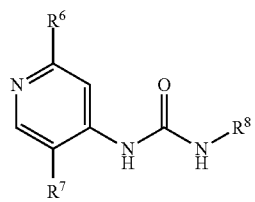

wherein $R^6$ is halo, e.g., fluoro or chloro;

$R^7$ is hydrogen, optionally substituted amino, or optionally substituted $C_1$—B alkyl; and $R^8$ is optionally substituted $C_{6-10}$ aryl or optionally substituted $C_{2-9}$ heteroaryl.

In some embodiments, the small molecule BRG1 and/or BRM inhibitor is a compound, or pharmaceutically acceptable salt thereof, having the structure of any one of compounds 1-16:

1

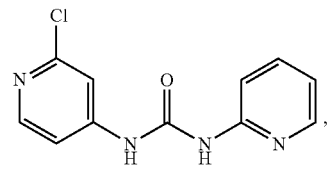

2

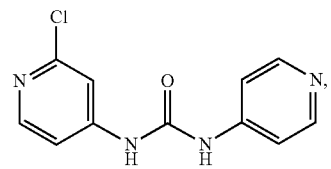

3

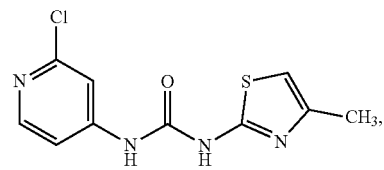

4

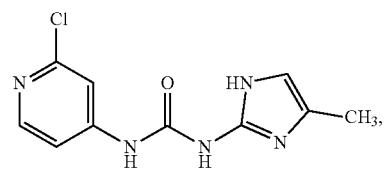

5

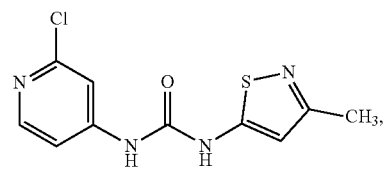

6

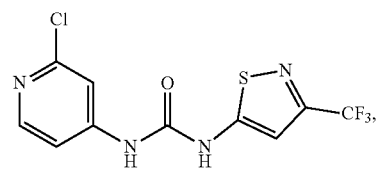

7

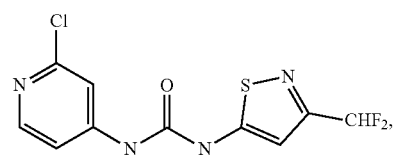

8

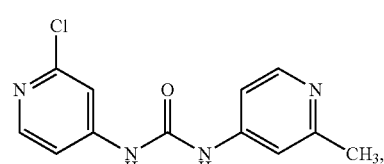

9

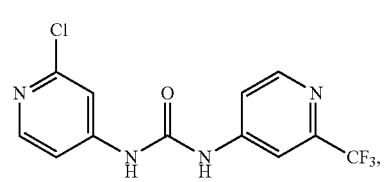

-continued

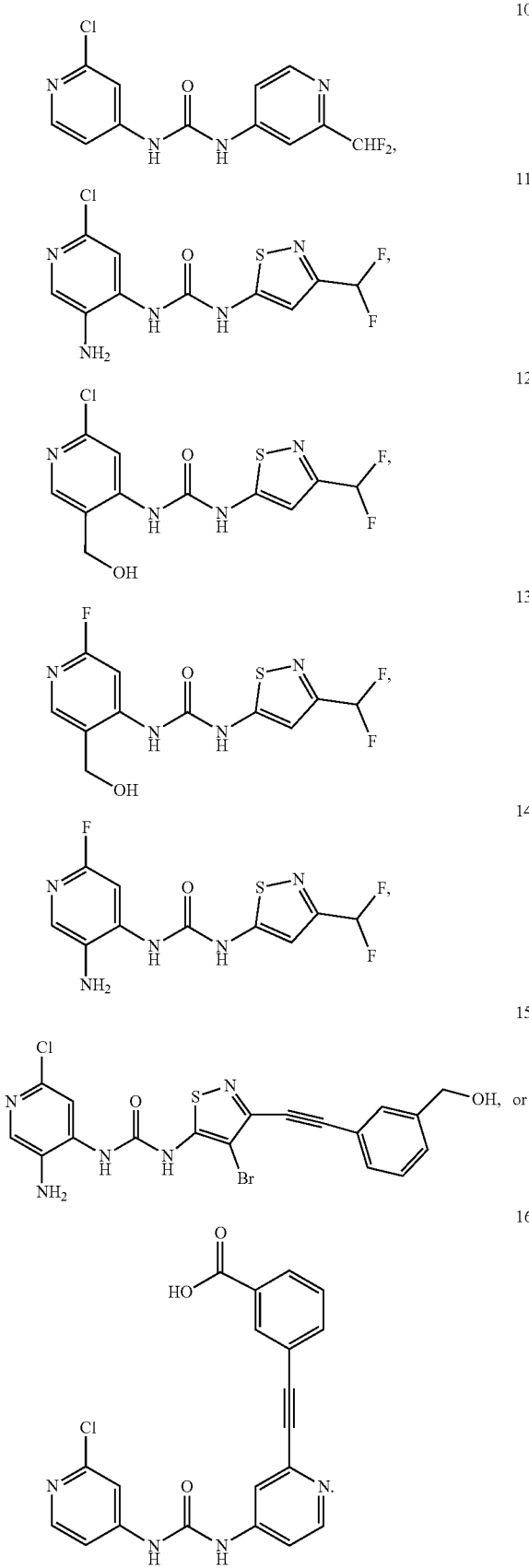

In some embodiments, the small molecule BRG1 and/or BRM inhibitor is a compound, or pharmaceutically acceptable salt thereof, having the structure of Formula IV:

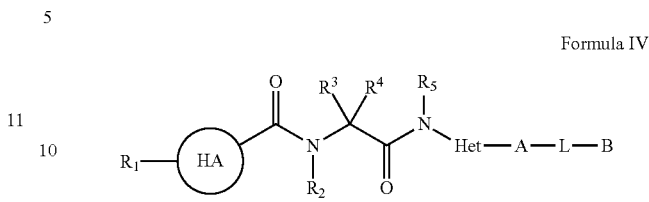

Formula IV where $R^1$ is absent, H, optionally substituted $C_1$-$C_6$ acyl, optionally substituted $C_1$-$C_6$ alkyl, optionally substituted $C_3$-$C_8$ cycloalkyl, optionally substituted $C_1$-$C_6$ heteroalkyl, optionally substituted $C_2$-$C_9$ heterocyclyl, or —$SO_2R^6$;

HA is 5- or 6-membered heteroarylene;

each of $R^2$ and $R^5$ is, independently, H or optionally substituted $C_1$-$C_6$ alkyl;

$R^3$ is H or optionally substituted $C_1$-$C_6$ alkyl; and $R^4$ is H, optionally substituted $C_1$-$C_6$ alkyl, or optionally substituted $C_1$-$C_6$ heteroalkyl; or $R^3$ and $R^4$, together with the carbon atom to which each is attached, form an optionally substituted $C_3$-$C_6$ cycloalkyl;

$R^6$ is optionally substituted $C_1$-$C_6$ alkyl or —$NR^7R^8$;

$R^7$ and $R^8$ are, independently, optionally substituted $C_1$-$C_6$ alkyl;

Het is optionally substituted 5-membered heteroarylene, optionally substituted 6-membered heteroarylene, or

[structure with F on benzene ring];

A is optionally substituted $C_6$-$C_{10}$ arylene, optionally substituted $C_2$-$C_9$ heterocyclylene, or optionally substituted $C_2$-$C_9$ heteroarylene;

L is absent, —O—, optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted $C_2$-$C_9$ heterocyclylene, optionally substituted $C_2$-$C_9$ heterocyclyl $C_1$-$C_6$ alkylene, optionally substituted $C_2$-$C_9$ heteroarylene, or optionally substituted $C_2$-$C_9$ heteroaryl $C_1$-$C_6$ alkylene; and B is H, halogen, cyano, optionally substituted $C_6$-$C_{10}$ aryl, optionally substituted $C_3$-$C_{10}$ cycloalkyl, optionally substituted $C_2$-$C_9$ heterocyclyl, or optionally substituted $C_2$-$C_9$ heteroaryl, or a pharmaceutically acceptable salt thereof.

In some embodiments,

is 6-membered heteroarylene. In some embodiments,

is 5-membered heteroarylene.

In some embodiments,

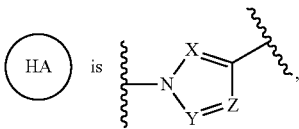

where each of X, Y, and Z is, independently, N or CH.

In some embodiments, the compound of Formula IV has the structure of Formula IVa:

Formula IVa

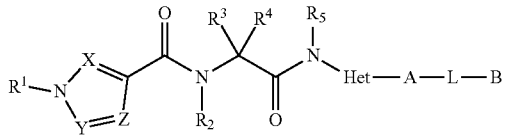

where each of X, Y, and Z is, independently, N or CH;
R$^1$ is H, optionally substituted C$_1$-C$_6$ acyl, optionally substituted C$_1$-C$_6$ alkyl, optionally substituted C$_1$-C$_6$ heteroalkyl, optionally substituted C$_3$-C$_8$ cycloalkyl, optionally substituted C$_2$-C$_9$ heterocyclyl, or —SO$_2$R$^6$;
each of R$^2$, R$^3$, and R$^5$ is, independently, H or optionally substituted C$_1$-C$_6$ alkyl;
R$^4$ is H, optionally substituted C$_1$-C$_6$ alkyl, or optionally substituted C$_1$-C$_6$ heteroalkyl;
R$^6$ is optionally substituted C$_1$-C$_6$ alkyl or —NR$^7$R$^8$;
each of R$^7$ and R$^8$ is, independently, optionally substituted C$_1$-C$_6$ alkyl;
Het is optionally substituted 5-membered heteroarylene, optionally substituted 6-membered heteroarylene, or

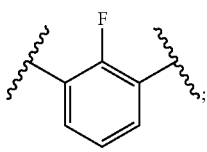 [SMILES: *c1cccc(*)c1F]

A is optionally substituted C$_6$-C$_{10}$ arylene, optionally substituted C$_2$-C$_9$ heterocyclylene, or optionally substituted C$_2$-C$_9$ heteroarylene;
L is absent, —O—, optionally substituted C$_1$-C$_6$ alkylene, optionally substituted C$_1$-C$_6$ heteroalkylene, optionally substituted C$_2$-C$_6$ alkenylene, optionally substituted C$_2$-C$_6$ heteroalkenylene, optionally substituted C$_2$-C$_6$ alkynylene, optionally substituted C$_2$-C$_6$ heteroalkynylene, optionally substituted C$_2$-C$_9$ heterocyclylene, optionally substituted C$_2$-C$_9$ heterocyclyl C$_1$-C$_6$ alkylene, optionally substituted C$_2$-C$_9$ heteroarylene, or optionally substituted C$_2$-C$_9$ heteroaryl C$_1$-C$_6$ alkylene; and
B is H, halogen, cyano, optionally substituted C$_6$-C$_{10}$ aryl, optionally substituted C$_3$-C$_{10}$ cycloalkyl, optionally substituted C$_2$-C$_9$ heterocyclyl, or optionally substituted C$_2$-C$_9$ heteroaryl, or a pharmaceutically acceptable salt thereof.

In some embodiments, X, Y, and Z are CH; X is N and Y and Z are CH; Z is N and X and Y are CH; Y is N and X and Z are CH; X is CH and Y and Z are N; Z is CH and X and y are N; Y is CH and X and Z are N; or X, Y, and Z are N.

In some embodiments, the compound of Formula IV has the structure of Formula IVb:

Formula IVb

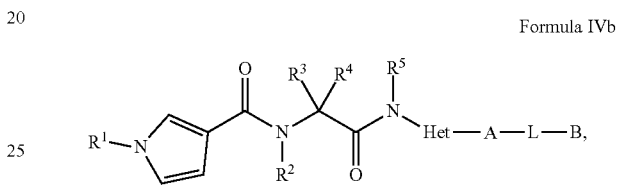

or a pharmaceutically acceptable salt thereof.

In some embodiments, the compound of Formula IV has the structure of Formula IVc:

Formula IVc

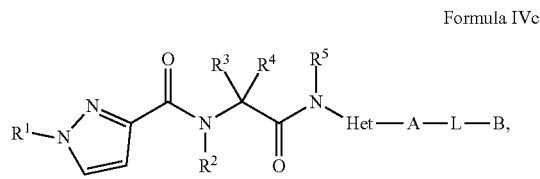

or a pharmaceutically acceptable salt thereof. In some embodiments, the compound of Formula IV has the structure of Formula Ic:

Formula IVd

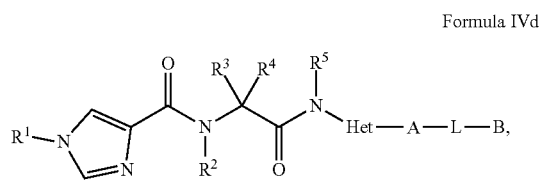

or a pharmaceutically acceptable salt thereof.

In some embodiments, the compound of Formula IV has the structure of Formula IVe:

Formula IVe

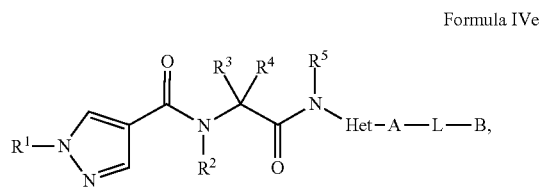

or a pharmaceutically acceptable salt thereof.

In some embodiments,

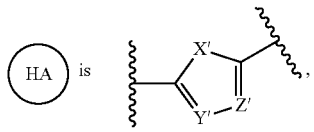

where X' is O or S; Y' is N or CH; and Z' is N or CH.

In some embodiments, the compound of Formula IVa has the structure of Formula V:

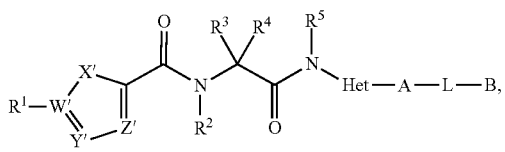

Formula V where
W is C or N;
X' is O, S, or N—CH3;
Y' is N or CH;
Z' is N or CH;
$R^1$ is absent, H, optionally substituted $C_1$-$C_6$ acyl, optionally substituted $C_1$-$C_6$ alkyl, optionally substituted $C_1$-$C_6$ heteroalkyl, optionally substituted $C_3$-$C_8$ cycloalkyl, optionally substituted $C_2$-$C_9$ heterocyclyl, or —$SO_2R^6$;
each of $R^2$, $R^3$, and $R^5$ is, independently, H or optionally substituted $C_1$-$C_6$ alkyl;
$R^4$ is H, optionally substituted $C_1$-$C_6$ alkyl, or optionally substituted $C_1$-$C_6$ heteroalkyl;
$R^6$ is optionally substituted $C_1$-$C_6$ alkyl or —$NR^7R^8$;
each of $R^7$ and $R^8$ is, independently, optionally substituted $C_1$-$C_6$ alkyl;
Het is optionally substituted 5-membered heteroarylene, optionally substituted 6-membered heteroarylene, or

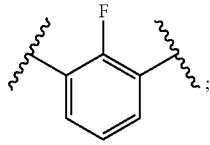 [SMILES: *c1cccc(*)c1F]

A is optionally substituted $C_6$-$C_{10}$ arylene, optionally substituted $C_2$-$C_9$ heterocyclylene, or optionally substituted $C_2$-$C_9$ heteroarylene;
L is absent, —O—, optionally substituted $C_1$-$C_6$ alkylene, optionally substituted $C_1$-$C_6$ heteroalkylene, optionally substituted $C_1$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted $C_2$-$C_9$ heterocyclylene, optionally substituted $C_2$-$C_9$ heterocyclyl $C_1$-$C_6$ alkylene, optionally substituted $C_2$-$C_9$ heteroarylene, or optionally substituted $C_2$-$C_9$ heteroaryl $C_1$-$C_6$ alkylene; and
B is H, halogen, cyano, optionally substituted $C_6$-$C_{10}$ aryl, optionally substituted $C_3$-$C_{10}$ cycloalkyl, optionally substituted $C_2$-$C_9$ heterocyclyl, or optionally substituted $C_2$-$C_9$ heteroaryl,
or a pharmaceutically acceptable salt thereof.

In some embodiments, X' is O, Y' is CH, and Z' is N; X' is S, Y' is CH, and Z' is N; X' is O, Y' is N, and Z' is CH; X' is S, Y' is N, and Z' is CH; X' is O, Y' is N, and Z' is N; or X' is S, Y' is N, and Z' is N.

In some embodiments, the compound of Formula V has the structure of Formula Va:

Formula Va

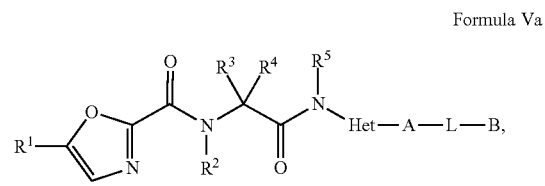

or a pharmaceutically acceptable salt thereof.

In some embodiments, the compound of Formula II has the structure of Formula Vb:

Formula Vb

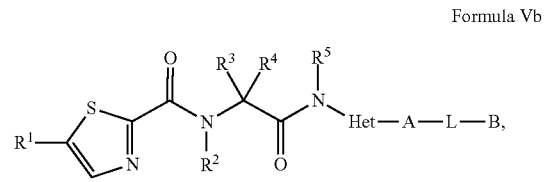

or a pharmaceutically acceptable salt thereof.

In some embodiments, the small molecule compound, or pharmaceutically acceptable salt thereof is any one of compounds 17-20 having the structure:

17

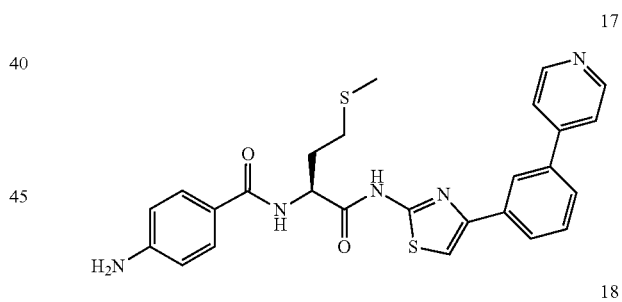

18

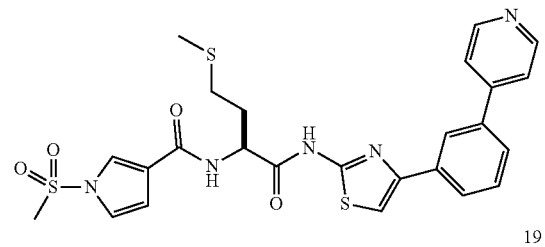

19

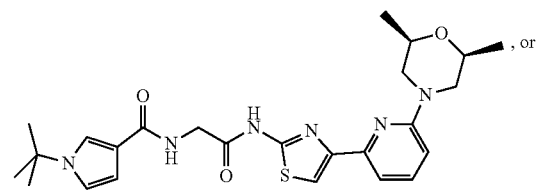

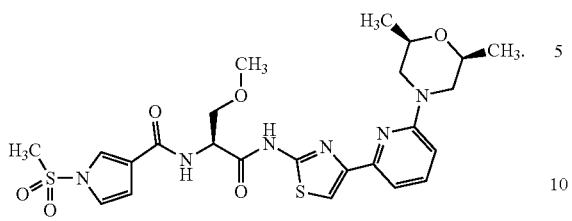

20

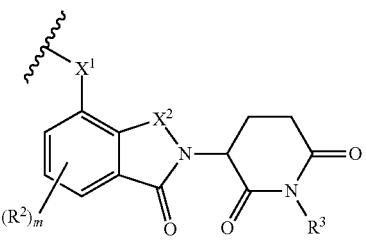

Formula A

In some embodiments, the small molecule compound, or a pharmaceutically acceptable salt thereof is a degrader. In some embodiments, the degrader has the structure of Formula VI:

C-L-D        Formula VI wherein C is a BRG1 and/or BRM binding moiety; L is a linker; and D is a degradation moiety, or a pharmaceutically acceptable salt thereof. In some embodiments, the degradation moiety is a ubiquitin ligase moiety. In some embodiments, the ubiquitin ligase binding moiety includes Cereblon ligands, IAP (Inhibitors of Apoptosis) ligands, mouse double minute 2 homolog (MDM2), hydrophobic tag, or von Hippel-Lindau ligands, or derivatives or analogs thereof.

In some embodiments, A includes the structure of any one of Formula I-V, or any one of compounds 1-20.

In some embodiments, the hydrophobic tag includes a diphenylmethane, adamantine, or tri-Boc arginine, i.e., the hydrophobic tag includes the structure:

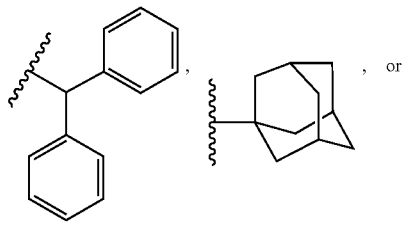

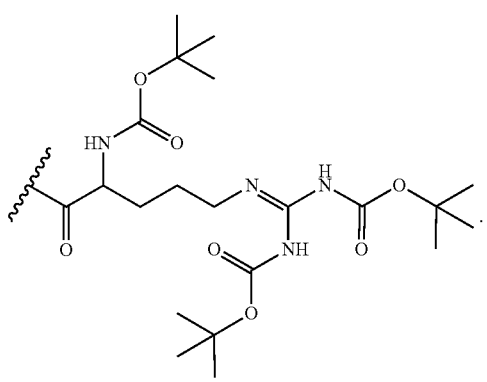

In some embodiments, the ubiquitin ligase binding moiety includes the structure of Formula A:

wherein $X^1$ is $CH_2$, O, S, or $NR^1$, wherein $R^1$ is H, optionally substituted $C_1$-$C_6$ alkyl, or optionally substituted $C_1$-$C_6$ heteroalkyl; $X^2$ is C=O, $CH_2$, or

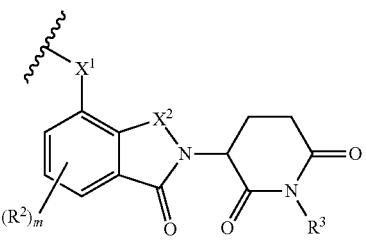

$R^3$ and $R^4$ are, independently, H, optionally substituted $C_1$-$C_6$ alkyl, or optionally substituted $C_1$-$C_6$ heteroalkyl; m is 0, 1, 2, 3, or 4; and each $R^2$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino, or a pharmaceutically acceptable salt thereof.

In some embodiments, the ubiquitin ligase binding moiety includes the structure:

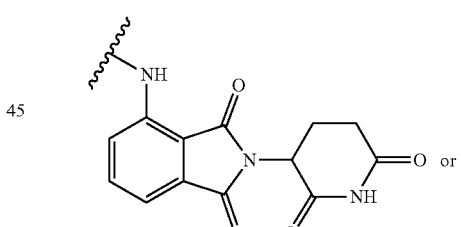

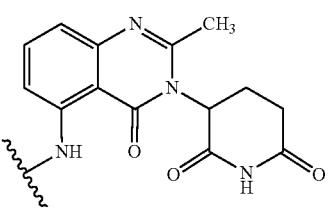

or is a derivative or an analog thereof, or a pharmaceutically acceptable salt thereof.

In some embodiments, the ubiquitin ligase binding moiety includes the structure of Formula B:

Formula B

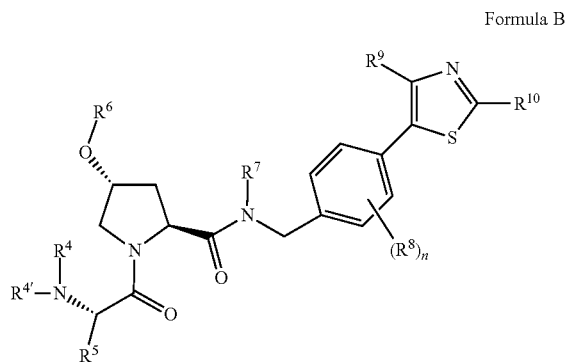

wherein each $R^4$, $R^{4'}$, and $R^7$ is, independently, H, optionally substituted $C_1$-$C_6$ alkyl, or optionally substituted $C_1$-$C_6$ heteroalkyl; $R^5$ is optionally substituted $C_1$-$C_6$ alkyl, optionally substituted $C_1$-$C_6$ heteroalkyl, optionally substituted $C_3$-$C_{10}$ carbocyclyl, optionally substituted $C_6$-$C_{10}$ aryl, optionally substituted $C_1$-$C_6$ alkyl $C_3$-$C_{10}$ carbocyclyl, or optionally substituted $C_1$-$C_6$ alkyl $C_6$-$C_{10}$ aryl; $R^6$ is H, optionally substituted $C_1$-$C_6$ alkyl, optionally substituted $C_3$-$C_{10}$ carbocyclyl, optionally substituted $C_6$-$C_{10}$ aryl, optionally substituted $C_1$-$C_6$ alkyl $C_3$-$C_{10}$ carbocyclyl, or optionally substituted $C_1$-$C_6$ alkyl $C_6$-$C_{10}$ aryl; n is 0, 1, 2, 3, or 4; each $R^8$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino; and each $R^9$ and $R^{10}$ is, independently, H, halogen, optionally substituted $C_1$-$C_6$ alkyl, or optionally substituted $C_6$-$C_{10}$ aryl, wherein $R^{4'}$ or $R^5$ includes a bond to the linker, or a pharmaceutically acceptable salt thereof.

In some embodiments, the ubiquitin ligase binding moiety includes the structure:

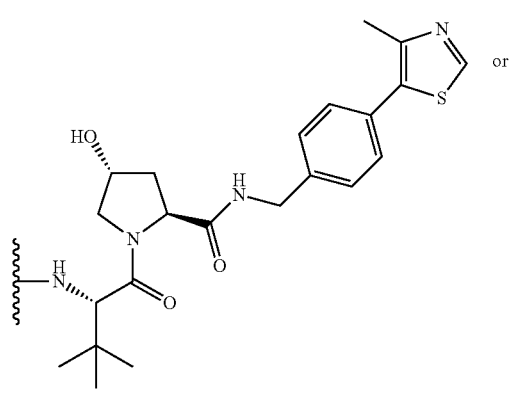 or

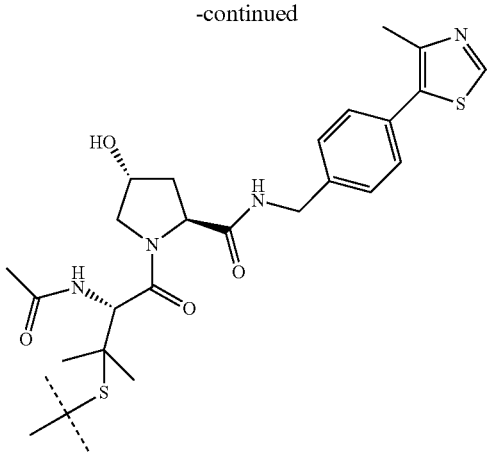

or is a derivative or analog thereof, or a pharmaceutically acceptable salt thereof.

In some embodiments, the ubiquitin ligase binding moiety includes the structure of Formula C:

Formula C

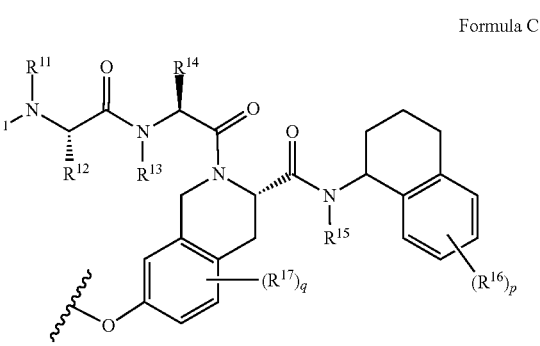

wherein each $R^{11}$, $R^{13}$, and $R^{15}$ is, independently, H, optionally substituted $C_1$-$C_6$ alkyl, or optionally substituted $C_1$-$C_6$ heteroalkyl; $R^{12}$ is optionally substituted $C_1$-$C_6$ alkyl, optionally substituted $C_3$-$C_{10}$ carbocyclyl, optionally substituted $C_6$-$C_{10}$ aryl, optionally substituted $C_1$-$C_6$ alkyl $C_3$-$C_{10}$ carbocyclyl, or optionally substituted $C_1$-$C_6$ alkyl $C_6$-$C_{10}$ aryl; $R^{14}$ is optionally substituted $C_1$-$C_6$ alkyl, optionally substituted $C_3$-$C_{10}$ carbocyclyl, optionally substituted $C_6$-$C_{10}$ aryl, optionally substituted $C_1$-$C_6$ alkyl $C_3$-$C_{10}$ carbocyclyl, or optionally substituted $C_1$-$C_6$ alkyl $C_6$-$C_{10}$ aryl; p is 0, 1, 2, 3, or 4; each $R^{16}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino; q is 0, 1, 2, 3, or 4; and each $R^{17}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino, or a pharmaceutically acceptable salt thereof.

In some embodiments, the ubiquitin ligase binding moiety includes the structure:

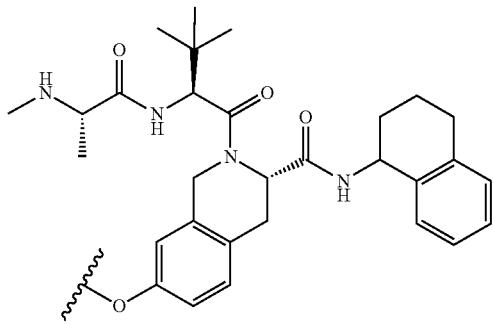 [SMILES: *Oc1ccc2c(c1)CN(C(=O)[C@@H](NC(=O)[C@H](C)NC)C(C)(C)C)[C@H](C(=O)NC1CCCc3ccccc31)C2]

or is a derivative or an analog thereof, or a pharmaceutically acceptable salt thereof.

In some embodiments, the ubiquitin ligase binding moiety includes the structure of Formula D:

Formula D

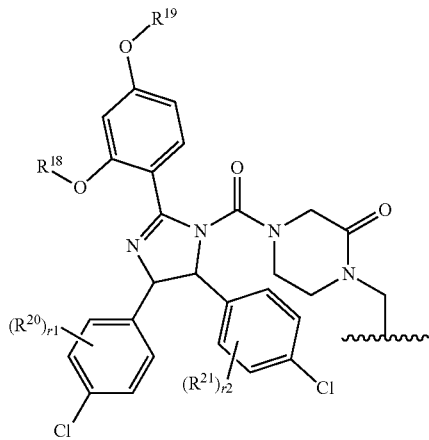

wherein each $R^{18}$ and $R^{19}$ is, independently, H, optionally substituted $C_1$-$C_6$ alkyl, optionally substituted $C_3$-$C_{10}$ carbocyclyl, optionally substituted $C_6$-$C_{10}$ aryl, optionally substituted $C_1$-$C_6$ alkyl $C_3$-$C_{10}$ carbocyclyl, or optionally substituted $C_1$-$C_6$ alkyl $C_6$-$C_{10}$ aryl; r1 is 0, 1, 2, 3, or 4; each $R^{20}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino; r2 is 0, 1, 2, 3, or 4; and each $R^{21}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino, or a pharmaceutically acceptable salt thereof.

In some embodiments, the ubiquitin ligase binding moiety includes the structure:

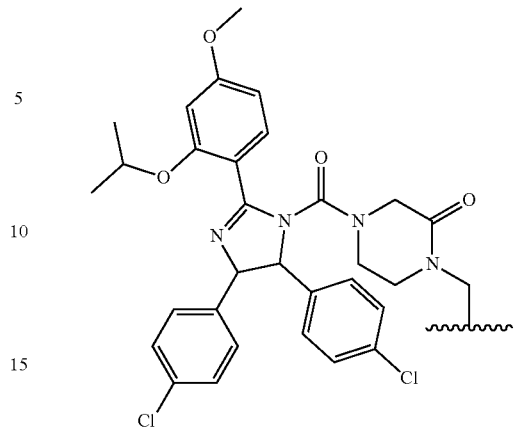

or is a derivative or an analog thereof, or a pharmaceutically acceptable salt thereof.

In some embodiments, the linker has the structure of Formula VII:

$$A^1\text{-}(B^1)_f\text{—}(C^1)_g\text{—}(B^2)_h\text{-}(D)\text{-}(B^3)_i\text{—}(C^2)_j\text{—}(B^4)_k\text{-}A^2 \quad \text{Formula VII}$$

wherein $A^1$ is a bond between the linker and A; $A^2$ is a bond between B and the linker; $B^1$, $B^2$, $B^3$, and $B^4$ each, independently, is selected from optionally substituted $C_1$-$C_2$ alkyl, optionally substituted $C_1$-$C_3$ heteroalkyl, O, S, $S(O)_2$, and $NR^N$; $R^N$ is hydrogen, optionally substituted $C_{1-4}$ alkyl, optionally substituted $C_{2-4}$ alkenyl, optionally substituted $C_{2-4}$ alkynyl, optionally substituted $C_{2-6}$ heterocyclyl, optionally substituted $C_{6-12}$ aryl, or optionally substituted $C_{1-7}$ heteroalkyl; $C^1$ and $C^2$ are each, independently, selected from carbonyl, thiocarbonyl, sulphonyl, or phosphoryl; f, g, h, l, j, and k are each, independently, 0 or 1; and D is optionally substituted $C_{1-10}$ alkyl, optionally substituted $C_{2-10}$ alkenyl, optionally substituted $C_{2-10}$ alkynyl, optionally substituted $C_{2-6}$ heterocyclyl, optionally substituted $C_B$-12 aryl, optionally substituted $C_2$-$C_{10}$ polyethylene glycol, or optionally substituted $C_{1-10}$ heteroalkyl, or a chemical bond linking $A^1\text{-}(B^1)_f\text{—}(C^1)_g\text{—}(B^2)_h\text{—}$ to $\text{—}(B^3)_i\text{—}(C^2)_j\text{—}(B^4)_k\text{-}A^2$.

In some embodiments, D is optionally substituted $C_2$-$C_{10}$ polyethylene glycol. In some embodiments, $C^1$ and $C^2$ are each, independently, a carbonyl or sulfonyl. In some embodiments, $B^1$, $B^2$, $B^3$, and $B^4$ each, independently, is selected from optionally substituted $C_1$-$C_2$ alkyl, optionally substituted $C_1$-$C_3$ heteroalkyl, O, S, $S(O)_2$, and $NR^N$; $R^N$ is hydrogen or optionally substituted $C_{1-4}$ alkyl. In some embodiments, $B^1$, $B^2$, $B^3$, and $B^4$ each, independently, is selected from optionally substituted $C_1$-$C_2$ alkyl or optionally substituted $C_1$-$C_3$ heteroalkyl. In some embodiments, j is 0. In some embodiments, k is 0. In some embodiments, j and k are each, independently, 0. In some embodiments, f, g, h, and i are each, independently, 1.

In some embodiments, the linker of Formula VII has the structure of Formula VIIa:

Formula VIIa

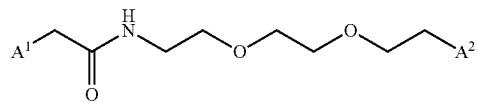

wherein $A^1$ is a bond between the linker and A, and $A^2$ is a bond between B and the linker.

In some embodiments, D is optionally substituted $C_{1-10}$ alkyl. In some embodiments, $C^1$ and $C^2$ are each, independently, a carbonyl. In some embodiments, $B^1$, $B^2$, $B^3$, and $B^4$ each, independently, is selected from optionally substituted $C_1$-$C_2$ alkyl, optionally substituted $C_1$-$C_3$ heteroalkyl, O, S, $S(O)_2$, and $NR^N$, wherein $R^N$ is hydrogen or optionally substituted $C_{1-4}$ alkyl. In some embodiments, $B^1$, $B^2$, $B^3$, and $B^4$ each, independently, is selected from optionally substituted $C_1$-$C_2$ alkyl, O, S, $S(O)_2$, and $NR^N$, wherein $R^N$ is hydrogen or optionally substituted $C_{1-4}$ alkyl. In some embodiments, $B^1$ and $B^4$ each, independently, is optionally substituted $C_1$-$C_2$ alkyl. In some embodiments, $B^1$ and $B^4$ each, independently, is $C_1$ alkyl. In some embodiments, $B^2$ and $B^4$ each, independently, is $NR^N$, wherein $R^N$ is hydrogen or optionally substituted $C_{1-4}$ alkyl. In some embodiments, $B^2$ and $B^4$ each, independently, is NH. In some embodiments, f, g, h, l, j, and k are each, independently, 1.

In some embodiments, the linker of Formula V has the structure of Formula VIIb:

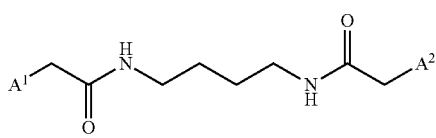

Formula VIIb wherein $A^1$ is a bond between the linker and A, and $A^2$ is a bond between B and the linker.

Pharmaceutical Uses

The compounds described herein are useful in the methods of the invention and, while not bound by theory, are believed to exert their desirable effects through their ability to modulate the level, status, and/or activity of a BAF complex, e.g., by inhibiting the activity or level of the BRG1 and/or BRM proteins in a cell within the BAF complex in a mammal.

An aspect of the present invention relates to methods of treating disorders related to BRG1 and/or BRM proteins such as AML in a subject in need thereof. In some embodiments, the compound is administered in an amount and for a time effective to result in one of (or more, e.g., two or more, three or more, four or more of): (a) reduced tumor size, (b) reduced rate of tumor growth, (c) increased tumor cell death (d) reduced tumor progression, (e) reduced number of metastases, (f) reduced rate of metastasis, (g) decreased tumor recurrence (h) increased survival of subject, and (i) increased progression free survival of a subject.

Treating cancer can result in a reduction in size or volume of a tumor. For example, after treatment, tumor size is reduced by 5% or greater (e.g., 10%, 20%, 30%, 40%, 50%, 60%, 70%, 80%, 90%, or greater) relative to its size prior to treatment. Size of a tumor may be measured by any reproducible means of measurement. For example, the size of a tumor may be measured as a diameter of the tumor.

Treating cancer may further result in a decrease in number of tumors. For example, after treatment, tumor number is reduced by 5% or greater (e.g., 10%, 20%, 30%, 40%, 50%, 60%, 70%, 80%, 90%, or greater) relative to number prior to treatment. Number of tumors may be measured by any reproducible means of measurement, e.g., the number of tumors may be measured by counting tumors visible to the naked eye or at a specified magnification (e.g., 2×, 3×, 4×, 5×, 10×, or 50×).

Treating cancer can result in a decrease in number of metastatic nodules in other tissues or organs distant from the primary tumor site (e.g., in the liver). For example, after treatment, the number of metastatic nodules is reduced by 5% or greater (e.g., 10%, 20%, 30%, 40%, 50%, 60%, 70%, 80%, 90% or greater) relative to number prior to treatment. The number of metastatic nodules may be measured by any reproducible means of measurement. For example, the number of metastatic nodules may be measured by counting metastatic nodules visible to the naked eye or at a specified magnification (e.g., 2×, 10×, or 50×).

Treating cancer can result in inhibition or slowing of the metastatic progression of the cancer. For example, a patient may be administered an amount of an agent that reduces the activity or level of the BRG1 and/or BRM that is effective to inhibit metastasis of the cancer to other parts of the body (e.g., a patient having uveal melanoma that has metastasized (e.g., to the liver)). An agent may be administered in an adjuvant or neo-adjuvant setting, such as prior to or subsequent to surgical rescission of the cancer, and result in a decrease incidence of metastasis of the cancer.

Treating cancer can result in an increase in average survival time of a population of subjects treated according to the present invention in comparison to a population of untreated subjects. For example, the average survival time is increased by more than 30 days (more than 60 days, 90 days, or 120 days). An increase in average survival time of a population may be measured by any reproducible means. An increase in average survival time of a population may be measured, for example, by calculating for a population the average length of survival following initiation of treatment with the compound described herein. An increase in average survival time of a population may also be measured, for example, by calculating for a population the average length of survival following completion of a first round of treatment with a pharmaceutically acceptable salt of a compound described herein.

Treating cancer can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with a pharmaceutically acceptable salt of a compound described herein. A decrease in the mortality rate of a population may also be measured, for example, by calculating for a population the average number of disease-related deaths per unit time following completion of a first round of treatment with a pharmaceutically acceptable salt of a compound described herein.

Combination Therapies

A method of the invention can be used alone or in combination with an additional therapeutic agent, e.g., other agents that treat cancer or symptoms associated therewith, or in combination with other types of therapies to treat cancer. In combination treatments, the dosages of one or more of the therapeutic compounds may be reduced from standard dosages when administered alone. For example, doses may be determined empirically from drug combinations and permutations or may be deduced by isobolographic analysis (e.g., Black et al., *Neurology* 65:S3-S6 (2005)). In this case, dosages of the compounds when combined should provide a therapeutic effect.

In some embodiments, the second therapeutic agent is a chemotherapeutic agent (e.g., a cytotoxic agent or other chemical compound useful in the treatment of cancer). These include alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel, and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., *Agnew, Chem. Intl. Ed Engl.* 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin, including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, NJ), ABRAXANE®, cremophor-free, albumin-engineered nanoparticle formulation of paclitaxel (American Pharmaceutical Partners, Schaumberg, IL), and TAXOTERE® doxetaxel (Rhone-Poulenc Rorer, Antony, France); chloranbucil; GEMZAR® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above. Two or more chemotherapeutic agents can be used in a cocktail to be administered in combination with the first therapeutic agent described herein. Suitable dosing regimens of combination chemotherapies are known in the art and described in, for example, Saltz et al., *Proc. Am. Soc. Clin. Oncol.* 18:233a (1999), and Douillard et al., *Lancet* 355(9209):1041-1047 (2000).

In some embodiments, the second therapeutic agent is a therapeutic agent which is a biologic such a cytokine (e.g., interferon or an interleukin (e.g., IL-2)) used in cancer treatment. In some embodiments the biologic is an anti-angiogenic agent, such as an anti-VEGF agent, e.g., bevacizumab (AVASTIN®). In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen important for cancer. Such agents include RITUXAN® (rituximab); ZENAPAX® (daclizumab); SIMULECT® (basiliximab); SYNAGIS® (palivizumab); REMICADE® (infliximab); HERCEPTIN® (trastuzumab); MYLOTARG® (gemtuzumab ozogamicin); CAMPATH® (alemtuzumab); ZEVALIN® (ibritumomab tiuxetan); HUMIRA® (adalimumab); XOLAIR® (omalizumab); BEXXAR® (tositumomab-1-131); RAPTIVA® (efalizumab); ERBITUX® (cetuximab); AVASTIN® (bevacizumab); TYSABRI® (natalizumab); ACTEMRA® (tocilizumab); VECTIBIX® (panitumumab); LUCENTIS® (ranibizumab); SOLIRIS® (eculizumab); CIMZIA® (certolizumab pegol); SIMPONI® (golimumab); ILARIS® (canakinumab); STELARA® (ustekinumab); ARZERRA® (ofatumumab); PROLIA® (denosumab); NUMAX® (motavizumab); ABTHRAX® (raxibacumab); BENLYSTA® (belimumab); YERVOY® (ipilimumab); ADCETRIS® (brentuximab vedotin); PERJETA® (pertuzumab); KADCYLA® (ado-trastuzumab emtansine); and GAZYVA® (obinutuzumab). Also included are antibody-drug conjugates.

In some embodiments, the second agent is dacarbazine, temozolomide, cisplatin, treosulfan, fotemustine, IMCgp100, a CTLA-4 inhibitor (e.g., ipilimumab), a PD-1 inhibitor (e.g., Nivolumab or pembrolizumab), a PD-L1 inhibitor (e.g., atezolizumab, avelumab, or durvalumab), a mitogen-activated protein kinase (MEK) inhibitor (e.g., selumetinib, binimetinib, or tametinib), and/or a protein kinase C (PKC) inhibitor (e.g., sotrastaurin or LXS196).

In some embodiments, the second agent is a mitogen-activated protein kinase (MEK) inhibitor (e.g., selumetinib, binimetinib, or tametinib) and/or a protein kinase C (PKC) inhibitor (e.g., sotrastaurin or LXS196).

In some embodiments, the second agent is cytarabine, an anthracycline such as daunorubicin, arsenic trioxide, all-trans-retinoic acid, or a combination thereof. In some embodiments, the second agent is an immunotherapy such as histamine dihydrochloride and interleukin 2. In some embodiments, the second agent is gemtuzumab ozogamicin.

The second agent may be a therapeutic agent which is a non-drug treatment. For example, the second therapeutic agent is radiation therapy, thermotherapy, photocoagulation, cryotherapy, hyperthermia, surgical excision of tumor, and/or a stem cell transplant (e.g., an allogenic stem cell transplant or hemapoietic stem cell transplant).

The second agent may be a checkpoint inhibitor. In one embodiment, the inhibitor of checkpoint is an inhibitory antibody (e.g., a monospecific antibody such as a monoclonal antibody). The antibody may be, e.g., humanized or fully human. In some embodiments, the inhibitor of checkpoint is a fusion protein, e.g., an Fc-receptor fusion protein. In some embodiments, the inhibitor of checkpoint is an agent, such as an antibody, that interacts with a checkpoint protein. In some embodiments, the inhibitor of checkpoint is an agent, such as an antibody, that interacts with the ligand of a checkpoint protein. In some embodiments, the inhibitor of checkpoint is an inhibitor (e.g., an inhibitory antibody or small molecule inhibitor) of CTLA-4 (e.g., an anti-CTLA4 antibody or fusion a protein such as ipilimumab/YERVOY® or tremelimumab). In some embodiments, the inhibitor of checkpoint is an inhibitor (e.g., an inhibitory antibody or small molecule inhibitor) of PD-1 (e.g., nivolumab/OPDIVO®; pembrolizumab/KEYTRUDA®; pidilizumab/CT-011). In some embodiments, the inhibitor of checkpoint is an inhibitor (e.g., an inhibitory antibody or small molecule inhibitor) of PDL1 (e.g., atezolizumab, avelumab, durvalumab, MPDL3280A/RG7446; MEDI4736; MSB0010718C; BMS 936559). In some embodiments, the inhibitor of checkpoint is an inhibitor (e.g., an inhibitory antibody or Fc fusion or small molecule inhibitor) of PDL2 (e.g., a PDL2/Ig fusion protein such as AMP 224). In some embodiments, the inhibitor of checkpoint is an inhibitor (e.g., an inhibitory antibody or small molecule inhibitor) of B7-H3 (e.g., MGA271), B7-H4, BTLA, HVEM, TIM3, GAL9, LAG3, VISTA, KIR, 2B4, CD160, CGEN-15049, CHK 1, CHK2, A2aR, B-7 family ligands, or a combination thereof.

In some embodiments, the anti-cancer therapy is a T cell adoptive transfer (ACT) therapy. In some embodiments, the T cell is an activated T cell. The T cell may be modified to express a chimeric antigen receptor (CAR). CAR modified T (CAR-T) cells can be generated by any method known in the art. For example, the CAR-T cells can be generated by introducing a suitable expression vector encoding the CAR to a T cell. Prior to expansion and genetic modification of the T cells, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In some embodiments, the T cell is an autologous T cell. Whether prior to or after genetic modification of the T cells to express a desirable protein (e.g., a CAR), the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

In any of the combination embodiments described herein, the first and second therapeutic agents are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

Delivery of Anti-BRG1 and/or BRM Agents

A variety of methods are available for the delivery of anti-BRG1 and/or BRM agents to a subject including viral and non-viral methods.

Viral Delivery Methods

In some embodiments, the agent that reduces the level and/or activity of BRG1 and/or BRM is delivered by a viral vector (e.g., a viral vector expressing an anti-BRG1 and/or BRM agent). Viral genomes provide a rich source of vectors that can be used for the efficient delivery of exogenous genes into a mammalian cell. Viral genomes are particularly useful vectors for gene delivery because the polynucleotides contained within such genomes are typically incorporated into the nuclear genome of a mammalian cell by generalized or specialized transduction. These processes occur as part of the natural viral replication cycle, and do not require added proteins or reagents in order to induce gene integration. Examples of viral vectors include a retrovirus (e.g., Retroviridae family viral vector), adenovirus (e.g., Ad5, Ad26, Ad34, Ad35, and Ad48), parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g., measles and Sendai), positive strand RNA viruses, such as picornavirus and alphavirus, and double-stranded DNA viruses including adenovirus, herpesvirus (e.g., Herpes Simplex virus types 1 and 2, Epstein-Barr virus, cytomegalovirus, replication deficient herpes virus), and poxvirus (e.g., vaccinia, modified vaccinia Ankara (MVA), fowlpox and canarypox). Other viruses include Norwalk virus, togavirus, flavivirus, reoviruses, papovavirus, hepadnavirus, human papilloma virus, human foamy virus, and hepatitis virus, for example. Examples of retroviruses include: avian leukosis-sarcoma, avian C-type viruses, mammalian C-type, B-type viruses, D-type viruses, oncoretroviruses, HTLV-BLV group, lentivirus, alpharetrovirus, gammaretrovirus, spumavirus (Coffin, J. M., Retroviridae: The viruses and their replication, Virology (Third Edition) Lippincott-Raven, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in U.S. Pat. No. 5,801,030, the teachings of which are incorporated herein by reference.

Exemplary viral vectors include lentiviral vectors, AAVs, and retroviral vectors. Lentiviral vectors and AAVs can integrate into the genome without cell divisions, and both types have been tested in pre-clinical animal studies. Methods for preparation of AAVs are described in the art e.g., in U.S. Pat. Nos. 5,677,158, 6,309,634, and 6,683,058, each of which is incorporated herein by reference. Methods for preparation and in vivo administration of lentiviruses are described in US 20020037281 (incorporated herein by reference). Preferably, a lentiviral vector is a replication-defective lentivirus particle. Such a lentivirus particle can be produced from a lentiviral vector comprising a 5' lentiviral LTR, a tRNA binding site, a packaging signal, a promoter operably linked to a polynucleotide signal encoding the fusion protein, an origin of second strand DNA synthesis and a 3' lentiviral LTR.

Retroviruses are most commonly used in human clinical trials, as they carry 7-8 kb, and have the ability to infect cells and have their genetic material stably integrated into the host cell with high efficiency (see, e.g., WO 95/30761; WO 95/24929, each of which is incorporated herein by reference). Preferably, a retroviral vector is replication defective. This prevents further generation of infectious retroviral particles in the target tissue. Thus, the replication defective virus becomes a "captive" transgene stable incorporated into the target cell genome. This is typically accomplished by deleting the gag, env, and pol genes (along with most of the rest of the viral genome). Heterologous nucleic acids are inserted in place of the deleted viral genes. The heterologous genes may be under the control of the endogenous heterologous promoter, another heterologous promoter active in the target cell, or the retroviral 5' LTR (the viral LTR is active in diverse tissues).

These delivery vectors described herein can be made target-specific by attaching, for example, a sugar, a glycolipid, or a protein (e.g., an antibody to a target cell receptor).

Reversible delivery expression systems may also be used. The Cre-loxP or FLP/FRT system and other similar systems can be used for reversible delivery-expression of one or more of the above-described nucleic acids. See WO2005/112620, WO2005/039643, US20050130919, US20030022375, US20020022018, US20030027335, and US20040216178. In particular, the reversible delivery-expression system described in US20100284990 can be used to provide a selective or emergency shut-off.

Non-Viral Delivery Methods

Several non-viral methods exist for delivery of anti-BRG1 and/or BRM agents including polymeric, biodegradable microparticle, or microcapsule delivery devices known in the art. For example, a colloidal dispersion system may be used for targeted delivery an anti-BRG1 and/or BRM agent described herein. Colloidal dispersion systems include macromolecule complexes, nanocapsules, microspheres, beads, and lipid-based systems including oil-in-water emulsions, micelles, mixed micelles, and liposomes. Liposomes are artificial membrane vesicles that are useful as delivery vehicles in vitro and in vivo. It has been shown that large unilamellar vesicles (LUV), which range in size from 0.2-4.0 µm can encapsulate a substantial percentage of an aqueous buffer containing large macromolecules.

The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Lipids useful in liposome production include phosphatidyl compounds, such as phosphatidylglycerol, phosphatidylcholine, phosphatidylserine, phosphatidyl-ethanolamine, sphingolipids, cerebrosides, and gangliosides. Exemplary phospholipids include egg phosphatidylcholine, dipalmitoylphosphatidylcholine, and distearoyl-phosphatidylcholine. The targeting of liposomes is also possible based on, for example, organ-specificity, cell-specificity, and organelle-specificity and is known in the art. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Additional methods are known in the art and are described, for example in U.S. Patent Application Publication No. 20060058255.

Pharmaceutical Compositions

The pharmaceutical compositions described herein are preferably formulated into pharmaceutical compositions for administration to human subjects in a biologically compatible form suitable for administration in vivo.

The compounds described herein may be used in the form of the free base, in the form of salts, solvates, and as prodrugs. All forms are within the methods described herein. In accordance with the methods of the invention, the described compounds or salts, solvates, or prodrugs thereof may be administered to a patient in a variety of forms depending on the selected route of administration, as will be understood by those skilled in the art. The compounds described herein may be administered, for example, by oral, parenteral, buccal, sublingual, nasal, rectal, patch, pump, intratumoral, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound described herein may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound described herein may be incorporated with an excipient and used in the form of ingestible tablets, buccal tablets, troches, capsules, elixirs, suspensions, syrups, and wafers. A compound described herein may also be administered parenterally. Solutions of a compound described herein can be prepared in water suitably mixed with a surfactant, such as hydroxypropylcellulose. Dispersions can also be prepared in glycerol, liquid polyethylene glycols, DMSO, and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2012, 22nd ed.) and in The United States Pharmacopeia: The National Formulary (USP 41 NF36), published in 2018. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe. Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form includes an aerosol dispenser, it will contain a propellant, which can be a compressed gas, such as compressed air or an organic propellant, such as fluorochlorohydrocarbon. The aerosol dosage forms can also take the form of a pump-atomizer. Compositions suitable for buccal or sublingual administration include tablets, lozenges, and pastilles, where the active ingredient is formulated with a carrier, such as sugar, acacia, tragacanth, gelatin, and glycerine. Compositions for rectal administration are conveniently in the form of suppositories containing a conventional suppository base, such as cocoa butter. A compound described herein may be administered intratumorally, for example, as an intratumoral injection. Intratumoral injection is injection directly into the tumor vasculature and is specifically contemplated for discrete, solid, accessible tumors. Local, regional, or systemic administration also may be appropriate. A compound described herein may advantageously be contacted by administering an injection or multiple injections to the tumor, spaced for example, at approximately, 1 cm intervals. In the case of surgical intervention, the present invention may be used preoperatively, such as to render an inoperable tumor subject to resection. Continuous administration also may be applied where appropriate, for example, by implanting a catheter into a tumor or into tumor vasculature.

The compounds described herein may be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

Dosages

The dosage of the compounds described herein, and/or compositions including a compound described herein, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds described herein may be administered initially in a suitable dosage that may be adjusted as required, depending on the clinical response. In general, satisfactory results may be obtained when the compounds described herein are administered to a human at a daily dosage of, for example, between 0.05 mg and 3000 mg (measured as the solid form).

Alternatively, the dosage amount can be calculated using the body weight of the patient. For example, the dose of a compound, or pharmaceutical composition thereof, administered to a patient may range from 0.1-50 mg/kg.

Kits

The invention also features kits including (a) a pharmaceutical composition including an agent that reduces the level and/or activity of BRG1 and/or BRM in a cell or subject described herein, and (b) a package insert with instructions to perform any of the methods described herein. In some embodiments, the kit includes (a) a pharmaceutical composition including an agent that reduces the level and/or activity of BRG1 and/or BRM in a cell or subject described herein, (b) an additional therapeutic agent (e.g., an anti-cancer agent), and (c) a package insert with instructions to perform any of the methods described herein.

EXAMPLES

Example 1. Compound 17

Synthesis of Compound 17: BRG1/BRM Inhibitor Compound 17 has the Structure

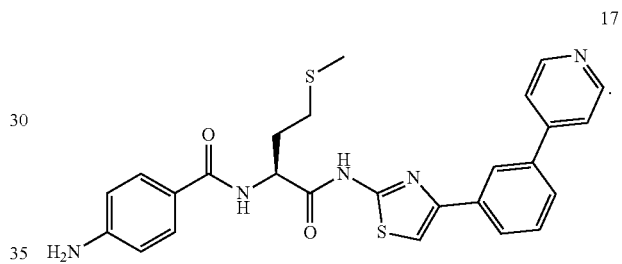

Compound 17 was synthesized as shown in Scheme 1 below.

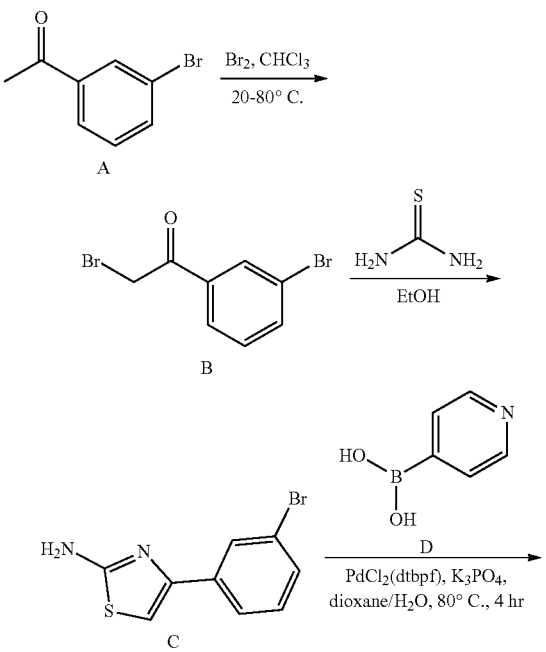

-continued

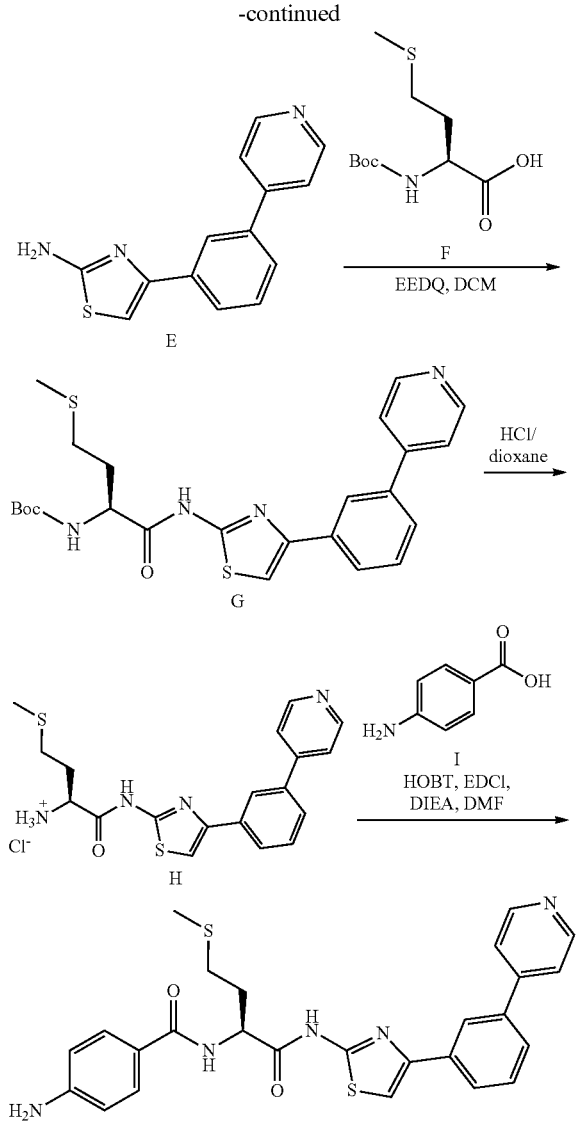

Step 2: Preparation of 4-(3-bromophenyl)thiazol-2-amine (Intermediate C)

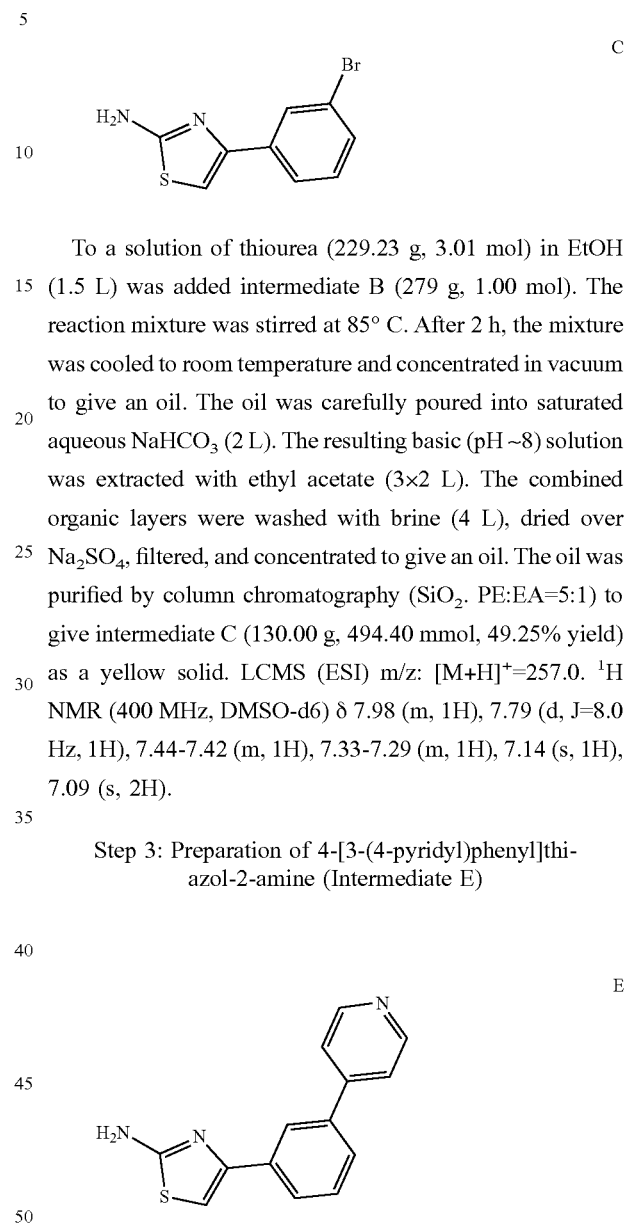

To a solution of thiourea (229.23 g, 3.01 mol) in EtOH (1.5 L) was added intermediate B (279 g, 1.00 mol). The reaction mixture was stirred at 85° C. After 2 h, the mixture was cooled to room temperature and concentrated in vacuum to give an oil. The oil was carefully poured into saturated aqueous NaHCO$_3$ (2 L). The resulting basic (pH ~8) solution was extracted with ethyl acetate (3×2 L). The combined organic layers were washed with brine (4 L), dried over Na$_2$SO$_4$, filtered, and concentrated to give an oil. The oil was purified by column chromatography (SiO$_2$. PE:EA=5:1) to give intermediate C (130.00 g, 494.40 mmol, 49.25% yield) as a yellow solid. LCMS (ESI) m/z: [M+H]$^+$=257.0. $^1$H NMR (400 MHz, DMSO-d6) δ 7.98 (m, 1H), 7.79 (d, J=8.0 Hz, 1H), 7.44-7.42 (m, 1H), 7.33-7.29 (m, 1H), 7.14 (s, 1H), 7.09 (s, 2H).

Step 3: Preparation of 4-[3-(4-pyridyl)phenyl]thiazol-2-amine (Intermediate E)

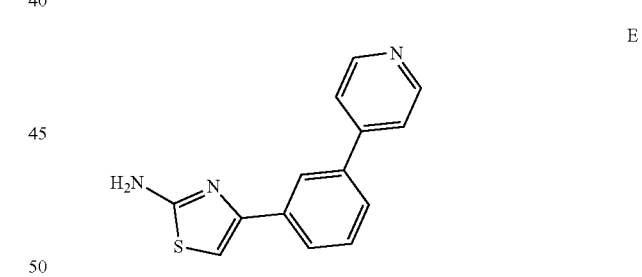

Intermediate C (20.00 g, 78.40 mmol), 4-pyridylboronic acid (28.9 g, 239.18 mmol), dichloro[1,1'-bis(di-t-butylphosphino)ferrocene]palladium(II) (2.56 g, 3.92 mmol) and K$_3$PO$_4$ (66.56 g, 313.56 mmol) were diluted in 1,4-dioxane (240 mL) and water (24 mL). The mixture was purged with N$_2$ (g) three times and then stirred at 80° C. After 7 h, the reaction mixture was cooled to room temperature and water (800 mL) was added. The mixture was extracted with EtOAc (3×800 mL). The combined organic layers were washed with brine, dried over anhydrous Na$_2$SO$_4$, filtered, and concentrated in vacuo. The resulting oil was stirred over a mixture of dichoromethane (30 mL) and MTBE (100 mL). After stirring for 5 min, the precipitate was filtered and washed with MTBE (10 mL) to give intermediate E (16.20 g, 61.17 mmol, 78.03% yield) as a yellow solid. LCMS (ESI) m/z: [M+H]$^+$=254.0.

Step 1: Preparation of 2-bromo-1-(3-bromophenyl)ethenone (Intermediate B)

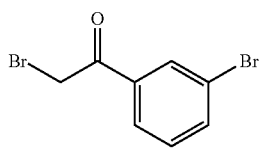

To a solution of 1-(3-bromophenyl)ethanone (132.45 mL, 1.00 mol) in CHCl$_3$ (250 mL) was added Br$_2$ (77.70 mL, 1.51 mol) in a dropwise manner at 20° C. under N$_2$ (g). The reaction mixture was subsequently stirred at 80° C. After 1 h, the mixture was cooled to room temperature and concentrated to give intermediate B (279.27 g) as yellow oil, which was used for next step directly.

Step 4: Preparation (S)-4-(methylthio)-1-oxo-1-((4-(3-(pyridin-4-yl)phenyl)thiazol-2-yl)amino)butan-2-aminium chloride (Intermediate G)

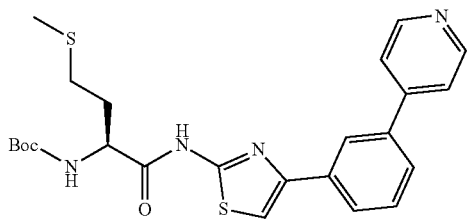

G

To a mixture of intermediate E (12.60 g, 49.74 mmol) and (2S)-2-(tert-butoxycarbonylamino)-4-methylsulfanyl-butanoic acid (18.60 g, 74.61 mmol) in dicholromethane (900 mL) was added EEDQ (24.60 g, 99.48 mmol). After stirring for 2 h at room temperature, the reaction mixture was concentrated in vacuo. The residue was triturated with dichloromethane (100 mL) followed by MeOH (200 mL) to give the intermediate G (11.70 g, 23.73 mmol, 47.71% yield, ee %=99.44%) as white solids. LCMS (ESI) m/z: [M+H]$^+$ =485.1. $^1$H NMR (400 MHz, DMSO) δ 12.39 (s, 1H), 8.68-8.66 (m, 2H), 8.30 (s, 1H), 8.02-7.99 (m, 1H), 7.83 (s, 1H), 7.76-7.74 (m, 3H), 7.61-7.57 (m, 1H), 7.28 (d, J=7.6 Hz, 1H), 4.31-4.30 (m, 1H), 2.65-2.44 (m, 2H), 2.06 (s, 3H) 2.01-1.85 (m, 2H), 1.38 (s, 9H).

Step 5: Preparation of (S)-4-(methylthio)-1-oxo-1-((4-(3-(pyridin-4-yl)phenyl)thiazol-2-yl)amino)butan-2-aminium chloride (Intermediate H)

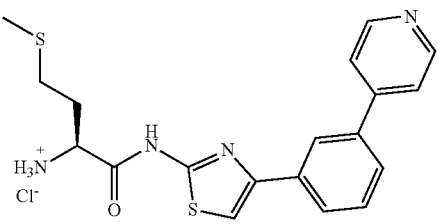

H

A mixture of intermediate G (11.50 g, 23.73 mmol) in MeOH (50 mL) was added a solution of 4 M HCl in 1,4-dioxane (100 mL). After stirring for 1 h at room temperature, the mixture was poured into MTBE (1000 mL). The resulting precipitates were filtered to give the intermediate H (9.99 g, 23.73 mmol, 100.00% yield, HCl salt) as a yellow solid. LCMS (ESI) m/z: [M+H]$^+$=385.0

Step 6: Preparation of 4-amino-N-[(1S)-3-methyl-sulfanyl-1-[[4-[3-(4-pyridyl)phenyl]thiazol-2-yl]carbamoyl]propyl]benzamide (compound 17)

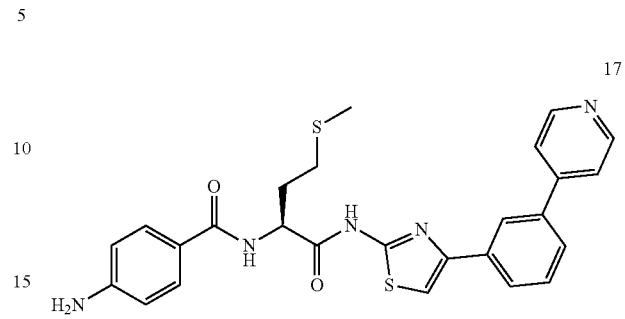

17

To a mixture of intermediate H (4.00 g, 9.50 mmol) and 4-aminobenzoic acid (1.30 g, 9.50 mmol) in DMF (40 mL) was sequentially added N,N-diisopropylethylamine (6.62 mL, 38.01 mmol), EDCl (2.73 g, 14.25 mmol) and HOBt (1.93 g, 14.25 mmol). The solution was stirred at 25° C. for 14 h and subsequently poured into water (200 mL). The resulting precipitates were collected by filtration. The solids were triturated in MeOH (200 mL) and filtered The solids were further purified by column chromatography (SiO$_2$, DCM:MeOH=80:1-20:1) to give compound 17 (2.13 g, 4.19 mmol, 44.11% yield, ee %=99.28%) as white solids. LCMS (ESI) m/z: [M+H]$^+$=504.0. $^1$H NMR (400 MHz, DMSO) δ 12.40 (s, 1H), 8.68-8.66 (m, 2H), 8.31-8.30 (m, 1H), 8.22 (d, J=7.2 Hz, 1H), 8.02-7.99 (m, 1H), 7.82 (s, 1H), 7.76-7.74 (m, 3H), 7.67-7.63 (m, 2H), 7.61-7.57 (m, 1H), 6.58-6.54 (m, 2H), 5.67 (s, 2H), 4.72-4.67 (m, 1H), 2.65-2.54 (m, 2H), 2.12-2.06 (m, 5H).

ATPase Activity of Compound 17

The ATPase catalytic activity of BRM or BRG-1 in the presence of compound 17 was measured by the in vitro biochemical assay using ADP-Glo™ (Promega, V9102). The ADP-Glo™ kinase assay is performed in two steps once the reaction is complete. The first step is to deplete any unconsumed ATP in the reaction. The second step is to convert the reaction product ADP to ATP, which will be utilized by the luciferase to generate luminesce and be detected by a luminescence reader, such as Envision.

The assay reaction mixture (10 μL) contains 30 nM of BRM or BRG1, 20 nM salmon sperm DNA (from Invitrogen, UltraPure™ Salmon Sperm DNA Solution, cat #15632011), and 400 μM of ATP in the ATPase assay buffer, which comprises of 20 mM Tris, pH 8, 20 mM MgCl$_2$, 50 mM NaCl, 0.1% Tween-20, and 1 mM fresh DTT (Pierce™ DTT (Dithiothreitol), cat #20290). The reaction is initiated by the addition of the 2.5 μL ATPase solution to 2.5 μL ATP/DNA solution on low volume white Proxiplate-384 plus plate (PerkinElmer, cat #6008280) and incubates at room temperature for 1 hour. Then following addition of 5 μL of ADP-Glo™ Reagent provided in the kit, the reaction incubates at room temperature for 40 minutes. Then 10 μL of Kinase Detection Reagent provided in the kit is added to convert ADP to ATP, and the reaction incubates at room temperature for 60 minutes. Finally, luminescence measurement is collected with a plate-reading luminometer, such as Envision.

BRM and BRG1 were synthesized from high five insect cell lines with a purity of greater than 90%. Compound 17 was found to have an IP$_{50}$ of 10.4 nM against BRM and 19.3 nM against BRG1 in the assay.

Example 2. Effects of BRG1/BRM ATPase Inhibition on the Growth of Cancer Cell Lines Procedure: Uveal melanoma cell lines (92-1, MP41, MP38, MP46), prostate cancer cell lines (LNCAP), lung cancer cell lines (NCIH1299), and immortalized embryonic kidney lines (HEK293T) were plated into 96 well plates with growth media (see Table 1). BRG1/BRM ATPase inhibitor, compound 17, was dissolved in DMSO and added to the cells in a concentration gradient from 0 to 10 micromolar at the time of plating. Cells were incubated at 37° C. for 3 days. After 3 days of treatment, the media was removed from the cells, and 30 microliters of TrypLE (Gibco) was added to cells for 10 minutes. Cells were detached from the plates and resuspended with the addition of 170 microliters of growth media. Cells from two DMSO-treated control wells were counted, and the initial number of cells plated at the start of the experiment, were re-plated into fresh-compound containing plates for an additional four days at 37° C. At day 7, cells were harvested as described above.

On day 3 and day 7, relative cell growth was measured by the addition of Cell-titer glo (Promega), and luminescence was measured on an Envision plate reader (Perkin Elmer). The concentration of compound 17 at which each cell line's growth was inhibited by 50% ($GI_{50}$) was calculated using Graphpad Prism and is plotted in FIG. 1.

For multiple myeloma cell lines (OPM2, MM1S, LP1), ALL cell lines (TALL1, JURKAT, RS411), DLBCL cell lines (SUDHL6, SUDHL4, DB, WSUDLCL2, PFEIFFER), AML cell lines (OCIAML5), MDS cell lines (SKM1), ovarian cancer cell lines (OV7, TYKNU), esophageal cancer cell lines (KYSE150), rhabdoid tumor lines (RD, G402, G401, HS729, A204), liver cancer cell lines (HLF, HLE, PLCRPF5), and lung cancer cell lines (SW1573, NCIH2444), the above methods were performed with the following modifications: Cells were plated in 96 well plates, and the next day, BRG1/BRM ATPase inhibitor, compound 17, was dissolved in DMSO and added to the cells in a concentration gradient from 0 to 10 micromolar. At the time of cell splitting on days 3 and 7, cells were split into new 96 well plates, and fresh compound was added four hours after re-plating.

Table 1 lists the tested cell lines and growth media used.

TABLE 1

| Cell Line | Source | Growth Media |
|---|---|---|
| 92-1 | SIGMA | RPMI1640 + 20% FBS |
| A204 | ATCC | McCoy's 5A + 10% FBS |
| DB | ATCC | RPMI1640 + 10% FBS |
| G401 | ATCC | McCoy's 5A + 10% FBS |
| G402 | ATCC | McCoy's 5A + 10% FBS |
| HEK293T | ATCC | DMEM + 10% FBS |
| HLE | JCRB | DMEM + 10% FBS |
| HLF | JCRB | DMEM + 10% FBS |
| HS729 | ATCC | DMEM + 10% FBS |
| JURKAT | ATCC | RPMI1640 + 10% FBS |
| KYSE150 | DSMZ | RPMI1640/Ham's F12 + 10% FBS |
| LNCAP | ATCC | RPMI1640 + 10% FBS |
| LP1 | DSMZ | IMDM + 20% FBS |
| MM1S | ATCC | RPMI1640 + 10% FBS |
| MP38 | ATCC | RPMI1640 + 20% FBS |
| MP41 | ATCC | RPMI1640 + 20% FBS |
| MP46 | ATCC | RPMI1640 + 20% FBS |
| NCIH1299 | ATCC | RPMI1640 + 10% FBS |
| NCIH2444 | ATCC | RPMI1640 + 20% FBS |
| OCIAML5 | DSMZ | alpha-MEM + 20% FBS + 10 ng/ml GM-CSF |
| OPM2 | DSMZ | RPMI1640 + 10% FBS |
| OV7 | ECACC | DMEM/Ham's F12 (1:1) + 2 mM Glutamine + 10% FBS + 0.5 ug/ml hydrocortisone + 10 ug/ml insulin |
| PFEIFFER | ATCC | RPMI1640 + 10% FBS |
| PLCPRF5 | ATCC | EMEM + 10% FBS |
| RD | ATCC | DMEM + 10% FBS |
| RS411 | ATCC | RPMI1640 + 10% FBS |
| SKM1 | JCRB | RPMI1640 + 10% FBS |
| SUDHL4 | DSMZ | RPMI1640 + 10% FBS |
| SUDHL6 | ATCC | RPMI1640 + 20% FBS |
| SW1573 | ATCC | DMEM + 10% FBS |
| TALL1 | JCRB | RPMI1640 + 10% FBS |
| TYKNU | JCRB | EMEM + 20% FBS |
| WSUDLCL2 | DSMZ | RPMI1640 + 10% FBS |

Results: As shown in FIG. 1, the AML cell line was more sensitive to BRG1/BRM inhibition than the other tested cell lines. Inhibition of the AML cell lines was maintained through day 7.

Example 3. Synthesis of Compound 18

BRG1/BRM Inhibitor compound 18 has the structure:

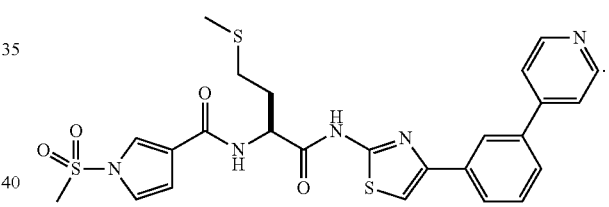

18

Compound 18 was synthesized as shown in Scheme 2 below.

Scheme 2. Synthesis of Compound 18

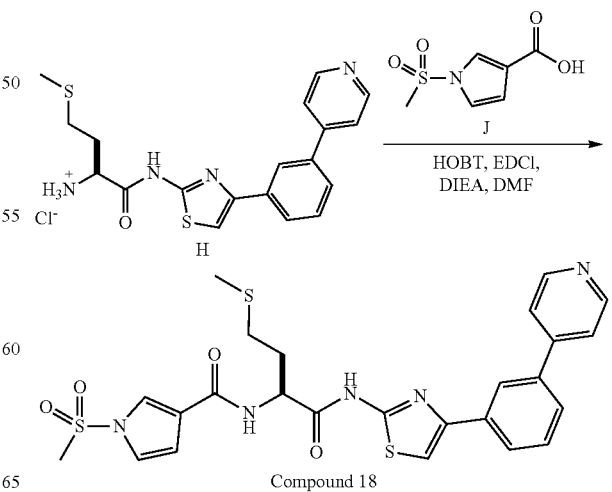

Compound 18

Step 1: Preparation of (S)-1-(methylsulfonyl)-N-(4-(methylthio)-1-oxo-1-((4-(3-(pyridin-4-yl)phenyl)thiazol-2-yl)amino)butan-2-yl)-1H-pyrrole-3-carboxamide (compound 18)

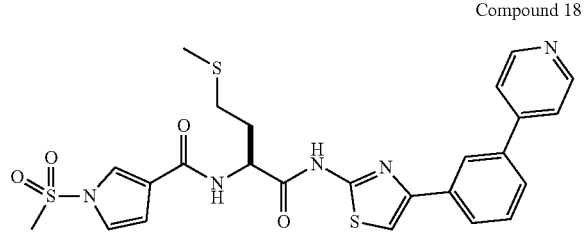 [SMILES: CSCC[C@H](NC(=O)c1ccn(S(C)(=O)=O)c1)C(=O)Nc1nc(-c2cccc(-c3ccncc3)c2)cs1]

Compound 18

To a mixture of (S)-4-(methylthio)-1-oxo-1-((4-(3-(pyridin-4-yl)phenyl)thiazol-2-yl)amino)butan-2-aminium chloride (2.00 g, 4.75 mmol) and 1-methylsulfonylpyrrole-3-carboxylic acid (0.899 g, 4.75 mmol) in DMF (20 mL) was added EDCl (1.37 g, 7.13 mmol), HOBt (0.963 g, 7.13 mmol), and N,N-diisopropylethylamine (3.31 mL, 19.00 mmol). After stirring for 3 h, the mixture was poured into water (100 mL) and the resulting precipitates were filtered. The solids were triturated in MeOH (20 mL) and the precipitate was collected by filtration. The solids were re-dissolved in DMSO (10 mL) and poured into MeOH (50 mL). The precipitates were filtered and lyophilized to give Compound 18 (2.05 g, 3.66 mmol, 77.01% yield) as white solids. LCMS (ESI) m/z [M+H]$^+$=555.9. $^1$H NMR (400 MHz, DMSO) δ 12.49 (s, 1H), 8.68-8.66 (m, 2H), 8.46 (d, J=7.2 Hz, 1H), 8.31-8.30 (m, 1H), 8.02-8.00 (m, 1H), 7.94-7.96 (m, 1H), 7.83 (s, 1H), 7.73-7.74 (m, 3H), 7.61-7.57 (m, 1H), 7.31-7.29 (m, 1H), 6.79-6.77 (m, 1H), 4.74-4.69 (m, 1H), 3.57 (s, 3H), 2.67-2.53 (m, 2H), 2.13-2.01 (m, 5H). SFC: AS-3-MeOH (DEA)-40-3 mL-35T·lcm, t=0.932 min, ee %=100%.

Example 4. Effects of BRG1/BRM ATPase Inhibition on the Growth of Cancer Cell Lines Procedure: All cell lines described above in Example 2 were also tested as described above with compound 18. In addition, the following cell lines were also tested as follows. Briefly, for Ewing's sarcoma cell lines (CADOES1, RDES, SKES1), retinoblastoma cell lines (WERIRB1), ALL cell lines (REH), AML cell lines (KASUMI1), prostate cancer cell lines (PC3, DU145, 22RV1), melanoma cell lines (SH4, SKMEL28, WM115, COLO829, SKMEL3, A375), breast cancer cell lines (MDAMB415, CAMA1, MCF7, BT474, HCC1419, DU4475, BT549), B-ALL cell lines (SUPB15), CML cell lines (K562, MEG01), Burkitt's lymphoma cell lines (RAMOS2G64C10, DAUDI), mantle cell lymphoma cell lines (JEKO1, REC1), bladder cancer cell lines (HT1197), and lung cancer cell lines (SBC5), the above methods were performed with the following modifications: Cells were plated in 96 well plates, and the next day, BRG1/BRM ATPase inhibitor, compound 18, was dissolved in DMSO and added to the cells in a concentration gradient from 0 to 10 micromolar. At the time of cell splitting on days 3 and 7, cells were split into new 96 well plates, and fresh compound was added four hours after re-plating.

Table 2 lists the tested cell lines and growth media used.

TABLE 2

Cell Lines and Growth Media

| Cell Line | Source | Growth Media |
|---|---|---|
| 22RV1 | ATCC | RPMI1640 + 10% FBS |
| A375 | ATCC | DMEM + 10% FBS |
| BT474 | ATCC | Hybricare medium + 1.5 g/L sodium bicarbonate + 10% FBS |
| BT549 | ATCC | RPMI1640 + 0.023 IU/ml insulin + 10% FBS |
| CADOES1 | DSMZ | RPMI1640 + 10% FBS |
| CAMA1 | ATCC | EMEM + 10% FBS |
| COLO829 | ATCC | RPMI1640 + 10% FBS |
| DAUDI | ATCC | RPMI1640 + 10% FBS |
| DU145 | ATCC | EMEM + 10% FBS |
| DU4475 | ATCC | RPMI1640 + 10% FBS |
| HCC1419 | ATCC | RPMI1640 + 10% FBS |
| HT1197 | ATCC | EMEM + 10% FBS |
| JEKO1 | ATCC | RPMI1640 + 20% FBS |
| K562 | ATCC | IMDM + 10% FBS |
| KASUMI1 | ATCC | RPMI1640 + 10% FBS |
| MCF7 | ATCC | EMEM + 0.01 mg/ml bovine insulin + 10% FBS |
| MDAMB415 | ATCC | Leibovitz's L-15 + 2 mM L-glutamine + 10 mcg/ml insulin + 10 mcg/ml glutathione + 15% FBS |
| MEG01 | ATCC | RPMI1640 + 10% FBS |
| PC3 | ATCC | F-12K + 10% FBS |
| RAMOS2G64C10 | ATCC | RPMI1640 + 10% FBS |
| RDES | ATCC | RPMI1640 + 15% FBS |
| REC1 | ATCC | RPMI1640 + 10% FBS |
| REH | ATCC | RPMI1640 + 10% FBS |
| SBC5 | JCRB | EMEM + 10% FBS |
| SH4 | ATCC | DMEM + 10% FBS |
| SKES1 | ATCC | McCoy's 5A + 15% FBS |
| SKMEL28 | ATCC | EMEM + 10% FBS |
| SKMEL3 | ATCC | McCoy's 5A + 15% FBS |
| SUPB15 | ATCC | IMDM + 4 mM L-glutamine + 1.5 g/L sodium bicarbonate + 0.05 mM 2-mercaptoethanol + 20% FBS |
| WERIRB1 | ATCC | RPMI1640 + 10% FBS |
| WM115 | ATCC | EMEM + 10% FBS |

Figure 2:
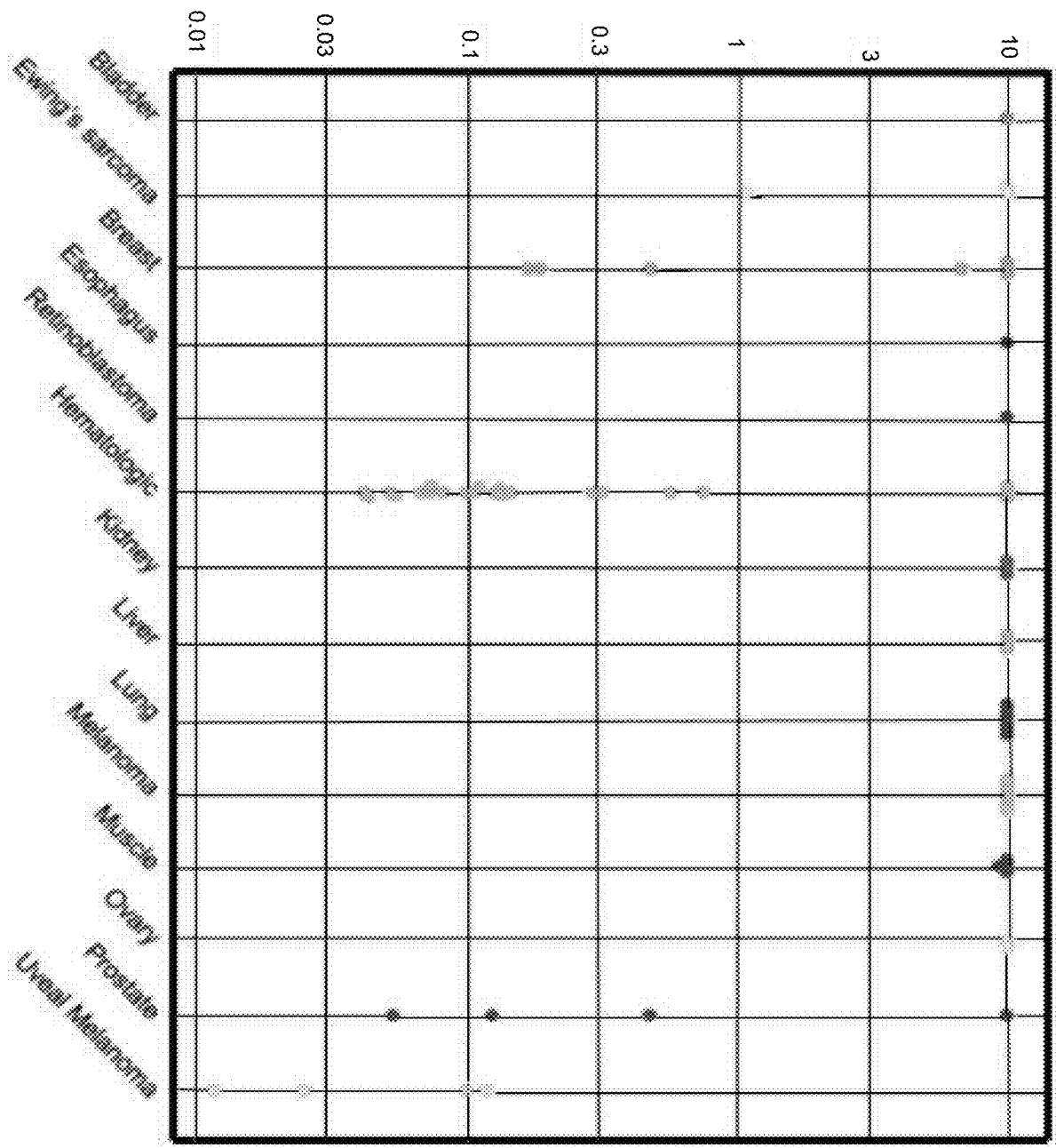
FIG. 2 is a graph illustrating inhibition of cell proliferation of several cancer cell lines by a BRG1/BRM inhibitor, compound 18.

Results: As shown in FIG. 2, the AML cell lines were more sensitive to BRG1/BRM inhibition than the other tested cell lines. Inhibition of the AML cell lines was maintained through day 7.

Example 5. Effects of BRG1/BRM ATPase Inhibition on the Growth of Cancer Cell Lines Procedure: A pooled cell viability assay was performed using PRISM (Profiling Relative Inhibition Simultaneously in Mixtures) as previously described ("High-throughput identification of genotype-specific cancer vulnerabilities in mixtures of barcoded tumor cell lines", Yu et al, Nature Biotechnology 34, 419-423, 2016), with the following modifications. Cell lines were obtained from the Cancer Cell Line Encyclopedia (CCLE) collection and adapted to RPMI-1640 medium without phenol red, supplemented with 10% heat-inactivated fetal bovine serum (FBS), in order to apply a unique infection and pooling protocol to such a big compendium of cell lines. A lentiviral spin-infection protocol was executed to introduce a 24 nucleotide-barcode in each cell line, with an estimated multiplicity of infection (MOI) of 1 for all cell lines, using blasticidin as selection marker. Over 750 PRISM cancer cell lines stably barcoded were then pooled together according to doubling time in pools of 25. For the screen execution, instead of plating a pool of 25 cell lines in each well as previously described (Yu et al.), all the adherent or all the suspension cell line pools were plated together using T25 flasks (100,000 cells/flask) or 6-well plates (50,000 cells/well), respectively. Cells were treated with either DMSO or compound in a 8-point 3-fold dose response in triplicate, starting from a top concentration of 10 µM. As control for assay robustness, cells were treated in parallel with two previously validated compounds, the pan-Raf inhibitor AZ-628, and the proteasome inhibitor bortezomib, using a top concentration of 2.5 µM and 0.039 µM, respectively.

Figure 3:
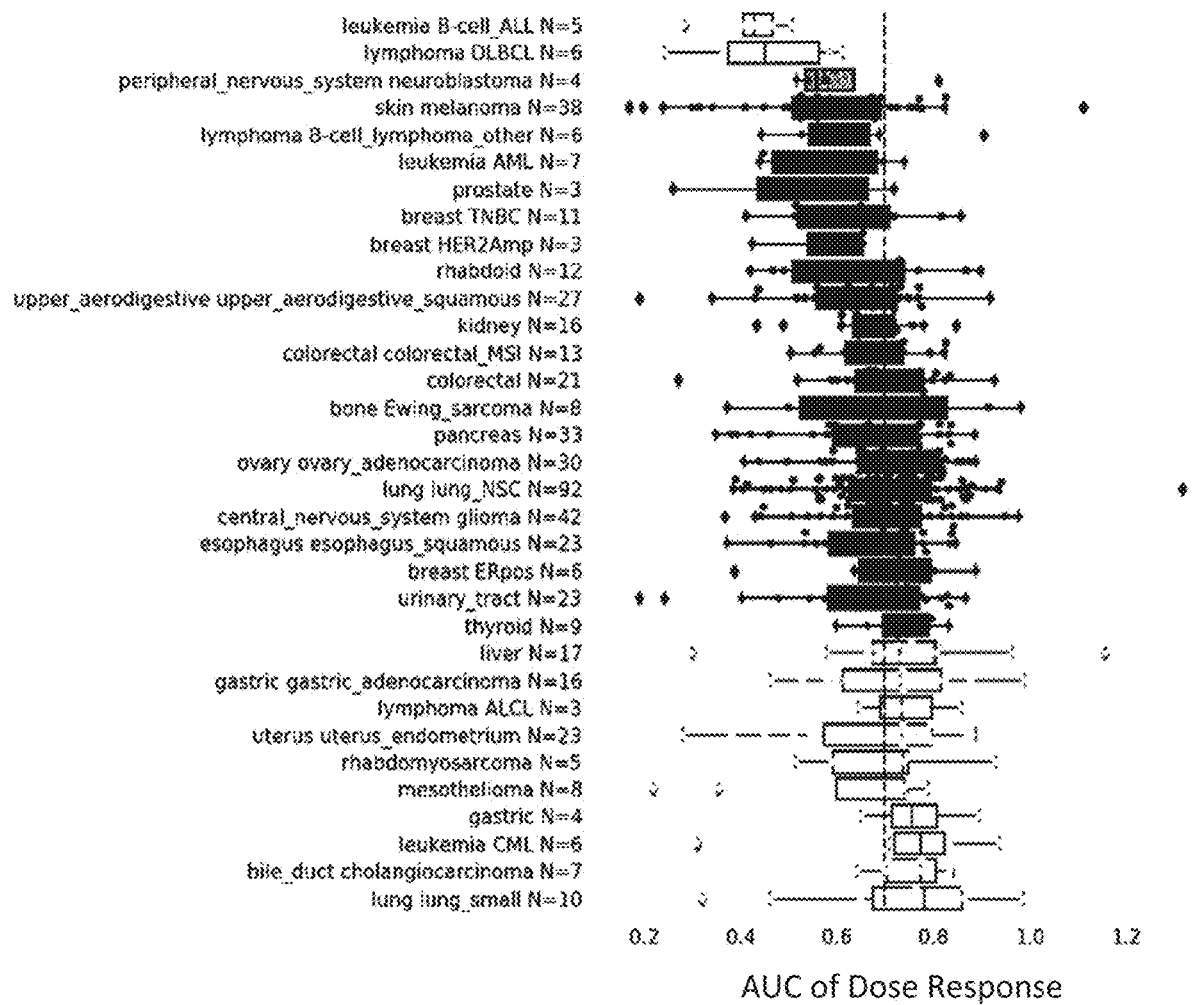
FIG. 3 is a graph illustrating the area under the curves (AUCs) calculated from dose-response curves for cancer cell lines treated with a BRG1/BRM inhibitor.

Following 3 days of treatment with compounds, cells were lysed, genomic DNA was extracted, barcodes were amplified by PCR and detected with Next-Generation Sequencing. Cell viability was determined by comparing the counts of cell-line specific barcodes in treated samples to those in the DMSO-control and Day 0 control. Dose-response curves were fit for each cell line and corresponding area under the curves (AUCs) were calculated and compared to the median AUC of all cell lines (FIG. 3). Cell lines with AUCs less than the median were considered most sensitive.

Example 6. Synthesis of Compound 19

BRG1/BRM inhibitor compound 19 has the structure:

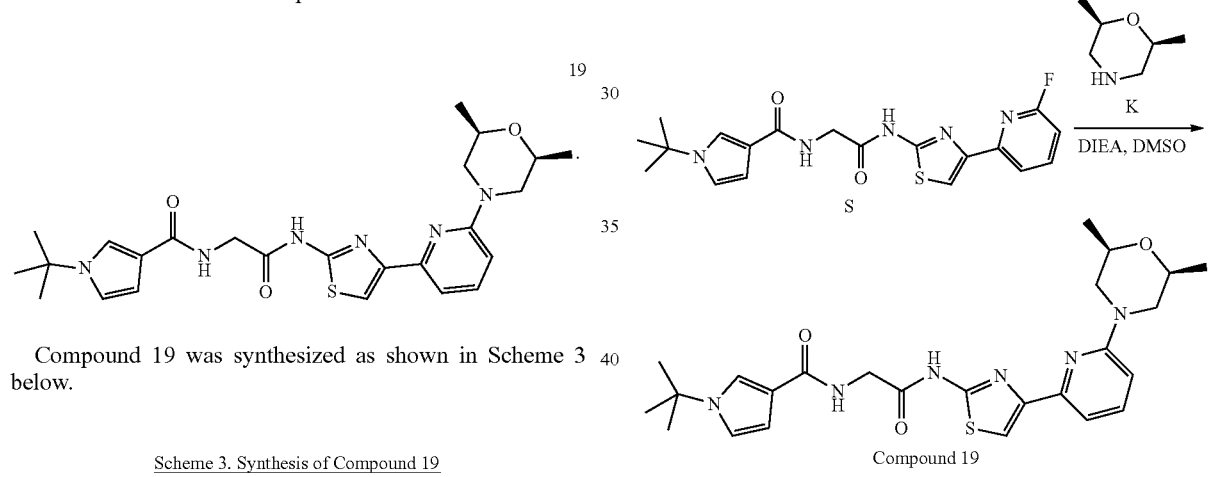

Compound 19 was synthesized as shown in Scheme 3 below.

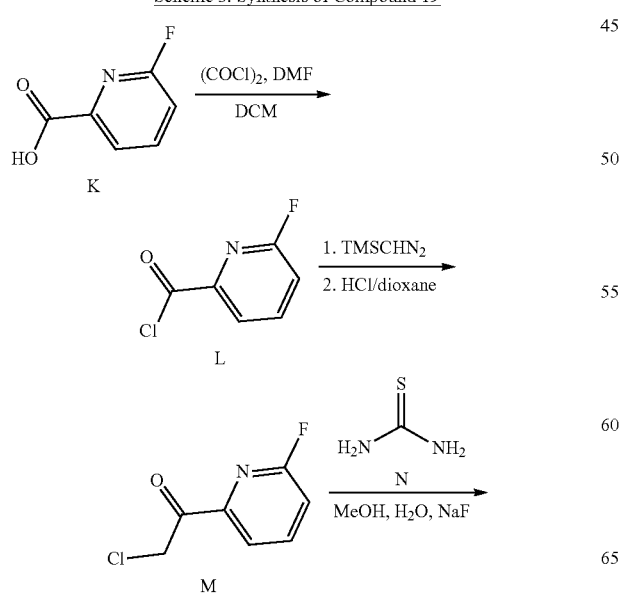

Step 1: Preparation of 6-fluoropyridine-2-carbonyl chloride (Intermediate L)

To a cooled (0° C.) solution of 6-fluoropyridine-2-carboxylic acid (50.00 g, 354.36 mmol) in dichloromethane (500 mL) and N,N-dimethylformamide (0.26 mL, 3.54 mmol) was added oxalyl chloride (155.10 mL, 1.77 mol). After complete addition of oxalyl chloride, the reaction mixture was warmed to room temperature and stirred for an additional 0.5 h. The mixture was subsequently concentrated in vacuo to give intermediate L (56.50 g) as white solids, which were used to next step without further purification.

Step 2: Preparation of 2-chloro-1-(6-fluoro-2-pyridyl)ethenone (Intermediate M)

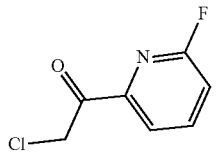

M

To a cooled (0° C.) mixture of intermediate L (56.00 g, 351.00 mmol) in 1,4-dioxane (800 mL) was added in a dropwise manner a solution of 2 M trimethylsilyl diazomethane in hexanes (351 mL). The resulting reaction mixture was stirred at 25° C. for 10 h. The reaction mixture was subsequently quenched with a solution of 4 M HCl in 1,4-dioxane (500 mL). After stirring for 2 h, the reaction solution was concentrated in vacuo to give an oil. The residue was diluted with saturated aqueous NaHCO$_3$ (500 mL) and extracted with EtOAc (3×200 mL). The combined organic layers were washed with brine (2×300 mL), dried over Na$_2$SO$_4$, filtered, and concentrated under reduced pressure to give intermediate M (35.50 g) as white solids, which was used to next step directly. LCMS (ESI) m/z: [M+H]$^+$=173.8.

Step 3: Preparation of 4-(6-fluoro-2-pyridyl)thiazol-2-amine (Intermediate O)

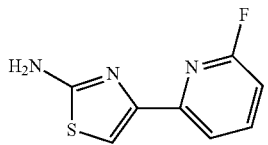

O

To a solution of intermediate M (35.50 g, 204.53 mmol) and thiourea (14.01 g, 184.07 mmol) in a mixture of MeOH (250 mL) and water (250 mL) at room temperature was added NaF (3.56 g, 84.82 mmol). After stirring for 30 min, the reaction mixture was partially concentrated in vacuo to remove MeOH. The resulting solution was acidified to pH ~3 with 2 M aqueous HCl and extracted with EtOAc (3×200 mL). The combined organic layers were discarded, and the aqueous phase was basified with saturated aqueous NaHCO$_3$ (500 mL). After stirring for 30 min, the aqueous phase was extracted with EtOAc (3×325 mL). The combined organic layers were washed with brine (3×225 mL), dried over Na$_2$SO$_4$, filtered, and concentrated under reduced pressure. The solids were triturated with petroleum ether (300 mL), stirred at 25° C. for 10 min, and filtered. The solids were dried under vacuum to give intermediate O (28.00 g, 143.43 mmol, 70.13% yield, 100% purity) as white solids. LCMS (ESI) m/z: [M+H]$^+$=195.8; $^1$H NMR (400 MHz, DMSO-d6) δ 8.00-7.96 (m, 1H), 7.72 (d, J=7.2 Hz, 1H), 7.24 (s, 1H), 7.16 (s, 2H), 7.02 (d, J=8.0 Hz, 1H).

Step 4: Preparation of tert-butyl N-[2-[[4-(6-fluoro-2-pyridyl)thiazol-2-yl]amino]-2-oxo-ethyl]carbamate (Intermediate P)

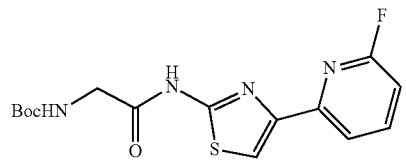

P

To a solution of N-Boc-glycine (5.92 g, 33.81 mmol), HATU (12.86 g, 33.81 mmol), and N,N-diisopropylethylamine (21.41 mL, 122.94 mmol) in dichloromethane (100 mL) was added intermediate O (6.00 g, 30.74 mmol). After stirring for 2 h, the reaction mixture was concentrated. The resulting oil was diluted with water (100 mL) and subsequently extracted with EtOAc (4×60 mL). The combined organic layers were washed with brine (2×100 mL), dried over Na$_2$SO$_4$, filtered, and concentrated under reduced pressure to give solids. The solids were triturated with a 1:1 mixture of petroleum ether and MeOH (40 mL). After stirring at 25° C. for 20 minutes, the suspension was filtered, and the filter cake was washed with MTBE (20 mL). The solids were dried in vacuo to give intermediate P (7.70 g, 21.63 mmol, 70.4% yield, 99.0% purity) as white solids. LCMS (ESI) m/z: [M+H]$^+$=353.1.

Step 5: Preparation of 2-((4-(6-fluoropyridin-2-yl)thiazol-2-yl)amino)-2-oxoethan-1-aminium chloride (Intermediate Q)

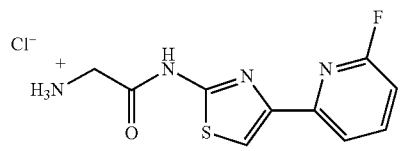

Q

A solution of intermediate P (5.40 g, 15.32 mmol) in 4 M HCl in 1,4-dioxane (35 mL) was stirred at 25° C. for 1.5 h. The reaction mixture was subsequently concentrated under vacuum to give intermediate Q (4.42 g) as white solids, which were used to next step directly without further purification. LCMS (ESI) m/z: [M+H]$^+$=252.9.

Step 6: Preparation of 1-tert-butyl-N-[2-[[4-(6-fluoro-2-pyridyl)thiazo]-2-yl]amino]-2-oxo-ethyl]pyrrole-3-carboxamide (Intermediate S)

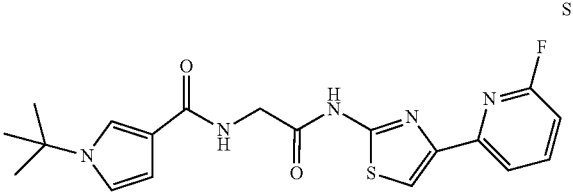 [SMILES: CC(C)(C)n1ccc(C(=O)NCC(=O)Nc2nc(-c3cccc(F)n3)cs2)c1]

S

To a solution of intermediate Q (3.00 g, 10.39 mmol), 1-tert-butylpyrrole-3-carboxylic acid (1.74 g, 10.39 mmol) and N,N-diisopropylethylamine (9.05 mL, 51.95 mmol) in dichloromethane (40 mL) was sequentially added HOBt (1.68 g, 12.47 mmol) and EDCl (2.39 g, 12.47 mmol). After stirring for 4 h, the mixture was concentrated in vacuo. The residue was diluted with water (250 mL) and extracted with EtOAc (3×200 mL). The combined organic layers were washed with brine (3×300 mL), dried over $Na_2SO_4$, filtered, and concentrated under reduced pressure. The resulting solids were triturated with a 1:1 mixture of MTBE/EtOAc (400 mL) and after stirring for 30 min, the suspension was filtered. The solids were washed with MTBE (3×85 mL) and dried under vacuum to give intermediate S (3.10 g, 7.64 mmol, 73.6% yield, 99.0% purity) as white solids. LCMS (ESI) m/z: $[M+H]^+$=402.3; $^1$H NMR (400 MHz, DMSO-d6) δ 12.40 (s, 1H), 8.18-8.15 (m, 1H), 8.09-8.08 (m, 1H), 7.87-7.83 (m, 2H), 7.52 (s, 1H), 7.11 (d, J=8.0 Hz, 1H), 6.97 (m, 1H), 6.47 (s, 1H), 4.10 (d, J=5.6 Hz, 2H), 1.49 (s, 9H).

Step 7: Preparation of 1-(tert-butyl)-N-(2-((4-(6-(cis-2,6-dimethylmorpholino)pyridin-2-yl)thiazol-2-yl)amino)-2-oxoethyl)-1H-pyrrole-3-carboxamide (compound 19)

Compound 19

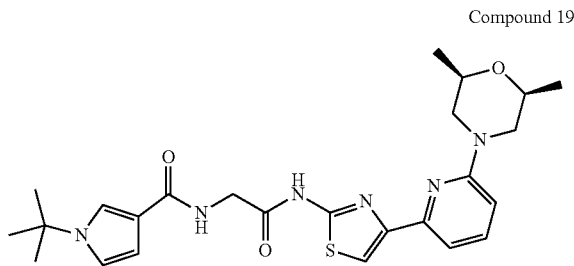 [SMILES: C[C@@H]1CN(c2cccc(-c3csc(NC(=O)CNC(=O)c4ccn(C(C)(C)C)c4)n3)n2)C[C@H](C)O1]

To a solution of intermediate S (0.100 g, 0.249 mmol) in DMSO (1 mL) was added N,N-diisopropylethylamine (0.130 mL, 0.747 mmol) and cis-2,6-dimethylmorpholine (0.057 g, 0.498 mmol). The resulting reaction mixture was stirred at 120° C. After 12 h, the solution was cooled to room temperature, diluted with MeOH (3 mL), and subsequently concentrated in vacuo. The resulting oil was purified by prep-HPLC (0.1% TFA; column: Luna C18 150*25 5 u; mobile phase: [water (0.075% TFA)–ACN]; B %: 30%-60%, 2 min). The appropriate fractions were collected and lyophilized to give Compound 19 (0.079 g, 0.129 mmol, 51.94% yield, 100% purity) as white solids. LCMS (ESI) m/z: $[M+H]^+$=497.5; $^1$H NMR (400 MHz, DMSO-d6) δ 12.27 (s, 1H), 8.17-8.14 (m, 1H), 7.75 (s, 1H), 7.63-7.59 (m, 1H), 7.51 (s, 1H), 7.25 (d, J=7.2 Hz, 1H), 6.96 (s, 1H), 6.79 (d, J=8.8 Hz, 1H), 6.47 (s, 1H), 4.24 (d, J=12.4 Hz, 2H), 4.08 (d, J=5.6 Hz, 2H), 3.64-3.61 (m, 2H), 2.44-2.38 (m, 2H), 1.49 (s, 9H), 1.18 (d, J=5.6 Hz, 6H).

Example 7. BRM/BRG1 Inhibition Causes Tumor Growth Delay and Stasis in MV4;11 and EOL-1 Human AML Tumors In Vivo Method: BALB/c Nude mice (Beijing Anikeeper Biotech, Beijing) were inoculated subcutaneously on the right flank with the single cell suspension of EOL-1 or MV4;11 human AML tumor cells (1×10$^7$) in 100 μL IDMD in 10% Fetal Bovine Serum (FBS). When tumor size reach ~100 mm3, the mice were randomized into either Vehicle group [20% HP-β-CD) or Treatment group: Compound 19 at 50 mg/kg daily for 21 days per oral route. All dose volumes were adjusted by body weights in terms of mg/kg.

Figure 4:
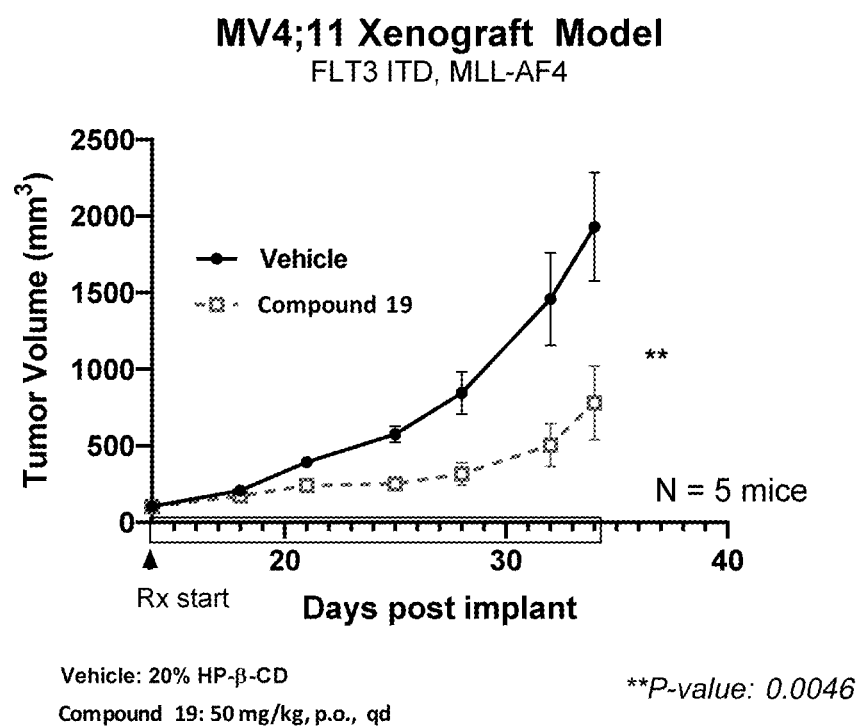
FIG. 4 is a graph illustrating in vivo inhibition of AML proliferation by a BRG1/BRM inhibitor.
Figure 5:
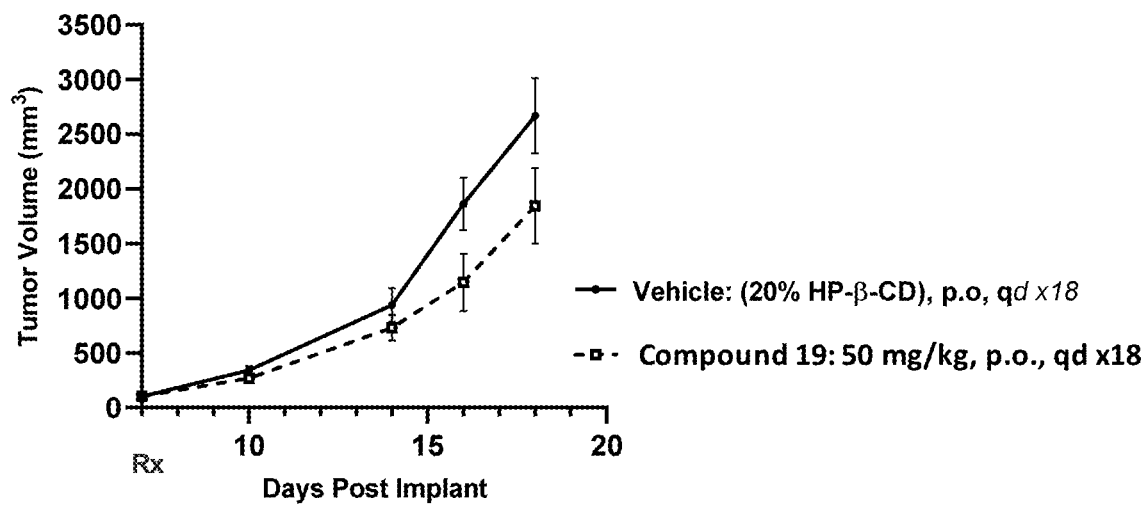
FIG. 5 is a graph illustrating in vivo inhibition of AML proliferation by a BRG1/BRM inhibitor.

Results: As shown in FIG. 4 treatment with 50 mg/kg of Compound 19 led to tumor stasis in MV4;11. As shown in FIG. 5, treatment with 50 mg/kg of Compound 19 delayed the growth of EOL-1 tumor. All treatments were well tolerated based on % body weight change observed.

Example 8. Synthesis of Compound 20

N—((S)-1-((4-(6-(cis-2,6-dimethylmorpholino)pyridin-2-yl)thiazol-2-yl)amino)-3-methoxy-1-oxopropan-2-yl)-1-(methylsulfonyl)-1H-pyrrole-3-carboxamide (Compound 20) was synthesized as shown in Scheme 4 below.

Scheme 4.

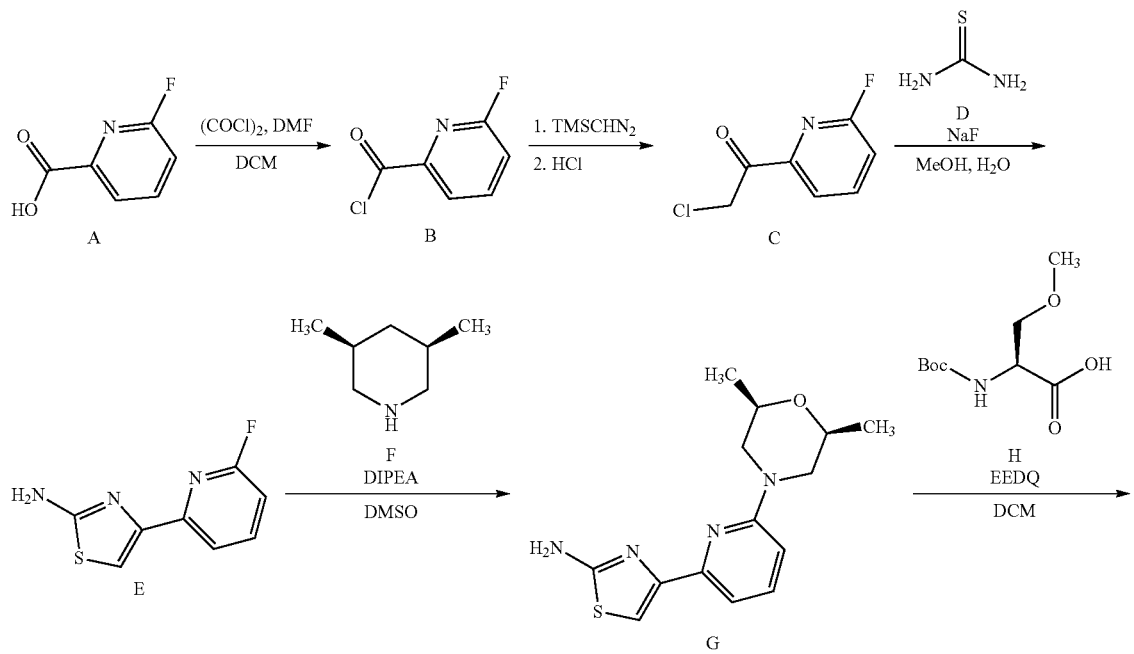

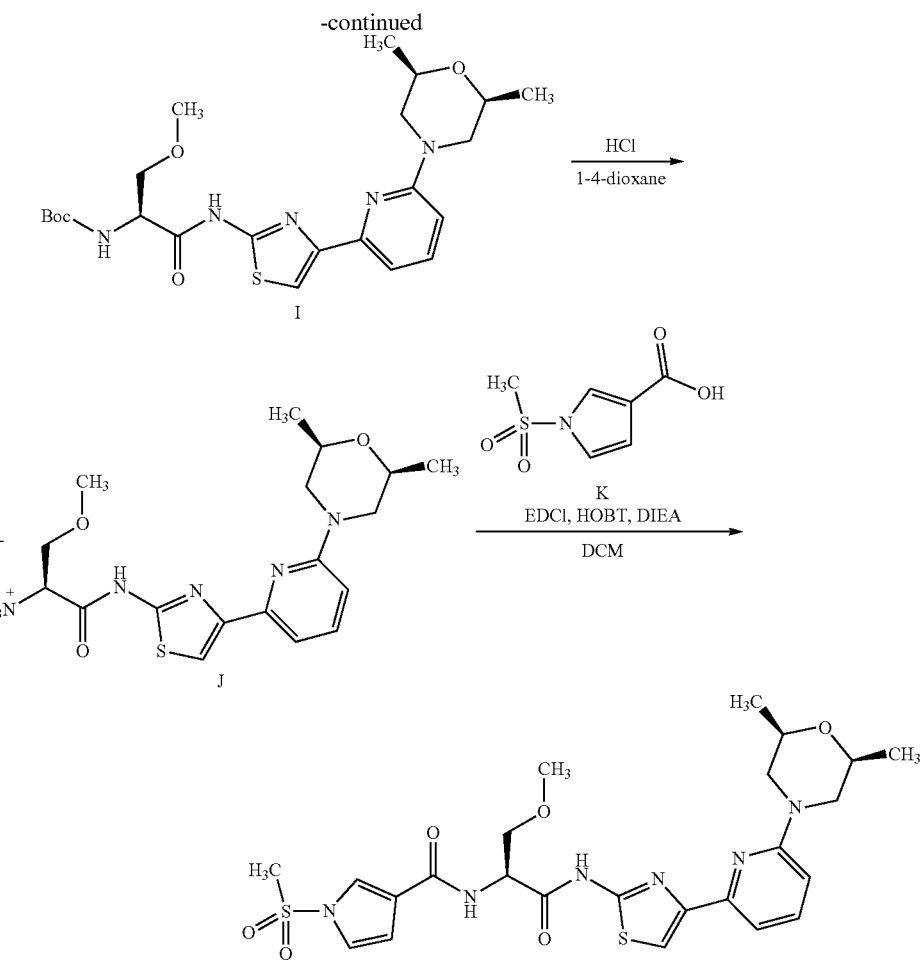

Step 1: Preparation of 6-fluoropyridine-2-carbonyl chloride (Intermediate B)

Step 2: Preparation of 2-chloro-1-(6-fluoro-2-pyridyl)ethenone (Intermediate C)

B

C

To a cooled (0° C.) solution of 6-fluoropyridine-2-carboxylic acid (50.0 g, 354 mmol) in dichloromethane (500 mL) and N,N-dimethylformamide (0.26 mL, 3.54 mmol) was added oxalyl chloride (155 mL, 1.77 mol). After complete addition of oxalyl chloride, the reaction mixture was warmed to room temperature. After 0.5 hours, the mixture was concentrated under vacuum to give Intermediate B (56.50 g) as a white solid, which was used in the next step without further purification.

To a cooled (0° C.) mixture of Intermediate B (56.0 g, 351 mmol) in 1,4-dioxane (800 mL) was added in a dropwise manner a solution of 2M trimethylsilyl diazomethane in hexanes (351 mL, 702 mmol). The resulting reaction mixture was stirred at 25° C. for 10 h. The reaction mixture was subsequently quenched with a solution of 4M HCl in 1,4-dioxane (500 mL, 2.0 mol). After stirring for 2 h, the reaction solution was concentrated under vacuum to give an oil. The residue was diluted with saturated aqueous $NaHCO_3$ and extracted three times with ethyl acetate. The combined organic layers were washed twice with brine, dried over $Na_2SO_4$, filtered, and concentrated under reduced pressure to give Intermediate C (35.5 g) as a white solid, which was used to next step directly.

LCMS (ESI) m/z: [M+H]$^+$=173.8.

Step 3: Preparation of 4-(6-fluoro-2-pyridyl)thiazol-2-amine (Intermediate E)

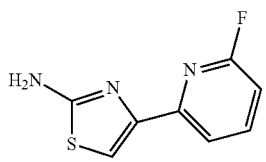

To a solution of Intermediate C (35.5 g, 205 mmol) and thiourea (14.0 g, 184 mmol) in a mixture of methanol (250 mL) and water (250 mL) at room temperature was added NaF (3.56 g, 84.8 mmol). After stirring for 0.5 h, the reaction mixture was partially concentrated under vacuum to remove MeOH, and the resulting solution was acidified to pH ~3 with aqueous 2M HCl. After 15 minutes, the solution was extracted three times with ethyl acetate. The organic layers were discarded and the aqueous phase was alkalized with saturated aqueous NaHCO$_3$ and stirred for 30 minutes, and extracted three times with ethyl acetate. The combined organic layers were washed three times with brine, dried over Na$_2$SO$_4$, filtered, and concentrated under reduced pressure. The residue was triturated with petroleum ether and stirred at 25° C. for 10 minutes and filtered. The resultant solids were dried under vacuum to give Intermediate E (28.0 g, 143 mmol, 70.1% yield, 100% purity) as a white solid.

LCMS (ESI) m/z: [M+H]$^+$=195.8.

$^1$H NMR (400 MHz, DMSO-d6) δ 8.00-7.96 (m, 1H), 7.72 (d, J=7.2 Hz, 1H), 7.24 (s, 1H), 7.16 (s, 2H), 7.02 (d, J=8.0 Hz, 1H).

Step 4: Preparation of 4-[6-[cis-2,6-dimethylmorpholin-4-yl]-2-pyridyl]thiazol-2-amine (Intermediate G)

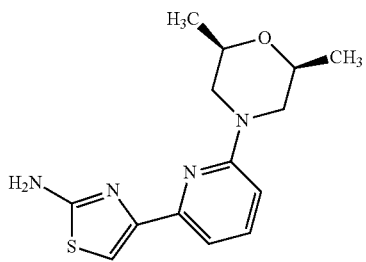

Ten separate mixtures of Intermediate E (2.00 g, 10.3 mmol), cis-2,6-dimethylmorpholine (3.54 g, 30.7 mmol), and DIPEA (5.35 mL, 30.7 mmol) in dimethyl sulfoxide (10 mL) were stirred in parallel at 120° C. under N2 atmosphere. After 36 h, the reaction mixtures were combined and added dropwise to water. The resulting suspension was filtered and the filter cake was washed three times with water and once with petroleum ether, then dried over under reduced pressure to give Intermediate G (25.5 g, 87.8 mmol, 95.2% yield) as a yellow solid.

LCMS (ESI) m/z: [M+H]$^+$=291.2.

$^1$H NMR (400 MHz, DMSO-d6) δ 7.56-7.54 (m, 1H), 7.17 (s, 1H), 7.13 (d, J=7.6 Hz, 1H), 7.01 (s, 2H), 6.72 (d, J=8.8 Hz, 1H), 4.26-4.15 (m, 2H), 3.67-3.55 (m, 2H), 2.38-2.34 (m, 2H), 1.17 (d, J=6.4 Hz, 6H).

Step 5: Preparation of tert-butyl N-[(1S)-2-[[4-[6-[cis-2,6-dimethylmorpholin-4-yl]-2-pyridyl]thiazol-2-yl]amino]-1-(methoxymethyl)-2-oxo-ethyl]carbamate (Intermediate I)

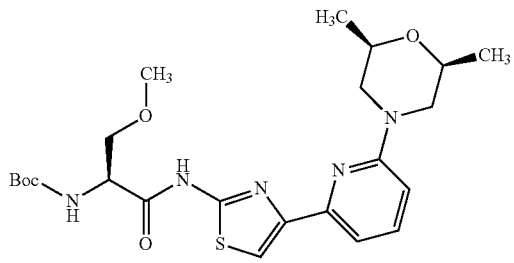

To a solution of Intermediate G (12.0 g, 41.3 mmol) and (2S)-2-(tertbutoxycarbonylamino)-3-methoxy-propanoic acid (10.9 g, 49.6 mmol) in dichloromethane (60 mL) was added EEDQ (12.3 g, 49.6 mmol). After stirring at room temperature for 16 h, the reaction mixture was concentrated under reduced pressure to give a residue. The residue was purified by silica gel column chromatography (petroleum ether:ethyl acetate=2:1 to 3:2) to give Intermediate I (20.0 g, 40.7 mmol, 98.5% yield) as a yellow gum.

LCMS (ESI) m/z: [M+H]$^+$=492.2.

$^1$H NMR (400 MHz, DMSO-d6) δ 12.37 (s, 1H), 7.78 (s, 1H), 7.64-7.60 (m, 1H), 7.25 (d, J=7.2 Hz, 1H), 7.16 (d, J=7.2 Hz, 1H), 6.79 (d, J=8.4 Hz, 1H), 4.50-4.48 (m, 1H), 4.25 (d, J=11.6 Hz, 2H), 3.70-3.51 (m, 4H), 3.26 (s, 3H), 2.44-2.40 (m, 2H), 1.39 (s, 9H), 1.18 (d, J=6.4 Hz, 6H).

Step 6: Preparation of (S)-4-(4-(6-(cis-2,6-dimethylmorpholino)pyridin-2-yl)thiazol-2-yl)-1-methoxy-3-oxobutan-2-aminium chloride (Intermediate J)

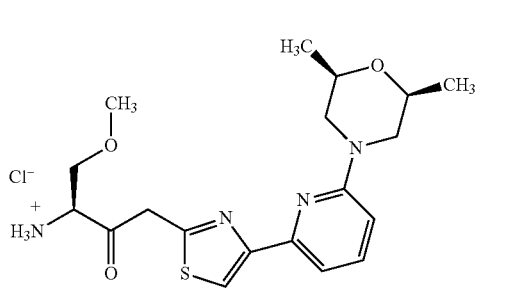

To a solution of 4M HCl in 1,4-dioxane (200 mL, 800 mmol) was added a solution of Intermediate I (20.0 g, 40.7 mmol) in dichloromethane (50 mL). After stirring at room temperature for 2 h, the mixture was diluted with methyl tert-butyl ether resulting in a suspension. The solid was collected by filtration, washed twice with methyl tert-butyl ether, and dried in vacuo to give Intermediate J (19.0 g) as a yellow solid, which was used in the next step without further purification.

LCMS (ESI) m/z: [M+H]$^+$=392.3.

$^1$H NMR (400 MHz, DMSO-d6) δ 13.44-12.30 (m, 1H), 8.65 (d, J=4.4 Hz, 3H), 7.87 (s, 1H), 7.66-7.64 (m, 1H), 7.25

(d, J=7.2 Hz, 1H), 6.83 (d, J=8.8 Hz, 1H), 4.39-4.30 (m, 1H), 4.25 (d, J=11.6 Hz, 2H), 3.94-3.86 (m, 1H), 3.85-3.77 (m, 1H), 3.69-3.57 (m, 2H), 3.31 (s, 3H), 2.43 (m, 2H), 1.18 (d, J=6.4 Hz, 6H).

Preparation of
1-(methylsulfonyl)-1H-pyrrole-3-carboxylic acid
(Intermediate K)

1-(methylsulfonyl)-1H-pyrrole-3-carboxylic acid was synthesized as shown in Scheme 5 below.

Scheme 5

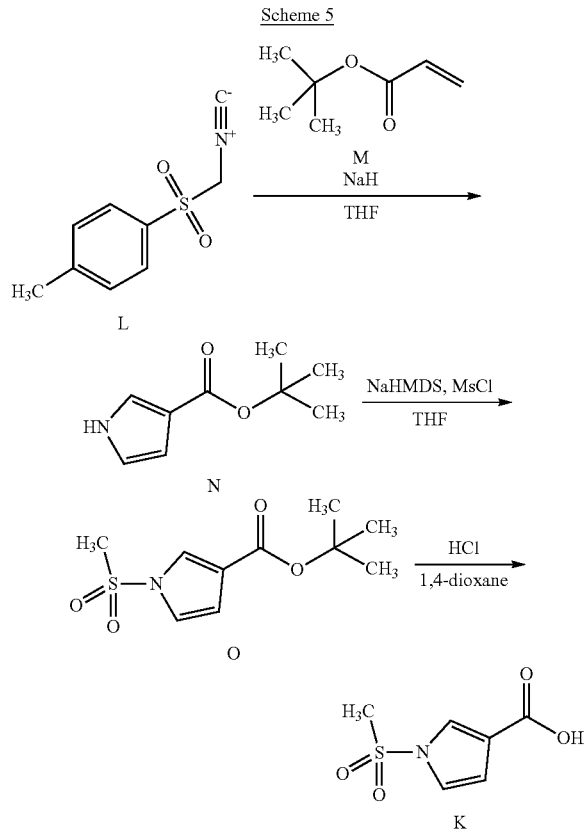

Step A: Preparation of tert-butyl
1H-pyrrole-3-carboxylate (Intermediate N)

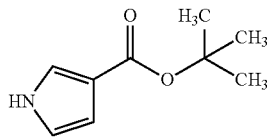

To a mixture of tert-butyl-prop-2-enoate (78.6 mL, 542 mmol) and 1-(isocyanomethylsulfonyl)-4-methylbenzene (106 g, 542 mmol) in THF (1300 mL) was added 60% NaH in mineral oil (25.97 g, 649 mmol) slowly at 30° C. over 1 hour and then heated to 70° C. After 2 h, the reaction mixture was poured into saturated aqueous NH₄Cl solution and extracted three times with ethyl acetate. The combined organic phase was washed twice with brine, dried over anhydrous Na₂SO₄, filtered, and concentrated under reduced pressure to afford a residue. The residue was purified by silica gel column chromatography (petroleum ether:ethyl acetate=20:1 to 3:1) to afford Intermediate N (41.5 g, 236 mmol, 43% yield) as a yellow solid.

LCMS (ESI) m/z [M+Na]⁺=180.4.
¹H NMR (400 MHz, CDCl₃) δ 8.36 (br s, 1H), 7.35-7.25 (m, 1H), 6.71-6.62 (m, 1H), 6.59-6.49 (m, 1H), 1.48 (s, 9H).

Step B: Preparation of tert-butyl
1-methylsulfonylpyrrole-3-carboxylate (Intermediate O)

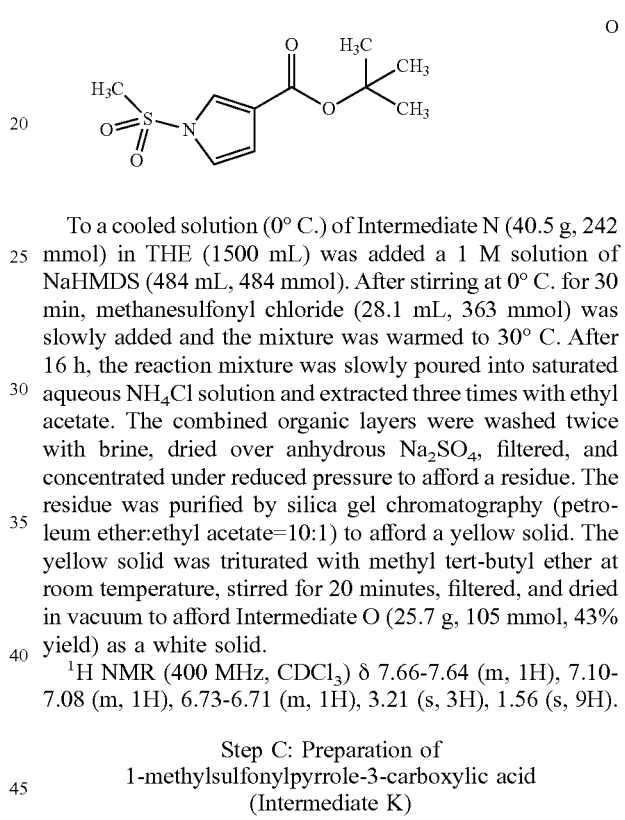

To a cooled solution (0° C.) of Intermediate N (40.5 g, 242 mmol) in THF (1500 mL) was added a 1 M solution of NaHMDS (484 mL, 484 mmol). After stirring at 0° C. for 30 min, methanesulfonyl chloride (28.1 mL, 363 mmol) was slowly added and the mixture was warmed to 30° C. After 16 h, the reaction mixture was slowly poured into saturated aqueous NH₄Cl solution and extracted three times with ethyl acetate. The combined organic layers were washed twice with brine, dried over anhydrous Na₂SO₄, filtered, and concentrated under reduced pressure to afford a residue. The residue was purified by silica gel chromatography (petroleum ether:ethyl acetate=10:1) to afford a yellow solid. The yellow solid was triturated with methyl tert-butyl ether at room temperature, stirred for 20 minutes, filtered, and dried in vacuum to afford Intermediate O (25.7 g, 105 mmol, 43% yield) as a white solid.

¹H NMR (400 MHz, CDCl₃) δ 7.66-7.64 (m, 1H), 7.10-7.08 (m, 1H), 6.73-6.71 (m, 1H), 3.21 (s, 3H), 1.56 (s, 9H).

Step C: Preparation of
1-methylsulfonylpyrrole-3-carboxylic acid
(Intermediate K)

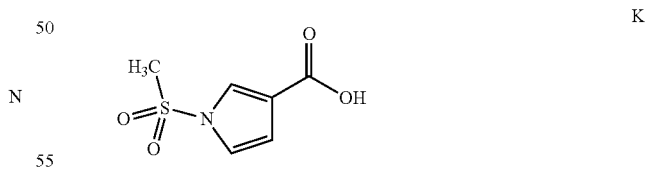

To a mixture of Intermediate O (25.7 g, 105 mmol) in 1,4-dioxane (100 mL) was added a 4M solution of HCl in 1,4-dioxane (400 mL, 1.6 mol) at 15° C. After stirring at at 15° C. for 14 h, the reaction mixture was concentrated under reduced pressure to afford a residue. The residue was triturated with methyl tert-butyl ether at 15° C. for 16 h. The mixture was filtered and dried in vacuum to afford Intermediate K (18.7 g, 98.8 mmol, 94% yield) as a white solid.

LCMS (ESI) m/z [M+H]⁺=189.8.
¹H NMR (400 MHz, methanol-d4) δ 7.78-7.77 (m, 1H), 7.25-7.23 (m, 1H), 6.72-6.70 (m, 1H), 3.37 (s, 3H).

Step 7: Preparation of N—((S)-1-((4-(6-(cis-2,6-dimethylmorpholino)pyridin-2-yl)thiazol-2-yl)amino)-3-methoxy-1-oxopropan-2-yl)-1-(methylsulfonyl)-1H-pyrrole-3-carboxamide

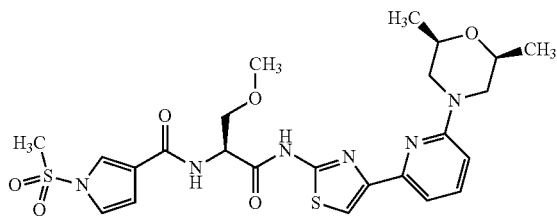 [SMILES: COC[C@H](NC(=O)c1ccn(S(C)(=O)=O)c1)C(=O)Nc1nc(-c2cccc(N3C[C@@H](C)O[C@@H](C)C3)n2)cs1]

To a solution of 1-methylsulfonylpyrrole-3-carboxylic acid (Intermediate K) (2.43 g, 12.9 mmol), EDCl (2.69 g, 14.0 mmol), HOBt (1.89 g, 14.0 mmol), and DIPEA (10.2 mL, 58.4 mmol) in dichloromethane (50 mL) was added Intermediate J (5.00 g, 11.7 mmol). After stirring at room temperature for 4 h, the reaction mixture was concentrated under reduced pressure. The residue was diluted with water and extracted three times with ethyl acetate. The combined organic layers were washed three times with saturated aqueous $NH_4Cl$, once with brine, dried over $Na_2SO_4$, filtered, and concentrated under reduced pressure to give a residue. The residue was purified by silica gel column chromatography (petroleum ether:ethyl acetate=1:1 to 1:2). The residue was triturated with methyl tert-butyl ether. After 0.5 h, the suspension was filtered, the filter cake was washed with methyl tert-butyl ether, and dried in vacuo. The solid was dissolved in dimethyl sulfoxide (12 mL) and added dropwise to water (800 mL). The suspension was filtered to give wet filter cake. The filter cake was suspended in water and stirred at room temperature. After 1 hour, the solid was collected by filtration, washed three times with water and dried in vacuo to give N—((S)-1-((4-(6-(cis-2,6-dimethylmorpholino)pyridin-2-yl)thiazol-2-yl)amino)-3-methoxy-1-oxopropan-2-yl)-1-(methylsulfonyl)-1H-pyrrole-3-carboxamide (3.9 g, 6.93 mmol, 59.3% yield) as a white solid.

LCMS (ESI) m/z: $[M+H]^+$=563.1.

$^1$H NMR (400 MHz, DMSO-d6) δ 12.49 (br s, 1H), 8.51 (d, J=7.2 Hz, 1H), 7.98-7.97 (m, 1H), 7.78 (s, 1H), 7.67-7.57 (m, 1H), 7.29-7.27 (m, 1H), 7.26 (d, J=7.2 Hz, 1H), 6.88-6.74 (m, 2H), 4.94-4.91 (m, 1H), 4.25 (d, J=11.6 Hz, 2H), 3.77-3.67 (m, 2H), 3.63-3.62 (m, 2H), 3.57 (s, 3H), 3.31 (s, 3H), 2.44-2.38 (m, 2H), 1.18 (d, J=6.0 Hz, 6H).

Example 9. BRM/BRG1 Inhibition Causes Tumor Growth Delay in an OCI-AML2 Tumor that Carries a DNMT3A Mutation Method: SCID mice (Charles River, Wilmington) were inoculated subcutaneously on the right flank with the single cell suspension of OCI-AML2 human AML tumor cells ($1\times10^7$) in 100 µL in RPMI-1640 media. When tumor size reach ~100 mm$^3$, the mice were randomized into either Vehicle group (20% HP-β-CD) or Treatment group (Compound 20 at 1.5 mg/kg daily for 21 days per oral route). All dose volumes were adjusted by body weights in terms of mg/kg.

Figure 6:
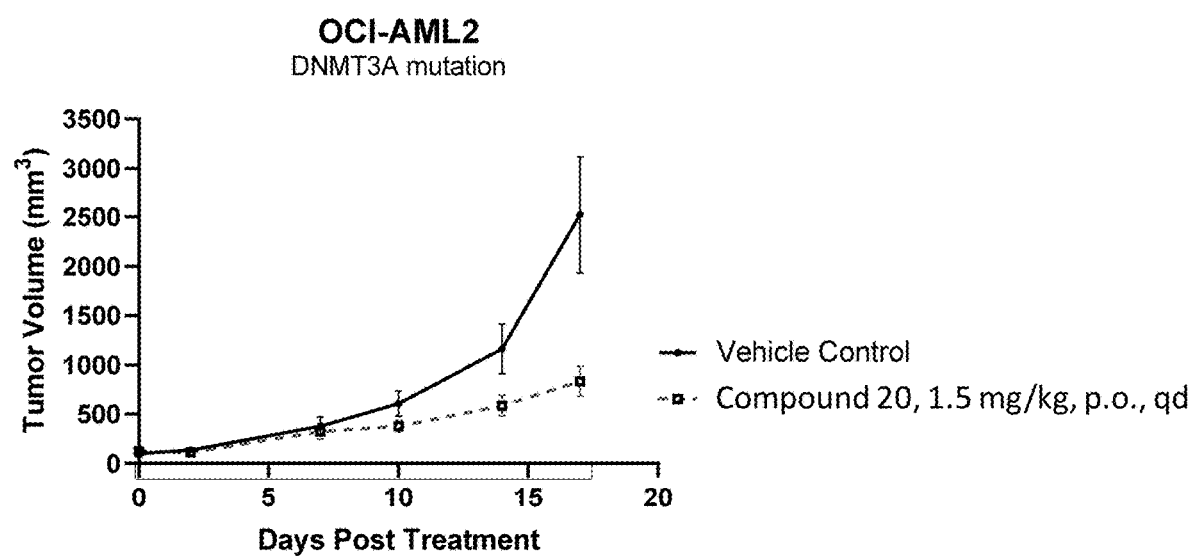
FIG. 6 is a graph illustrating in vivo inhibition of AML proliferation by a BRG1/BRM inhibitor.

Results: As shown in FIG. 6, treatment with Compound 20 at 1.5 mg/kg inhibited the growth of OCI-AML2 tumor. All treatments were well tolerated based on % body weight change observed.

OTHER EMBODIMENTS

All publications, patents, and patent applications mentioned in this specification are incorporated herein by reference in their entirety to the same extent as if each individual publication, patent, or patent application was specifically and individually indicated to be incorporated by reference in its entirety. Where a term in the present application is found to be defined differently in a document incorporated herein by reference, the definition provided herein is to serve as the definition for the term.

While the invention has been described in connection with specific embodiments thereof, it will be understood that invention is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are in the claims.

The invention claimed is:

1. A method of treating acute myeloid leukemia that harbors a DNMT3A, RUNX1, or ASXL1 mutation in a subject in need thereof, the method comprising administering to the subject an effective amount of an agent, wherein the agent is a small molecule compound having the structure:

Formula IVa

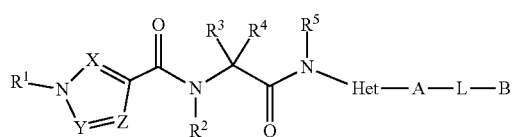

wherein each of X, Y, and Z is, independently, N or CH;
wherein R1 is absent, H, $C_1$-$C_6$ acyl, $C_1$-$C_6$ alkyl, $C_3$-$C_8$ cycloalkyl, $C_1$-$C_6$ heteroalkyl, $C_2$-$C_9$ heterocyclyl, or —$SO_2R^6$;
each of $R^2$ and $R^5$ is, independently, H or $C_1$-$C_6$ alkyl;
$R^3$ is H or $C_1$-$C_6$ alkyl;
and $R^4$ is H, $C_1$-$C_6$ alkyl, or $C_1$-$C_6$ heteroalkyl; or $R^3$ and $R^4$, together with the carbon atom to which each is attached, form an $C_3$-$C_6$ cycloalkyl;
$R^6$ is $C_1$-$C_6$ alkyl or —$NR7R^8$;
$R^7$ and $R^8$ are, independently, $C_1$-$C_6$;
Het is 5-membered heteroarylene, 6-membered heteroarylene, or

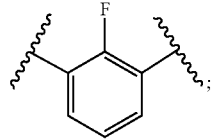 [SMILES: *c1cccc(*)c1F]

A is $C_6$-$C_{10}$ arylene, $C_2$-$C_9$ heterocyclylene, or $C_2$-$C_9$ heteroarylene;
L is absent, —O—, $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, $C_2$-$C_9$ heterocyclylene, $C_2$-$C_9$ heterocyclyl $C_1$-$C_6$ alkylene, $C_2$-$C_9$ heteroarylene, or $C_2$-$C_9$ heteroaryl $C_1$-$C_6$ alkylene, wherein the C2-C9 heterocyclylene is optionally substituted with $C_1$-$C_6$ alkyl;
and B is H, halogen, cyano, C6-C10 aryl, $C_3$-$C_{10}$ cycloalkyl, $C_2$-$C_9$ heterocyclyl, or $C_2$-$C_9$ heteroaryl, wherein the $C_2$-$C_9$ heterocyclyl is optionally substituted with $C_1$-$C_6$ alkyl;
or a pharmaceutically acceptable salt thereof.

2. The method of claim 1, wherein the acute myeloid leukemia is metastatic.

3. The method of claim 1, wherein the method further comprises administering induction chemotherapy.

4. The method of claim 3, wherein the induction chemotherapy comprises cytarabine, an anthracycline, or combinations thereof.

5. The method of claim 1, wherein the method further comprises administering consolidation therapy.

6. The method of claim 5, wherein the consolidation therapy comprises an allogenic stem cell transplantation or immunotherapy.

7. The method of claim 1, wherein the method further comprises administering a hemopoietic stem cell transplant, gemtuzumab ozogamicin, or a combination thereof.

8. The method of claim 1, wherein the subject or cancer has or has been identified as having a BRG1 or BRM loss of function mutation.

9. The method of claim 1, wherein the acute myeloid leukemia has failed to respond to or progressed after administration of one or more chemotherapeutic or cytotoxic agents.

10. The method of claim 1, wherein the acute myeloid leukemia is resistant to, or predicted to be resistant to one or more chemotherapeutic agents.

11. The method of claim 9, wherein the one or more chemotherapeutic or cytotoxic agents is cytarabine, an anthracycline or gemtuzumab ozogamicin.

12. The method of claim 1, wherein the effective amount of the agent reduces the level or activity of BRG1 or BRM by at least 5% as compared to a reference.

13. The method of claim 1, wherein the small molecule compound has the structure:

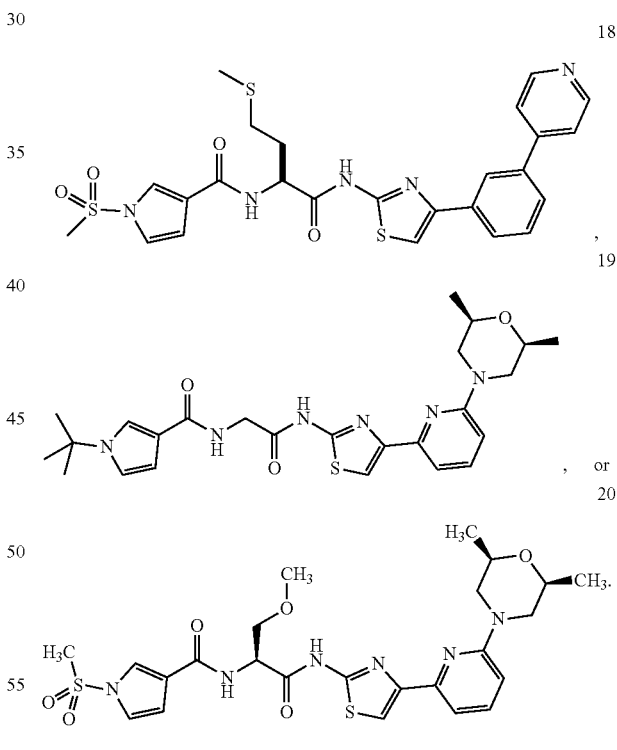

* * * * *

SEQUENCE LISTING

```
<160> NUMBER OF SEQ ID NOS: 4

<210> SEQ ID NO 1
<211> LENGTH: 5589
<212> TYPE: RNA
<213> ORGANISM: Homo sapiens

<400> SEQUENCE: 1
ggcgggggag gcgccgggaa gtcgacggcg ccggcggctc ctgcaggagg ccactgtctg      60
cagctcccgt gaagatgtcc actccagacc cacccctggg cggaactcct cggccaggtc     120
cttccccggg ccctggccct tccctggag ccatgctggg ccctagcccg ggtccctcgc      180
cgggctccgc ccacagcatg atggggccca gcccagggcc gccctcagca ggacacccca     240
tccccaccca ggggcctgga gggtaccctc aggacaacat gcaccagatg cacaagccca     300
tggagtccat gcatgagaag ggcatgtcgg acgaccgcg ctacaaccag atgaaaggaa      360
tggggatgcg gtcaggggc catgctggga tggggccccc gcccagcccc atggaccagc     420
```

```
actcccaagg ttacccctcg ccctgggtg gctctgagca tgcctctagt ccagttccag      480
ccagtggccc gtcttcgggg ccccagatgt cttccgggcc aggaggtgcc ccgctggatg      540
gtgctgaccc ccaggccttg gggcagcaga accggggccc aaccccattt aaccagaacc      600
agctgcacca gctcagagct cagatcatgg cctacaagat gctggccagg gggcagcccc      660
tccccgacca cctgcagatg gcggtgcagg gcaagcggcc gatgcccggg atgcagcagc      720
agatgccaac gctacctcca ccctcggtgt ccgcaacagg accggccct ggccctggcc      780 ctggccccgg cccgggtccc ggcccggcac ctccaaatta cagcaggcct catggtatgg      840
gagggcccaa catgcctccc caggaccct cgggcgtgcc cccgggatg ccaggccagc      900 ctcctggagg gcctcccaag ccctggcctg aaggacccat ggcgaatgct gctgccccca      960
cgagcacccc tcagaagctg attccccgc agccaacggg ccgccttcc cccgcgcccc     1020 ctgccgtccc accgccgcc tcgcccgtga tgccaccgca gacccagtcc cccgggcagc     1080
cggcccagcc cgcgcccatg gtgccactgc accagaagca gagccgcatc accccatcc     1140 agaagccgcg gggcctcgac cctgtggaga tcctgcagga gcgcgagtac aggctgcagg     1200
ctcgcatcgc acaccgaatt caggaacttg aaaaccttcc cgggtccctg gccgggggatt     1260 tgcgaaccaa agcgaccatt gagctcaagg ccctcaggct gctgaacttc cagaggcagc     1320
tgcgccagga ggtggtggtg tgcatgcgga gggacacagc gctggagaca gccctcaatg     1380
ctaaggccta caagcgcagc aagcgccagt ccctgcgcga ggcccgcatc actgagaagc     1440
tggagaagca gcgaagatc gagcaggagc gcaagcgccg gcagaagcac caggaatacc     1500
tcaatagcat tctccagcat gccaaggatt tcaaggaata tcacagatcc gtcacaggca     1560
aaatccagaa gctgaccaag gcagtggcca cgtaccatgc caacacggag cgggagcaga     1620
agaaagagaa cgagcggatc gagaaggagc gcatgcggag gctcatggct gaagatgagg     1680
aggggtaccg caagctcatc gaccagaaga aggacaagcg cctggcctac ctcttgcagc     1740
agacagacga gtacgtggct aacctcacgg agctggtgcg gcagcacaag gctgcccagg     1800
tcgccaagga gaaaaagaag aaaaagaaaa agaagaaggc agaaaatgca gaaggacaga     1860
cgcctgccat tgggccggat ggcgagcctc tggacgagac cagccagatg agcgacctcc     1920
cggtgaaggt gatccacgtg gagagtggga agatcctcac aggcacagat gcccccaaag     1980
ccgggcagct ggaggcctgg ctcgagatga acccggggta tgaagtagct ccgaggtctg     2040
atagtgaaga aagtggctca gaagaagagg aagaggagga gggaggaagag cagccgcagg     2100 cagcacagcc tccacccctg cccgtggagg agaagaagaa gattccagat ccagacagcg     2160
atgacgtctc tgaggtggac gcgcggcaca tcattgagaa tgccaagcaa gatgtcgatg     2220
atgaatatgg cgtgtcccag gcccttgcac gtggcctgca gtcctactat gccgtggccc     2280
atgctgtcac tgagagagtg gacaagcagt cagcgcttat ggtcaatggt gtcctcaaac     2340
agtaccagat caaaggttg gagtggctgg tgtccctgta caacaacaac ctgaacggca     2400
tcctggccga cgagatgggc ctggggaaga ccatccagac catcgcgctc atcacgtacc     2460
tcatggagca caaacgcatc aatgggccct cctcatcat cgtgcctctc tcaacgctgt     2520
ccaactgggc gtacgagttt gacaagtggg cccctccgt ggtgaaggtg tcttacaagg     2580
gatccccagc agcaagacgg gcctttgtcc cccagctccg gagtgggaag ttcaacgtct     2640
tgctgacgac gtacgagtac atcatcaaag acaagcacat cctcgccaag atccgttgga     2700
agtacatgat tgtggacgaa ggtcaccgca tgaagaacca ccactgcaag ctgacgcagg     2760
```

```
tgctcaacac gcactatgtg gcaccccgcc gcctgctgct gacgggcaca ccgctgcaga   2820
acaagcttcc cgagctctgg gcgctgctca acttcctgct gcccaccatc ttcaagagct   2880
gcagcacctt cgagcagtgg tttaacgcac cctttgccat gaccggggaa aaggtggacc   2940
tgaatgagga ggaaaccatt ctcatcatcc ggcgtctcca caaagtgctg cggcccttct   3000
tgctccgacg actcaagaag gaagtcgagg cccagttgcc cgaaaaggtg gagtacgtca   3060
tcaagtgcga catgtctgcg ctgcagcgag tgctctaccg ccacatgcag gccaagggcg   3120
tgctgctgac tgatggctcc gagaaggaca agaagggcaa aggcggcacc aagaccctga   3180
tgaacaccat catgcagctg cggaagatct gcaaccaccc ctacatgttc cagcacatcg   3240
aggagtcctt ttccgagcac ttggggttca ctggcggcat tgtccaaggg ctggacctgt   3300
accgagcctc gggtaaattt gagcttcttg atagaattct tcccaaactc cgagcaacca   3360
accacaaagt gctgctgttc tgccaaatga cctccctcat gaccatcatg gaagattact   3420
ttgcgtatcg cggctttaaa tacctcaggc ttgatggaac cacgaaggcg gaggaccggg   3480
gcatgctgct gaaaaccttc aacgagcccg gctctgagta cttcatcttc ctgctcagca   3540
cccgggctgg ggggctcggc ctgaacctcc agtcggcaga cactgtgatc atttttgaca   3600
gcgactggaa tcctcaccag gacctgcaag cgcaggaccg agcccaccgc atcgggcagc   3660
agaacgaggt gcgtgtgctc cgcctctgca ccgtcaacag cgtggaggag aagatcctag   3720
ctgcagccaa gtacaagctc aacgtggacc agaaggtgat ccaggccggc atgttcgacc   3780
agaagtcctc cagccatgag cggcgcgcct tcctgcaggc catcctggag cacgaggagc   3840
aggatgagag cagacactgc agcacgggca gcggcagtgc cagcttcgcc cacactgccc   3900
ctccgccagc gggcgtcaac cccgacttgg aggagccacc tctaaaggag gaagacgagg   3960
tgcccgacga cgagaccgtc aaccagatga tcgcccggca cgaggaggag tttgatctgt   4020
tcatgcgcat ggacctggac cgcaggcgcg aggaggcccg caaccccaag cggaagccgc   4080
gcctcatgga ggaggacgag ctcccctcgt ggatcatcaa ggacgacgcg gaggtggagc   4140
ggctgacctg tgaggaggag gaggagaaga tgttcggccg tggctcccgc accgcaagg   4200
aggtggacta cagcgactca ctgacggaga gcagtggct caagaaaatt acaggaaaag   4260
atatccatga cacagccagc agtgtggcac gtgggctaca attccagcgt ggccttcagt   4320
tctgcacacg tgcgtcaaag gccatcgagg agggcacgct ggaggagatc gaagaggagg   4380
tccggcagaa gaaatcatca cggaagcgca agcgagacag cgacgccggc tcctccaccc   4440
cgaccaccag caccccgcagc cgcgacaagg acgacgagag caagaagcag aagaagcgcg   4500
gcggccgcc tgccgagaaa ctctccccta acccacccaa cctcaccaag aagatgaaga   4560
agattgtgga tgccgtgatc aagtacaagg acagcagcag tggacgtcag ctcagcgagg   4620
tcttcatcca gctgccctcg cgaaaggagc tgcccgagta ctacgagctc atccgcaagc   4680
ccgtggactt caagaagata aaggagcgca ttcgcaacca caagtaccgc agcctcaacg   4740
acctagagaa ggacgtcatg ctcctgtgcc agaacgcaca gaccttcaac ctggagggct   4800
ccctgatcta tgaagactcc atcgtcttgc agtcggtctt caccagcgtg cggcagaaaa   4860
tcgagaagga ggatgacagt gaaggcgagg agagtgagga ggaggaagag ggcgaggagg   4920
aaggctccga atccgaatct cggtccgtca agtgaagat caagcttggc cggaaggaga   4980
aggcacagga ccggctgaag ggcggccggc ggcggccgag ccagggtcc cgagccaagc   5040
cggtcgtgag tgacgatgac agtgaggagg aacaagagga ggaccgctca ggaagtggca   5100
gcgaagaaga ctgagccccg acattccagt ctcgaccccg agcccctcgt tccagagctg   5160
```

```
agatggcata ggccttagca gtaacgggta gcagcagatg tagtttcaga cttggagtaa    5220
aactgtataa acaaaagaat cttccatatt tatacagcag agaagctgta ggactgtttg    5280
tgactggccc tgtcctggca tcagtagcat ctgtaacagc attaactgtc ttaaagagag    5340
agagagagaa ttccgaattg gggaacacac gatacctgtt tttctttttcc gttgctggca   5400 gtactgttgc gccgcagttt ggagtcactg tagttaagtg tggatgcatg tgcgtcaccg    5460
tccactcctc ctactgtatt ttattggaca ggtcagactc gccggggggcc cggcgagggt   5520 atgtcagtgt cactggatgt caaacagtaa taaattaaac caacaacaaa acgcacagcc    5580
aaaaaaaaa                                                             5589
```

<210> SEQ ID NO 2
<211> LENGTH: 1647
<212> TYPE: PRT
<213> ORGANISM: Homo sapiens

<400> SEQUENCE: 2

```
Met Ser Thr Pro Asp Pro Pro Leu Gly Gly Thr Pro Arg Pro Gly Pro
1               5                   10                  15

Ser Pro Gly Pro Gly Pro Ser Pro Gly Ala Met Leu Gly Pro Ser Pro
            20                  25                  30

Gly Pro Ser Pro Gly Ser Ala His Ser Met Met Gly Pro Ser Pro Gly
        35                  40                  45

Pro Pro Ser Ala Gly His Pro Ile Pro Thr Gln Gly Pro Gly Gly Tyr
    50                  55                  60

Pro Gln Asp Asn Met His Gln Met His Lys Pro Met Glu Ser Met His
65                  70                  75                  80

Glu Lys Gly Met Ser Asp Asp Pro Arg Tyr Asn Gln Met Lys Gly Met
                85                  90                  95

Gly Met Arg Ser Gly Gly His Ala Gly Met Gly Pro Pro Pro Ser Pro
            100                 105                 110

Met Asp Gln His Ser Gln Gly Tyr Pro Ser Pro Leu Gly Gly Ser Glu
        115                 120                 125

His Ala Ser Ser Pro Val Pro Ala Ser Gly Pro Ser Ser Gly Pro Gln
    130                 135                 140

Met Ser Ser Gly Pro Gly Gly Ala Pro Leu Asp Gly Ala Asp Pro Gln
145                 150                 155                 160

Ala Leu Gly Gln Gln Asn Arg Gly Pro Thr Pro Phe Asn Gln Asn Gln
                165                 170                 175

Leu His Gln Leu Arg Ala Gln Ile Met Ala Tyr Lys Met Leu Ala Arg
            180                 185                 190

Gly Gln Pro Leu Pro Asp His Leu Gln Met Ala Val Gln Gly Lys Arg
        195                 200                 205

Pro Met Pro Gly Met Gln Gln Gln Met Pro Thr Leu Pro Pro Pro Ser
    210                 215                 220

Val Ser Ala Thr Gly Pro Gly Pro Gly Pro Gly Pro Gly Pro Gly Pro
225                 230                 235                 240

Gly Pro Gly Pro Ala Pro Pro Asn Tyr Ser Arg Pro His Gly Met Gly
                245                 250                 255

Gly Pro Asn Met Pro Pro Pro Gly Pro Ser Gly Val Pro Pro Gly Met
            260                 265                 270

Pro Gly Gln Pro Pro Gly Gly Pro Pro Lys Pro Trp Pro Glu Gly Pro
        275                 280                 285
```

```
Met Ala Asn Ala Ala Ala Pro Thr Ser Thr Pro Gln Lys Leu Ile Pro
    290                 295                 300
Pro Gln Pro Thr Gly Arg Pro Ser Pro Ala Pro Pro Ala Val Pro Pro
305                 310                 315                 320
Ala Ala Ser Pro Val Met Pro Pro Gln Thr Gln Ser Pro Gly Gln Pro
                325                 330                 335
Ala Gln Pro Ala Pro Met Val Pro Leu His Gln Lys Gln Ser Arg Ile
            340                 345                 350
Thr Pro Ile Gln Lys Pro Arg Gly Leu Asp Pro Val Glu Ile Leu Gln
        355                 360                 365
Glu Arg Glu Tyr Arg Leu Gln Ala Arg Ile Ala His Arg Ile Gln Glu
370                 375                 380
Leu Glu Asn Leu Pro Gly Ser Leu Ala Gly Asp Leu Arg Thr Lys Ala
385                 390                 395                 400
Thr Ile Glu Leu Lys Ala Leu Arg Leu Leu Asn Phe Gln Arg Gln Leu
                405                 410                 415
Arg Gln Glu Val Val Val Cys Met Arg Arg Asp Thr Ala Leu Glu Thr
            420                 425                 430
Ala Leu Asn Ala Lys Ala Tyr Lys Arg Ser Lys Arg Gln Ser Leu Arg
        435                 440                 445
Glu Ala Arg Ile Thr Glu Lys Leu Glu Lys Gln Gln Lys Ile Glu Gln
450                 455                 460
Glu Arg Lys Arg Arg Gln Lys His Gln Glu Tyr Leu Asn Ser Ile Leu
465                 470                 475                 480
Gln His Ala Lys Asp Phe Lys Glu Tyr His Arg Ser Val Thr Gly Lys
                485                 490                 495
Ile Gln Lys Leu Thr Lys Ala Val Ala Thr Tyr His Ala Asn Thr Glu
            500                 505                 510
Arg Glu Gln Lys Lys Glu Asn Glu Arg Ile Glu Lys Glu Arg Met Arg
        515                 520                 525
Arg Leu Met Ala Glu Asp Glu Glu Gly Tyr Arg Lys Leu Ile Asp Gln
530                 535                 540
Lys Lys Asp Lys Arg Leu Ala Tyr Leu Leu Gln Gln Thr Asp Glu Tyr
545                 550                 555                 560
Val Ala Asn Leu Thr Glu Leu Val Arg Gln His Lys Ala Ala Gln Val
                565                 570                 575
Ala Lys Glu Lys Lys Lys Lys Lys Lys Lys Lys Ala Glu Asn Ala
            580                 585                 590
Glu Gly Gln Thr Pro Ala Ile Gly Pro Asp Gly Glu Pro Leu Asp Glu
        595                 600                 605
Thr Ser Gln Met Ser Asp Leu Pro Val Lys Val Ile His Val Glu Ser
610                 615                 620
Gly Lys Ile Leu Thr Gly Thr Asp Ala Pro Lys Ala Gly Gln Leu Glu
625                 630                 635                 640
Ala Trp Leu Glu Met Asn Pro Gly Tyr Glu Val Ala Pro Arg Ser Asp
                645                 650                 655
Ser Glu Glu Ser Gly Ser Glu Glu Glu Glu Glu Glu Glu Glu Glu Glu
            660                 665                 670
Gln Pro Gln Ala Ala Gln Pro Pro Thr Leu Pro Val Glu Lys Lys
        675                 680                 685
Lys Ile Pro Asp Pro Asp Ser Asp Asp Val Ser Glu Val Asp Ala Arg
690                 695                 700
His Ile Ile Glu Asn Ala Lys Gln Asp Val Asp Asp Glu Tyr Gly Val
```

```
705                 710                 715                 720
Ser Gln Ala Leu Ala Arg Gly Leu Gln Ser Tyr Tyr Ala Val Ala His
                725                 730                 735
Ala Val Thr Glu Arg Val Asp Lys Gln Ser Ala Leu Met Val Asn Gly
                740                 745                 750
Val Leu Lys Gln Tyr Gln Ile Lys Gly Leu Glu Trp Leu Val Ser Leu
                755                 760                 765
Tyr Asn Asn Leu Asn Gly Ile Leu Ala Asp Glu Met Gly Leu Gly
        770                 775                 780
Lys Thr Ile Gln Thr Ile Ala Leu Ile Thr Tyr Leu Met Glu His Lys
785                 790                 795                 800
Arg Ile Asn Gly Pro Phe Leu Ile Ile Val Pro Leu Ser Thr Leu Ser
                805                 810                 815
Asn Trp Ala Tyr Glu Phe Asp Lys Trp Ala Pro Ser Val Val Lys Val
                820                 825                 830
Ser Tyr Lys Gly Ser Pro Ala Ala Arg Arg Ala Phe Val Pro Gln Leu
                835                 840                 845
Arg Ser Gly Lys Phe Asn Val Leu Leu Thr Thr Tyr Glu Tyr Ile Ile
    850                 855                 860
Lys Asp Lys His Ile Leu Ala Lys Ile Arg Trp Lys Tyr Met Ile Val
865                 870                 875                 880
Asp Glu Gly His Arg Met Lys Asn His Cys Lys Leu Thr Gln Val
            885                 890                 895
Leu Asn Thr His Tyr Val Ala Pro Arg Arg Leu Leu Leu Thr Gly Thr
                900                 905                 910
Pro Leu Gln Asn Lys Leu Pro Glu Leu Trp Ala Leu Leu Asn Phe Leu
        915                 920                 925
Leu Pro Thr Ile Phe Lys Ser Cys Ser Thr Phe Glu Gln Trp Phe Asn
        930                 935                 940
Ala Pro Phe Ala Met Thr Gly Glu Lys Val Asp Leu Asn Glu Glu Glu
945                 950                 955                 960
Thr Ile Leu Ile Ile Arg Arg Leu His Lys Val Leu Arg Pro Phe Leu
                965                 970                 975
Leu Arg Arg Leu Lys Lys Glu Val Glu Ala Gln Leu Pro Glu Lys Val
            980                 985                 990
Glu Tyr Val Ile Lys Cys Asp Met Ser Ala Leu Gln Arg Val Leu Tyr
                995                1000                1005
Arg His Met Gln Ala Lys Gly Val Leu Leu Thr Asp Gly Ser Glu
    1010                1015                1020
Lys Asp Lys Lys Gly Lys Gly Gly Thr Lys Thr Leu Met Asn Thr
    1025                1030                1035
Ile Met Gln Leu Arg Lys Ile Cys Asn His Pro Tyr Met Phe Gln
    1040                1045                1050
His Ile Glu Glu Ser Phe Ser Glu His Leu Gly Phe Thr Gly Gly
    1055                1060                1065
Ile Val Gln Gly Leu Asp Leu Tyr Arg Ala Ser Gly Lys Phe Glu
    1070                1075                1080
Leu Leu Asp Arg Ile Leu Pro Lys Leu Arg Ala Thr Asn His Lys
    1085                1090                1095
Val Leu Leu Phe Cys Gln Met Thr Ser Leu Met Thr Ile Met Glu
    1100                1105                1110
Asp Tyr Phe Ala Tyr Arg Gly Phe Lys Tyr Leu Arg Leu Asp Gly
    1115                1120                1125
```

```
Thr Thr Lys Ala Glu Asp Arg Gly Met Leu Leu Lys Thr Phe Asn
    1130            1135                1140

Glu Pro Gly Ser Glu Tyr Phe Ile Phe Leu Leu Ser Thr Arg Ala
    1145            1150                1155

Gly Gly Leu Gly Leu Asn Leu Gln Ser Ala Asp Thr Val Ile Ile
    1160            1165                1170

Phe Asp Ser Asp Trp Asn Pro His Gln Asp Leu Gln Ala Gln Asp
    1175            1180                1185

Arg Ala His Arg Ile Gly Gln Gln Asn Glu Val Arg Val Leu Arg
    1190            1195                1200

Leu Cys Thr Val Asn Ser Val Glu Glu Lys Ile Leu Ala Ala Ala
    1205            1210                1215

Lys Tyr Lys Leu Asn Val Asp Gln Lys Val Ile Gln Ala Gly Met
    1220            1225                1230

Phe Asp Gln Lys Ser Ser Ser His Glu Arg Arg Ala Phe Leu Gln
    1235            1240                1245

Ala Ile Leu Glu His Glu Glu Gln Asp Glu Ser Arg His Cys Ser
    1250            1255                1260

Thr Gly Ser Gly Ser Ala Ser Phe Ala His Thr Ala Pro Pro Pro
    1265            1270                1275

Ala Gly Val Asn Pro Asp Leu Glu Glu Pro Pro Leu Lys Glu Glu
    1280            1285                1290

Asp Glu Val Pro Asp Asp Glu Thr Val Asn Gln Met Ile Ala Arg
    1295            1300                1305

His Glu Glu Glu Phe Asp Leu Phe Met Arg Met Asp Leu Asp Arg
    1310            1315                1320

Arg Arg Glu Glu Ala Arg Asn Pro Lys Arg Lys Pro Arg Leu Met
    1325            1330                1335

Glu Glu Asp Glu Leu Pro Ser Trp Ile Ile Lys Asp Asp Ala Glu
    1340            1345                1350

Val Glu Arg Leu Thr Cys Glu Glu Glu Glu Lys Met Phe Gly
    1355            1360                1365

Arg Gly Ser Arg His Arg Lys Glu Val Asp Tyr Ser Asp Ser Leu
    1370            1375                1380

Thr Glu Lys Gln Trp Leu Lys Ala Ile Glu Glu Gly Thr Leu Glu
    1385            1390                1395

Glu Ile Glu Glu Glu Val Arg Gln Lys Lys Ser Ser Arg Lys Arg
    1400            1405                1410

Lys Arg Asp Ser Asp Ala Gly Ser Ser Thr Pro Thr Thr Ser Thr
    1415            1420                1425

Arg Ser Arg Asp Lys Asp Asp Glu Ser Lys Lys Gln Lys Lys Arg
    1430            1435                1440

Gly Arg Pro Pro Ala Glu Lys Leu Ser Pro Asn Pro Pro Asn Leu
    1445            1450                1455

Thr Lys Lys Met Lys Lys Ile Val Asp Ala Val Ile Lys Tyr Lys
    1460            1465                1470

Asp Ser Ser Ser Gly Arg Gln Leu Ser Glu Val Phe Ile Gln Leu
    1475            1480                1485

Pro Ser Arg Lys Glu Leu Pro Glu Tyr Tyr Glu Leu Ile Arg Lys
    1490            1495                1500

Pro Val Asp Phe Lys Lys Ile Lys Glu Arg Ile Arg Asn His Lys
    1505            1510                1515
```

```
Tyr Arg Ser Leu Asn Asp Leu Glu Lys Asp Val Met Leu Leu Cys
    1520                1525                1530

Gln Asn Ala Gln Thr Phe Asn Leu Glu Gly Ser Leu Ile Tyr Glu
    1535                1540                1545

Asp Ser Ile Val Leu Gln Ser Val Phe Thr Ser Val Arg Gln Lys
    1550                1555                1560

Ile Glu Lys Glu Asp Asp Ser Glu Gly Glu Ser Glu Glu Glu
    1565                1570                1575

Glu Glu Gly Glu Glu Glu Gly Ser Glu Ser Glu Ser Arg Ser Val
    1580                1585                1590

Lys Val Lys Ile Lys Leu Gly Arg Lys Glu Lys Ala Gln Asp Arg
    1595                1600                1605

Leu Lys Gly Gly Arg Arg Arg Pro Ser Arg Gly Ser Arg Ala Lys
    1610                1615                1620

Pro Val Val Ser Asp Asp Ser Glu Glu Glu Gln Glu Glu Asp
    1625                1630                1635

Arg Ser Gly Ser Gly Ser Glu Glu Asp
    1640                1645

<210> SEQ ID NO 3
<211> LENGTH: 5892
<212> TYPE: RNA
<213> ORGANISM: Homo sapiens

<400> SEQUENCE: 3
gcgtcttccg cgcccgcgg aggaggcgag ggtgggacgc tgggcggagc ccgagtttag      60
gaagaggagg ggacggctgt catcaatgaa gtcatattca taatctagtc ctctctccct    120
ctgtttctgt actctgggtg actcagagag ggaagagatt cagccagcac actcctcgcg    180
agcaagcatt actctactga ctggcagaga caggagaggt agatgtccac gcccacagac    240
cctggtgcga tgccccaccc agggccttcg ccggggcctg ggccttcccc tgggccaatt    300
cttgggccta gtccaggacc aggaccatcc ccaggttccg tccacagcat gatggggcca    360
agtcctggac ctccaagtgt ctcccatcct atgccgacga tggggtccac agacttccca    420
caggaaggca tgcatcaaat gcataagccc atcgatggta tacatgacaa ggggattgta    480
gaagacatcc attgtggatc catgaagggc actggtatgc gaccacctca cccaggcatg    540
ggccctcccc agagtccaat ggatcaacac agccaaggtt atatgtcacc acacccatct    600
ccattaggag ccccagagca cgtctccagc cctatgtctg gaggagcccc aactccacct    660
cagatgccac caagccagcc gggggccctc atcccaggtg atccgcaggc catgagccag    720
cccaacagag gtccctcacc tttcagtcct gtccagctgc atcagcttcg agctcagatt    780
ttagcttata aatgctggc ccgaggccag cccctccccg aaacgctgca gcttgcagtc    840
caggggaaaa ggacgttgcc tggcttgcag caacaacagc agcagcaaca gcagcagcag    900
cagcagcagc agcagcagca gcagcagcaa cagcagccgc agcagcagcc gccgcaacca    960
cagacgcagc aacaacagca gccggcccctt gttaactaca acagaccatc tggcccgggg   1020
ccggagctga gcgggcccgag caccccgcag aagctgccgg tgcccgcgcc cggcggccgg   1080
cccctcgccg cgcccccgc agccgcgcag ccgcccgcgg ccgcagtgcc cgggccctca   1140
gtgccgcagc cggccccggg gcagccctcg cccgtcctcc agctgcagca gaagcagagc   1200
cgcatcagcc ccatccagaa accgcaaggc ctggaccccg tggaaattct gcaagagcgg   1260
gaatacagac ttcaggcccg catagctcat aggatacaag aactggaaaa tctgcctggc   1320
```

```
tctttgccac cagatttaag aaccaaagca accgtggaac taaaagcact tcggttactc    1380
aatttccagc gtcagctgag acaggaggtg gtggcctgca tgcgcaggga cacgaccctg    1440
gagacggctc tcaactccaa agcatacaaa cggagcaagc gccagactct gagagaagct    1500
cgcatgaccg agaagctgga gaagcagcag aagattgagc aggagaggaa acgccgtcag    1560
aaacaccagg aatacctgaa cagtattttg caacatgcaa aagattttaa ggaatatcat    1620
cggtctgtgg ccggaaagat ccagaagctc tccaaagcag tggcaacttg gcatgccaac    1680
actgaaagag agcagaagaa ggagacagag cggattgaaa aggagagaat gcggcgactg    1740
atggctgaag atgaggaggg ttatagaaaa ctgattgatc aaaagaaaga caggcgttta    1800
gcttaccttt tgcagcagac cgatgagtat gtagccaatc tgaccaatct ggtttgggag    1860
cacaagcaag cccaggcagc caaagagaag aagaagagga ggaggaggaa gaagaaggct    1920
gaggagaatg cagagggtgg ggagtctgcc ctgggaccgg atggagagcc catagatgag    1980
agcagccaga tgagtgacct ccctgtcaaa gtgactcaca cagaaaccgg caaggttctg    2040
ttcggaccag aagcacccaa agcaagtcag ctggacgcct ggctggaaat gaatcctggt    2100
tatgaagttg cccctagatc tgacagtgaa gagagtgatt ctgattatga ggaagaggat    2160
gaggaagaag agtccagtag gcaggaaacc gaagagaaaa tactcctgga tccaaatagc    2220
gaagaagttt ctgagaagga tgctaagcag atcattgaga cagctaagca agacgtggat    2280
gatgaataca gcatgcagta cagtgccagg ggctcccagt cctactacac cgtggctcat    2340
gccatctcgg agagggtgga gaaacagtct gccctcctaa ttaatgggac cctaaagcat    2400
taccagctcc agggcctgga atggatggtt ccctgtata ataacaactt gaacggaatc    2460
ttagccgatg aaatggggct tggaaagacc atacagacca ttgcactcat cacttatctg    2520
atggagcaca aaagactcaa tggcccctat ctcatcattg ttcccctttc gactctatct    2580
aactggacat atgaatttga caaatgggct ccttctgtgg tgaagatttc ttacaagggt    2640
actcctgcca tgcgtcgctc ccttgtcccc cagctacgga gtggcaaatt caatgtcctc    2700
ttgactactt atgagtatat tataaaagac aagcacattc ttgcaaagat tcggtggaaa    2760
tacatgatag tggacgaagg ccaccgaatg aagaatcacc actgcaagct gactcaggtc    2820
ttgaacactc actatgtggc ccccagaagg atcctcttga ctgggacccc gctgcagaat    2880
aagctccctg aactctgggc cctcctcaac ttcctcctcc caacaatttt taagagctgc    2940
agcacatttg aacaatggtt caatgctcca tttgccatga ctggtgaaag ggtggactta    3000
aatgaagaag aaactatatt gatcatcagg cgtctacata aggtgttaag accatttta    3060 ctaaggagac tgaagaaaga agttgaatcc cagcttcccg aaaaagtgga atatgtgatc    3120
aagtgtgaca tgtcagctct gcagaagatt ctgtatcgcc atatgcaagc caggggatc    3180 cttctcacag atggttctga gaaagataag aaggggaaag gaggtgctaa gacacttatg    3240
aacactatta tgcagttgag aaaaatctgc aaccacccat atatgtttca gcacattgag    3300
gaatcctttg ctgaacacct aggctattca aatggggtca tcaatggggc tgaactgtat    3360
cgggcctcag ggaagtttga gctgcttgat cgtattctgc aaaattgag agcgactaat    3420 caccgagtgc tgcttttctg ccagatgaca tctctcatga ccatcatgga ggattattt    3480 gcttttcgga acttccttta cctacgcctt gatggcacca ccaagtctga agatcgtgct    3540
gctttgctga gaaaattcaa tgaacctgga tcccagtatt tcattttctt gctgagcaca    3600
agagctggtg gcctgggctt aaatcttcag gcagctgata cagtggtcat ctttgacagc    3660
gactggaatc ctcatcagga tctgcaggcc caagaccgag ctcaccgcat cgggcagcag    3720
```

```
aacgaggtcc gggtactgag gctctgtacc gtgaacagcg tggaggaaaa gatcctcgcg    3780
gccgcaaaat acaagctgaa cgtggatcag aaagtgatcc aggcgggcat gtttgaccaa    3840
aagtcttcaa gccacgagcg gagggcattc ctgcaggcca tcttggagca tgaggaggaa    3900
aatgaggaag aagatgaagt accggacgat gagactctga accaaatgat tgctcgacga    3960
gaagaagaat ttgaccttt tatgcggatg gacatggacc ggcggaggga agatgcccgg    4020
aacccgaaac ggaagccccg tttaatggag gaggatgagc tgccctcctg gatcattaag    4080
gatgacgctg aagtagaaag gctcacctgt gaagaagagg aggagaaaat atttgggagg    4140
gggtcccgcc agcgccgtga cgtggactac agtgacgccc tcacggagaa gcagtggcta    4200
agggccatcg aagacggcaa tttggaggaa atggaagagg aagtacggct taagaagcga    4260
aaaagacgaa gaaatgtgga taaagatcct gcaaaagaag atgtggaaaa agctaagaag    4320
agaagaggcc gccctcccgc tgagaaactg tcaccaaatc cccccaaact gacaaagcag    4380
atgaacgcta tcatcgatac tgtgataaac tacaaagata ggtgtaacgt ggagaaggtg    4440
cccagtaatt ctcagttgga aatagaagga aacagttcag ggcgacagct cagtgaagtc    4500
ttcattcagt taccttcaag gaaagaatta ccagaatact atgaattaat taggaagcca    4560
gtggatttca aaaaaataaa ggaaaggatt cgtaatcata agtaccggag cctaggcgac    4620
ctggagaagg atgtcatgct tctctgtcac aacgctcaga cgttcaacct ggagggatcc    4680
cagatctatg aagactccat cgtcttacag tcagtgttta agagtgcccg gcagaaaatt    4740
gccaaagagg aagagagtga ggatgaaagc aatgaagagg aggaagagga agatgaagaa    4800
gagtcagagt ccgaggcaaa atcagtcaag gtgaaaatta agctcaataa aaaagatgac    4860
aaaggccggg acaaagggaa aggcaagaaa aggccaaatc gaggaaaagc caaacctgta    4920
gtgagcgatt ttgacagcga tgaggagcag gatgaacgtg aacagtcaga aggaagtggg    4980
acggatgatg agtgatcagt atggacctt ttccttggta gaactgaatt ccttcctccc    5040
ctgtctcatt tctacccagt gagttcattt gtcatatagg cactgggttg tttctatatc    5100
atcatcgtct ataaactagc tttaggatag tgccagacaa acatatgata tcatggtgta    5160
aaaacacac acatacacaa atatttgtaa catattgtga ccaaatgggc ctcaaagatt    5220
cagattgaaa caaacaaaaa gcttttgatg gaaaatatgt gggtggatag tatatttcta    5280
tgggtgggtc taatttggta acggtttgat tgtgcctggt tttatcacct gttcagatga    5340
gaagatttt gtcttttgta gcactgataa ccaggagaag ccattaaaag ccactggtta    5400
ttttattttt catcaggcaa ttttcgaggt tttatttgt tcggtattgt tttttttacac    5460
tgtggtacat ataagcaact ttaataggtg ataaatgtac agtagttaga tttcacctgc    5520
atatacattt ttccattta tgctctatga tctgaacaaa gcttttgta attgtataag    5580
atttatgtct actgtaaaca ttgcttaatt ttttgctct tgatttaaa aaaagttttg    5640
ttgaaagcgc tattgaatat tgcaatctat atagtgtatt ggatggcttc ttttgtcacc    5700
ctgatctcct atgttaccaa tgtgtatcgt ctccttctcc ctaaagtgta cttaatctt    5760
gctttctttg cacaatgtct ttggttgcaa gtcataagcc tgaggcaaat aaaattccag    5820
taatttcgaa gaatgtggtg ttggtgcttt cctaataaag aaataattta gcttgacaaa    5880
aaaaaaaaaa aa                                                       5892
```

<210> SEQ ID NO 4
<211> LENGTH: 1590
<212> TYPE: PRT

<213> ORGANISM: Homo sapiens

<400> SEQUENCE: 4

Met Ser Thr Pro Thr Asp Pro Gly Ala Met Pro His Pro Gly Pro Ser
1               5                   10                  15

Pro Gly Pro Gly Pro Ser Pro Gly Pro Ile Leu Gly Pro Ser Pro Gly
            20                  25                  30

Pro Gly Pro Ser Pro Gly Ser Val His Ser Met Met Gly Pro Ser Pro
        35                  40                  45

Gly Pro Pro Ser Val Ser His Pro Met Pro Thr Met Gly Ser Thr Asp
    50                  55                  60

Phe Pro Gln Glu Gly Met His Gln Met His Lys Pro Ile Asp Gly Ile
65                  70                  75                  80

His Asp Lys Gly Ile Val Glu Asp Ile His Cys Gly Ser Met Lys Gly
                85                  90                  95

Thr Gly Met Arg Pro Pro His Pro Gly Met Gly Pro Pro Gln Ser Pro
            100                 105                 110

Met Asp Gln His Ser Gln Gly Tyr Met Ser Pro His Pro Ser Pro Leu
        115                 120                 125

Gly Ala Pro Glu His Val Ser Ser Pro Met Ser Gly Gly Gly Pro Thr
    130                 135                 140

Pro Pro Gln Met Pro Pro Ser Gln Pro Gly Ala Leu Ile Pro Gly Asp
145                 150                 155                 160

Pro Gln Ala Met Ser Gln Pro Asn Arg Gly Pro Ser Pro Phe Ser Pro
                165                 170                 175

Val Gln Leu His Gln Leu Arg Ala Gln Ile Leu Ala Tyr Lys Met Leu
            180                 185                 190

Ala Arg Gly Gln Pro Leu Pro Glu Thr Leu Gln Leu Ala Val Gln Gly
        195                 200                 205

Lys Arg Thr Leu Pro Gly Leu Gln Gln Gln Gln Gln Gln Gln Gln Gln
    210                 215                 220

Gln Gln Gln Gln Gln Gln Gln Gln Gln Gln Gln Gln Gln Gln Pro Gln
225                 230                 235                 240

Gln Gln Pro Pro Gln Pro Gln Thr Gln Gln Gln Gln Pro Ala Leu
                245                 250                 255

Val Asn Tyr Asn Arg Pro Ser Gly Pro Gly Pro Glu Leu Ser Gly Pro
            260                 265                 270

Ser Thr Pro Gln Lys Leu Pro Val Pro Ala Pro Gly Gly Arg Pro Ser
        275                 280                 285

Pro Ala Pro Pro Ala Ala Ala Gln Pro Ala Ala Ala Val Pro Gly
    290                 295                 300

Pro Ser Val Pro Gln Pro Ala Pro Gly Gln Pro Ser Pro Val Leu Gln
305                 310                 315                 320

Leu Gln Gln Lys Gln Ser Arg Ile Ser Pro Ile Gln Lys Pro Gln Gly
                325                 330                 335

Leu Asp Pro Val Glu Ile Leu Gln Glu Arg Glu Tyr Arg Leu Gln Ala
            340                 345                 350

Arg Ile Ala His Arg Ile Gln Glu Leu Glu Asn Leu Pro Gly Ser Leu
        355                 360                 365

Pro Pro Asp Leu Arg Thr Lys Ala Thr Val Glu Leu Lys Ala Leu Arg
    370                 375                 380

Leu Leu Asn Phe Gln Arg Gln Leu Arg Gln Glu Val Val Ala Cys Met
385                 390                 395                 400

```
Arg Arg Asp Thr Thr Leu Glu Thr Ala Leu Asn Ser Lys Ala Tyr Lys
                405                 410                 415
Arg Ser Lys Arg Gln Thr Leu Arg Glu Ala Arg Met Thr Glu Lys Leu
            420                 425                 430
Glu Lys Gln Gln Lys Ile Glu Gln Arg Lys Arg Arg Gln Lys His
        435                 440                 445
Gln Glu Tyr Leu Asn Ser Ile Leu Gln His Ala Lys Asp Phe Lys Glu
    450                 455                 460
Tyr His Arg Ser Val Ala Gly Lys Ile Gln Lys Leu Ser Lys Ala Val
465                 470                 475                 480
Ala Thr Trp His Ala Asn Thr Glu Arg Glu Gln Lys Lys Glu Thr Glu
                485                 490                 495
Arg Ile Glu Lys Glu Arg Met Arg Arg Leu Met Ala Glu Asp Glu Glu
            500                 505                 510
Gly Tyr Arg Lys Leu Ile Asp Gln Lys Lys Asp Arg Arg Leu Ala Tyr
        515                 520                 525
Leu Leu Gln Gln Thr Asp Glu Tyr Val Ala Asn Leu Thr Asn Leu Val
    530                 535                 540
Trp Glu His Lys Gln Ala Gln Ala Ala Lys Glu Lys Lys Lys Arg Arg
545                 550                 555                 560
Arg Arg Lys Lys Lys Ala Glu Glu Asn Ala Glu Gly Gly Glu Ser Ala
                565                 570                 575
Leu Gly Pro Asp Gly Glu Pro Ile Asp Glu Ser Ser Gln Met Ser Asp
            580                 585                 590
Leu Pro Val Lys Val Thr His Thr Glu Thr Gly Lys Val Leu Phe Gly
        595                 600                 605
Pro Glu Ala Pro Lys Ala Ser Gln Leu Asp Ala Trp Leu Glu Met Asn
    610                 615                 620
Pro Gly Tyr Glu Val Ala Pro Arg Ser Asp Ser Glu Glu Ser Asp Ser
625                 630                 635                 640
Asp Tyr Glu Glu Glu Asp Glu Glu Glu Ser Ser Arg Gln Glu Thr
                645                 650                 655
Glu Glu Lys Ile Leu Leu Asp Pro Asn Ser Glu Glu Val Ser Glu Lys
            660                 665                 670
Asp Ala Lys Gln Ile Ile Glu Thr Ala Lys Gln Asp Val Asp Asp Glu
        675                 680                 685
Tyr Ser Met Gln Tyr Ser Ala Arg Gly Ser Gln Ser Tyr Tyr Thr Val
    690                 695                 700
Ala His Ala Ile Ser Glu Arg Val Glu Lys Gln Ser Ala Leu Leu Ile
705                 710                 715                 720
Asn Gly Thr Leu Lys His Tyr Gln Leu Gln Gly Leu Glu Trp Met Val
                725                 730                 735
Ser Leu Tyr Asn Asn Asn Leu Asn Gly Ile Leu Ala Asp Glu Met Gly
            740                 745                 750
Leu Gly Lys Thr Ile Gln Thr Ile Ala Leu Ile Thr Tyr Leu Met Glu
        755                 760                 765
His Lys Arg Leu Asn Gly Pro Tyr Leu Ile Ile Val Pro Leu Ser Thr
    770                 775                 780
Leu Ser Asn Trp Thr Tyr Glu Phe Asp Lys Trp Ala Pro Ser Val Val
785                 790                 795                 800
Lys Ile Ser Tyr Lys Gly Thr Pro Ala Met Arg Arg Ser Leu Val Pro
                805                 810                 815
Gln Leu Arg Ser Gly Lys Phe Asn Val Leu Leu Thr Thr Tyr Glu Tyr
```

```
             820                 825                 830
Ile Ile Lys Asp Lys His Ile Leu Ala Lys Ile Arg Trp Lys Tyr Met
             835                 840                 845
Ile Val Asp Glu Gly His Arg Met Lys Asn His His Cys Lys Leu Thr
             850                 855                 860
Gln Val Leu Asn Thr His Tyr Val Ala Pro Arg Arg Ile Leu Leu Thr
865                  870                 875                 880
Gly Thr Pro Leu Gln Asn Lys Leu Pro Glu Leu Trp Ala Leu Leu Asn
                         885                 890                 895
Phe Leu Leu Pro Thr Ile Phe Lys Ser Cys Ser Thr Phe Glu Gln Trp
                 900                 905                 910
Phe Asn Ala Pro Phe Ala Met Thr Gly Glu Arg Val Asp Leu Asn Glu
             915                 920                 925
Glu Glu Thr Ile Leu Ile Arg Arg Leu His Lys Val Leu Arg Pro
         930                 935                 940
Phe Leu Leu Arg Arg Leu Lys Lys Glu Val Glu Ser Gln Leu Pro Glu
945                  950                 955                 960
Lys Val Glu Tyr Val Ile Lys Cys Asp Met Ser Ala Leu Gln Lys Ile
                 965                 970                 975
Leu Tyr Arg His Met Gln Ala Lys Gly Ile Leu Leu Thr Asp Gly Ser
             980                 985                 990
Glu Lys Asp Lys Lys Gly Lys Gly  Gly Ala Lys Thr Leu  Met Asn Thr
         995                 1000                1005
Ile Met  Gln Leu Arg Lys Ile  Cys Asn His Pro Tyr  Met Phe Gln
        1010                1015                1020
His Ile  Glu Glu Ser Phe Ala  Glu His Leu Gly Tyr  Ser Asn Gly
        1025                1030                1035
Val Ile  Asn Gly Ala Glu Leu  Tyr Arg Ala Ser Gly  Lys Phe Glu
        1040                1045                1050
Leu Leu  Asp Arg Ile Leu Pro  Lys Leu Arg Ala Thr  Asn His Arg
        1055                1060                1065
Val Leu  Leu Phe Cys Gln Met  Thr Ser Leu Met Thr  Ile Met Glu
        1070                1075                1080
Asp Tyr  Phe Ala Phe Arg Asn  Phe Leu Tyr Leu Arg  Leu Asp Gly
        1085                1090                1095
Thr Thr  Lys Ser Glu Asp Arg  Ala Ala Leu Leu Lys  Lys Phe Asn
        1100                1105                1110
Glu Pro  Gly Ser Gln Tyr Phe  Ile Phe Leu Leu Ser  Thr Arg Ala
        1115                1120                1125
Gly Gly  Leu Gly Leu Asn Leu  Gln Ala Ala Asp Thr  Val Val Ile
        1130                1135                1140
Phe Asp  Ser Asp Trp Asn Pro  His Gln Asp Leu Gln  Ala Gln Asp
        1145                1150                1155
Arg Ala  His Arg Ile Gly Gln  Gln Asn Glu Val Arg  Val Leu Arg
        1160                1165                1170
Leu Cys  Thr Val Asn Ser Val  Glu Glu Lys Ile Leu  Ala Ala Ala
        1175                1180                1185
Lys Tyr  Lys Leu Asn Val Asp  Gln Lys Val Ile Gln  Ala Gly Met
        1190                1195                1200
Phe Asp  Gln Lys Ser Ser Ser  His Glu Arg Arg Ala  Phe Leu Gln
        1205                1210                1215
Ala Ile  Leu Glu His Glu Glu  Glu Asn Glu Glu Glu  Asp Glu Val
        1220                1225                1230
```

```
Pro Asp Asp Glu Thr Leu Asn Gln Met Ile Ala Arg Arg Glu Glu
    1235                1240                1245

Glu Phe Asp Leu Phe Met Arg Met Asp Met Asp Arg Arg Arg Glu
    1250                1255                1260

Asp Ala Arg Asn Pro Lys Arg Lys Pro Arg Leu Met Glu Glu Asp
    1265                1270                1275

Glu Leu Pro Ser Trp Ile Ile Lys Asp Asp Ala Glu Val Glu Arg
    1280                1285                1290

Leu Thr Cys Glu Glu Glu Glu Lys Ile Phe Gly Arg Gly Ser
    1295                1300                1305

Arg Gln Arg Arg Asp Val Asp Tyr Ser Asp Ala Leu Thr Glu Lys
    1310                1315                1320

Gln Trp Leu Arg Ala Ile Glu Asp Gly Asn Leu Glu Glu Met Glu
    1325                1330                1335

Glu Glu Val Arg Leu Lys Lys Arg Lys Arg Arg Asn Val Asp
    1340                1345                1350

Lys Asp Pro Ala Lys Glu Asp Val Glu Lys Ala Lys Lys Arg Arg
    1355                1360                1365

Gly Arg Pro Pro Ala Glu Lys Leu Ser Pro Asn Pro Pro Lys Leu
    1370                1375                1380

Thr Lys Gln Met Asn Ala Ile Ile Asp Thr Val Ile Asn Tyr Lys
    1385                1390                1395

Asp Arg Cys Asn Val Glu Lys Val Pro Ser Asn Ser Gln Leu Glu
    1400                1405                1410

Ile Glu Gly Asn Ser Ser Gly Arg Gln Leu Ser Glu Val Phe Ile
    1415                1420                1425

Gln Leu Pro Ser Arg Lys Glu Leu Pro Glu Tyr Tyr Glu Leu Ile
    1430                1435                1440

Arg Lys Pro Val Asp Phe Lys Lys Ile Lys Glu Arg Ile Arg Asn
    1445                1450                1455

His Lys Tyr Arg Ser Leu Gly Asp Leu Glu Lys Asp Val Met Leu
    1460                1465                1470

Leu Cys His Asn Ala Gln Thr Phe Asn Leu Glu Gly Ser Gln Ile
    1475                1480                1485

Tyr Glu Asp Ser Ile Val Leu Gln Ser Val Phe Lys Ser Ala Arg
    1490                1495                1500

Gln Lys Ile Ala Lys Glu Glu Glu Ser Glu Asp Glu Ser Asn Glu
    1505                1510                1515

Glu Glu Glu Glu Glu Asp Glu Glu Ser Glu Ser Glu Ala Lys
    1520                1525                1530

Ser Val Lys Val Lys Ile Lys Leu Asn Lys Lys Asp Asp Lys Gly
    1535                1540                1545

Arg Asp Lys Gly Lys Gly Lys Arg Pro Asn Arg Gly Lys Ala
    1550                1555                1560

Lys Pro Val Val Ser Asp Phe Asp Ser Asp Glu Glu Gln Asp Glu
    1565                1570                1575

Arg Glu Gln Ser Glu Gly Ser Gly Thr Asp Asp Glu
    1580                1585                1590
```